(12) United States Patent
Bhat et al.

(10) Patent No.: US 8,308,971 B1
(45) Date of Patent: Nov. 13, 2012

(54) MATERIALS FOR BATTERY ELECTROLYTES AND METHODS FOR USE

(75) Inventors: Vinay V. Bhat, San Diego, CA (US); Gang Cheng, San Diego, CA (US); Steven Kaye, San Diego, CA (US); Bin Li, San Diego, CA (US); Risa Olugbile, San Diego, CA (US); Jen-Hsien Yang, San Diego, CA (US)

(73) Assignee: Wildcat Discovery Technologies, Inc., San Diego, CA (US)

( * ) Notice: Subject to any disclaimer, the term of this patent is extended or adjusted under 35 U.S.C. 154(b) by 0 days.

(21) Appl. No.: 13/459,773

(22) Filed: Apr. 30, 2012

Related U.S. Application Data

(60) Provisional application No. 61/597,509, filed on Feb. 10, 2012, provisional application No. 61/543,262, filed on Oct. 4, 2011, provisional application No. 61/495,318, filed on Jun. 9, 2011.

(51) Int. Cl.
| | |
|---|---|
| H01G 9/02 | (2006.01) |
| H01B 1/00 | (2006.01) |
| H01B 1/12 | (2006.01) |
| H01M 6/16 | (2006.01) |
| C07F 7/10 | (2006.01) |
| C07F 7/04 | (2006.01) |

(52) U.S. Cl. ........ 252/62.2; 252/500; 556/418; 429/341
(58) Field of Classification Search ................. 252/62.2, 252/500; 556/418; 429/341
See application file for complete search history.

(56) References Cited

U.S. PATENT DOCUMENTS

| | | | |
|---|---|---|---|
| 5,830,600 A | 11/1998 | Narang et al. | |
| 5,874,018 A | 2/1999 | Ferrar et al. | |
| 6,203,942 B1 | 3/2001 | Gan et al. | |
| 6,379,846 B1 | 4/2002 | Terahara et al. | |
| 6,416,901 B1 | 7/2002 | Fauteux et al. | |
| 6,680,147 B2 | 1/2004 | Lee | |
| 6,872,493 B2 | 3/2005 | Yamada et al. | |
| 6,887,619 B2 | 5/2005 | West et al. | |
| 6,902,850 B2 | 6/2005 | Wariishi et al. | |
| 6,995,225 B2 | 2/2006 | Arai et al. | |
| 7,097,942 B2 | 8/2006 | Hwang et al. | |
| 7,169,510 B2 | 1/2007 | Awano et al. | |
| 7,211,353 B2 | 5/2007 | Kashida et | |
| 7,226,702 B2 | 6/2007 | Oh et al. | |
| 7,241,536 B2 | 7/2007 | Kim et al. | |
| 7,252,908 B2 | 8/2007 | Kim et al. | |
| 7,255,966 B2 | 8/2007 | Kim et al. | |
| 7,351,501 B2 | 4/2008 | Jung et al. | |
| 7,378,193 B2 | 5/2008 | Kang et al. | |
| 7,410,731 B2 | 8/2008 | Yoon et al. | |
| 7,459,239 B2 | 12/2008 | Kashida et al. | |
| 7,473,491 B1 | 1/2009 | Amine et al. | |
| 7,494,746 B2 | 2/2009 | Tarnopolsky | |
| 7,498,102 B2 | 3/2009 | Oh et al. | |
| 7,588,859 B1 | 9/2009 | Oh et al. | |
| 7,598,003 B1 | 10/2009 | Yoon et al. | |
| 7,622,220 B2 | 11/2009 | Kim et al. | |
| 7,679,884 B2 | 3/2010 | West et al. | |
| 7,695,860 B2 | 4/2010 | Amine et al. | |
| 7,718,321 B2 | 5/2010 | Yoon et al. | |
| 7,744,772 B2 | 6/2010 | Gambut-Garel et al. | |
| 7,799,471 B2 | 9/2010 | Lee et al. | |
| 7,803,487 B2 | 9/2010 | Shima | |
| 7,833,665 B2 | 11/2010 | Mah et al. | |
| 7,846,581 B2 | 12/2010 | Barrandon et al. | |
| 7,851,090 B2 | 12/2010 | Park et al. | |
| 7,883,801 B2 | 2/2011 | Shimizu et al. | |
| 2004/0234865 A1 | 11/2004 | Sato et al. | |
| 2006/0269846 A1 | 11/2006 | Xu et al. | |
| 2008/0134492 A1 | 6/2008 | Amine et al. | |
| 2008/0138714 A1 | 6/2008 | Ihara et al. | |
| 2008/0138715 A1 | 6/2008 | Ihara et al. | |
| 2008/0166637 A1 | 7/2008 | Inagaki et al. | |
| 2009/0163394 A1 | 6/2009 | Muraishi et al. | |
| 2009/0191465 A1 | 7/2009 | Hwang et al. | |
| 2009/0197167 A1 | 8/2009 | Olschimke | |
| 2009/0202892 A1 | 8/2009 | Inagaki et al. | |
| 2009/0263726 A1 | 10/2009 | Yamaguchi et al. | |
| 2009/0286155 A1 | 11/2009 | Takehara | |
| 2009/0311609 A1 | 12/2009 | Saisho et al. | |
| 2010/0015514 A1 | 1/2010 | Miyagi et al. | |
| 2010/0092863 A1 | 4/2010 | Kim | |
| 2010/0099031 A1 | 4/2010 | Kato et al. | |
| 2010/0183926 A1 | 7/2010 | Kim et al. | |
| 2010/0216036 A1 | 8/2010 | Shima | |
| 2010/0330433 A1 | 12/2010 | Amine et al. | |
| 2011/0027663 A1 | 2/2011 | Ohkubo et al. | |
| 2011/0123870 A1 | 5/2011 | Oh et al. | |

(Continued)

OTHER PUBLICATIONS

Saleur et al. First synthesis of 1,4-bis(acylsilanes). Tetrahedron Letters 41 (2000) 321-324.*
Bouillon et al. Synthesis and Intramolecular Adol Reactions of 1,6 and 1,7-Bis(acylsilanes). Eur. J. Org Chem (1999) 1571-1580.*
Fisher et al., "Lithium Battery Materials LiMPO4 (M) Mn, Fe, Co, and Ni)" Chem. Mater. 2008, 20, 5907-5915.
Goodenough et al., "Challenges for Rechargeable Li Batteries," Chemistry of Materials 22, 587-603 (2010)!
Johnson et al., "Synthesis, Characterization and Electrochemistry of Lithium Battery Electrodes" Chem. Mater., 20, 6095-6106 (2008).
Kang et al., "Interpreting the structural and electrochemical complexity of 0.5Li2MnO3-0.5LiMO2 electrodes for lithium batteries" J. Mater. Chem., 17, 2069-2077 (2007).

(Continued)

*Primary Examiner* — Lorna M Douyon
*Assistant Examiner* — Tanisha Diggs
(74) *Attorney, Agent, or Firm* — Corridor Law Group, P.C.

(57) ABSTRACT

Described herein are materials for use in electrolytes that provide a number of desirable characteristics when implemented within batteries, such as high stability during battery cycling up to high temperatures high voltages, high discharge capacity, high coulombic efficiency, and excellent retention of discharge capacity and coulombic efficiency over several cycles of charging and discharging. In some embodiments, a high voltage electrolyte includes a base electrolyte and a set of additive compounds, which impart these desirable performance characteristics.

20 Claims, 38 Drawing Sheets

U.S. PATENT DOCUMENTS

2011/0136018 A1    6/2011  Nogi et al.
2011/0274985 A1   11/2011  Usrey et al.

OTHER PUBLICATIONS

Nagahama et al., "High Voltage Performances of Li2NiPO4F Cath
Marom et al., "A review of advanced and practical lithium battery materials," J. Mater. Chem., 21, 9938 (2011)! ode with Dinitrile-Based Electrolytes," Journal of the Electrochemical Society, 157 (6) A748-A752 (2010)!

Xu et al., "Sulfone-based Electrolytes for Lithium-Ion Batteries," Journal of the Electrochemical Society, 149 (7) A920-A926 (2002).
Yi et al., "Recent developments in the doping of LiNi0.5Mn1.5O4 cathode material for 5 V lithium-ion batteries," Ionics (2011) 17:383-389!
Zhi-Ping et al., "Li- Site and Metal-Site Ion Doping in Phosphate-Olivine LiCoPO4 by First-Principles Calculation," Chin. Phys. Lett. 26 (3) 038202 (2009.

\* cited by examiner

MATERIALS FOR BATTERY ELECTROLYTES AND METHODS FOR USE

This application claims priority to and the benefit of each of the following applications: U.S. Provisional Application No. 61/495,318 filed Jun. 9, 2011 entitled "Battery Electrolytes for High Voltage Cathode Materials"; U.S. Provisional Application No. 61/543,262 filed Oct. 4, 2011 entitled "Battery Electrolytes for High Voltage Cathode Materials"; and U.S. Provisional Application No. 61/597,509 filed Feb. 10, 2012 entitled "Battery Electrolytes for High Voltage Cathode Materials"; each of which applications is incorporated herein by reference.

BACKGROUND OF THE INVENTION

The invention relates generally to battery electrolytes. More particularly, the invention relates to battery electrolytes to improve stability of batteries, such as one or more of high voltage stability, thermal stability, electrochemical stability, and chemical stability.

An electrolyte serves to transportions and prevent electrical contact between electrodes in a battery. Organic carbonate-based electrolytes are most commonly used in lithium-ion ("Li-ion") batteries, and, more recently, efforts have been made to develop new classes of electrolytes based on sulfones, silanes, and nitriles. Unfortunately, these conventional electrolytes typically cannot be operated at high voltages, since they are unstable above 4.5 V or other high voltages. At high voltages, conventional electrolytes can decompose by catalytic oxidation in the presence of cathode materials to produce undesirable products that affect both the performance and safety of a battery.

In the case of Li-ion batteries, cobalt and nickel-containing phosphates, fluorophosphates, fluorosulphates, spinels, and silicates have been reported to have higher energy densities than $LiFePO_4$, $LiMn_2O_4$, and other commonly used cathode materials. However, these cathode materials also have redox potentials greater than 4.5 V, allowing for operation of the battery at higher voltages but also possibly causing severe electrolyte decomposition in the battery. In order to use a cathode material to deliver a higher energy density at a higher voltage platform, the hurdle of electrolyte decomposition should be addressed at least up to, or above, a redox potential of the cathode material.

Another problem with both organic carbonate-based electrolytes and other classes of electrolytes is chemical stability at elevated temperatures. Even at low voltages, elevated temperatures can cause conventional electrolytes to decompose by catalytic oxidation in the presence of cathode materials to produce undesirable products that affect both performance and safety of a battery.

It is against this background that a need arose to develop the electrolytes and related methods and systems described herein. Certain embodiments of the inventions disclosed herein address these and other challenges.

BRIEF SUMMARY

Certain embodiments of the invention are directed to a compound for use in an electrolyte and an electrolyte solution. The compound is represented by the formula (I):

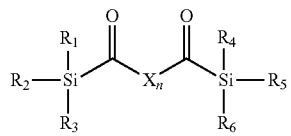

n is an integer from 1 to 20 and X is represented by the formula (II):

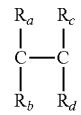

For each X of the n number of X's, $R_a$ is selected from the group consisting of substituted and unsubstituted $C_1$-$C_{20}$ alkenyl groups, $R_b$, is either not present or hydrogen, and $R_c$ and $R_d$ are each independently selected from the group consisting of substituted and unsubstituted $C_1$-$C_{20}$ alkyl groups, substituted and unsubstituted $C_1$-$C_{20}$ alkenyl groups, substituted and unsubstituted $C_1$-$C_{20}$ alkynyl groups, and substituted and unsubstituted $C_5$-$C_{20}$ aryl groups. X is selected from the group consisting of carbon, substituted and unsubstituted $C_3$-$C_{20}$ alkyl groups, substituted and unsubstituted $C_2$-$C_{20}$ alkenyl groups, and substituted and unsubstituted $C_4$-$C_{20}$ alkynyl groups. $R_1$, $R_2$, $R_3$, $R_4$, $R_5$, and $R_6$ are independently selected from the group consisting of substituted and unsubstituted $C_1$-$C_{20}$ alkyl groups, substituted and unsubstituted $C_1$-$C_{20}$ alkenyl groups, substituted and unsubstituted $C_1$-$C_{20}$ alkynyl groups, and substituted and unsubstituted $C_5$-$C_{20}$ aryl groups. In certain embodiments, he composition of claim 1 wherein the compound is represented by the formula (III):

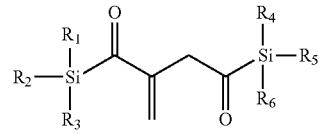

Certain embodiments of the invention are directed to an electrolyte solution including a salt, a solvent, and a compound represented by formula (I) and methods of making such an electrolyte solution. Certain embodiments of the invention are directed to an electrolyte solution including a salt, a solvent, and a compound represented by formula (III) and methods of making such an electrolyte solution.

Other embodiments of the invention are directed to methods of forming, conditioning, and operating a battery including such high voltage and high temperature electrolyte solutions. For example, methods of operating or using a battery can include providing the battery, and cycling such battery to supply power for consumer electronics, portable electronics, hybrid vehicles, electrical vehicles, power tools, power grid, military applications, and aerospace applications. For example, methods of forming a battery can include providing an anode, providing a cathode, and providing an electrolyte solution disposed between the anode and the cathode. The electrolyte can include an electrolyte solution of certain embodiments of the invention. The methods of forming the battery can also include cycling the battery to convert a stabilizing additive compound of the electrolyte into a derivative thereof.

Other aspects and embodiments of the invention are also contemplated. The foregoing summary and the following detailed description are not meant to restrict the invention to any particular embodiment but are merely meant to describe some embodiments of the invention.

DETAILED DESCRIPTION OF THE INVENTION

Figure 1:
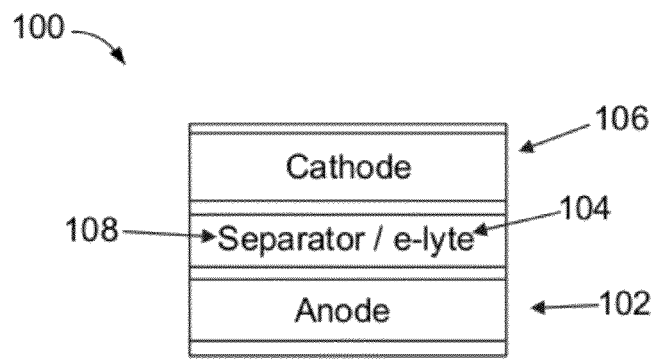
FIG. 1 illustrates a Li-ion battery implemented in accordance with an embodiment of the invention.

The following definitions apply to some of the aspects described with respect to some embodiments of the invention. These definitions may likewise be expanded upon herein. Each term is further explained and exemplified throughout the description, figures, and examples. Any interpretation of the terms in this description should take into account the full description, figures, and examples presented herein.

As used herein, the singular terms "a," "an," and "the" include the plural referents unless the context clearly dictates otherwise. Thus, for example, reference to an object can include multiple objects unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common characteristics.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the term "sub-micron range" refers to a general range of dimensions less than about 1 μm or less than about 1,000 nm, such as less than about 999 nm, less than about 900 nm, less than about 800 nm, less than about 700 nm, less than about 600 nm, less than about 500 nm, less than about 400 nm, less than about 300 nm, or less than about 200 nm, and down to about 1 nm or less. In some instances, the term can refer to a particular sub-range within the general range, such as from about 1 nm to about 100 nm, from about 100 nm to about 200 nm, from about 200 nm to about 300 nm, from about 300 nm to about 400 nm, from about 400 nm to about 500 nm, from about 500 nm to about 600 nm, from about 600 nm to about 700 nm, from about 700 nm to about 800 nm, from about 800 nm to about 900 nm, or from about 900 nm to about 999 nm.

As used herein, the term "main group element" refers to a chemical element in any of Group IA (or Group 1), Group IIA (or Group 2), Group IIIA (or Group 13), Group IVA (or Group 14), Group VA (or Group 15), Group VIA (or Group 16), Group VIIA (or Group 17), and Group VIIIA (or Group 18). A main group element is also sometimes referred to as a s-block element or a p-block element.

As used herein, the term "transition metal" refers to a chemical element in any of Group IVB (or Group 4), Group VB (or Group 5), Group VIB (or Group 6), Group VIIB (or Group 7), Group VIIIB (or Groups 8, 9, and 10), Group IB (or Group 11), and Group IIB (or Group 12). A transition metal is also sometimes referred to as a d-block element.

As used herein, the term "rare earth element" refers to any of Sc, Y, La, Ce, Pr, Nd, Pm, Sm, Eu, Gd, Tb, Dy, Ho, Er, Tm, Yb, and Lu.

As used herein, the term "halogen" refers to any of F, Cl, Br, I, and At.

As used herein, the term "chalcogen" refers to any of O, S, Se, Te, and Po.

As used herein, the term "heteroatom" refers to any atom that is not a carbon atom or a hydrogen atom. Examples of heteroatoms include atoms of halogens, chalcogens, Group IIIA (or Group 13) elements, Group IVA (or Group 14) elements other than carbon, and Group VA (or Group 15) elements.

As used herein, the term "alkane" refers to a saturated hydrocarbon, including the more specific definitions of "alkane" herein. For certain embodiments, an alkane can include from 1 to 100 carbon atoms. The term "lower alkane" refers to an alkane that includes from 1 to 20 carbon atoms, such as from 1 to 10 carbon atoms, while the term "upper alkane" refers to an alkane that includes more than 20 carbon atoms, such as from 21 to 100 carbon atoms. The term "branched alkane" refers to an alkane that includes one or more branches, while the term "unbranched alkane" refers to an alkane that is straight-chained. The term "cycloalkane" refers to an alkane that includes one or more ring structures. The term "heteroalkane" refers to an alkane that has one or more of its carbon atoms replaced by one or more heteroatoms, such as N, Si, S, O, F, and P. The term "substituted alkane" refers to an alkane that has one or more of its hydrogen atoms replaced by one or more substituent groups, such as halo groups, while the term "unsubstituted alkane" refers to an alkane that lacks such substituent groups. Combinations of the above terms can be used to refer to an alkane having a combination of characteristics. For example, the term "branched lower alkane" can be used to refer to an alkane that includes from 1 to 20 carbon atoms and one or more branches. Examples of alkanes include methane, ethane, propane, cyclopropane, butane, 2-methylpropane, cyclobutane, and charged, hetero, or substituted forms thereof.

As used herein, the term "alkyl group" refers to a monovalent form of an alkane, including the more specific definitions of "alkyl" herein. For example, an alkyl group can be envisioned as an alkane with one of its hydrogen atoms removed to allow bonding to another group. The term "lower alkyl group" refers to a monovalent form of a lower alkane, while the term "upper alkyl group" refers to a monovalent form of an upper alkane. The term "branched alkyl group" refers to a monovalent form of a branched alkane, while the term "unbranched alkyl group" refers to a monovalent form of an unbranched alkane. The term "cycloalkyl group" refers to a monovalent form of a cycloalkane, and the term "heteroalkyl group" refers to a monovalent form of a heteroalkane. The term "substituted alkyl group" refers to a monovalent form of a substituted alkane, while the term "unsubstituted alkyl group" refers to a monovalent form of an unsubstituted alkane. Examples of alkyl groups include methyl, ethyl, n-propyl, isopropyl, cyclopropyl, butyl, isobutyl, t-butyl, cyclobutyl, and charged, hetero, or substituted forms thereof.

As used herein, the term "alkylene group" refers to a bivalent form of an alkane, including the more specific definitions of "alkylene group" herein. For example, an alkylene group can be envisioned as an alkane with two of its hydrogen atoms removed to allow bonding to one or more additional groups. The term "lower alkylene group" refers to a bivalent form of a lower alkane, while the term "upper alkylene group" refers to a bivalent form of an upper alkane. The term "branched alkylene group" refers to a bivalent form of a branched alkane, while the term "unbranched alkylene group" refers to a bivalent form of an unbranched alkane. The term "cycloalkylene group" refers to a bivalent form of a cycloalkane, and the term "heteroalkylene group" refers to a bivalent form of a heteroalkane. The term "substituted alkylene group" refers to a bivalent form of a substituted alkane, while the term "unsubstituted alkylene group" refers to a bivalent form of an unsubstituted alkane. Examples of alkylene groups include methylene, ethylene, propylene, 2-methylpropylene, and charged, hetero, or substituted forms thereof.

As used herein, the term "alkene" refers to an unsaturated hydrocarbon that includes one or more carbon-carbon double bonds, including the more specific definitions of "alkene" herein. For certain embodiments, an alkene can include from 2 to 100 carbon atoms. The term "lower alkene" refers to an alkene that includes from 2 to 20 carbon atoms, such as from 2 to 10 carbon atoms, while the term "upper alkene" refers to an alkene that includes more than 20 carbon atoms, such as from 21 to 100 carbon atoms. The term "cycloalkene" refers to an alkene that includes one or more ring structures. The term "heteroalkene" refers to an alkene that has one or more of its carbon atoms replaced by one or more heteroatoms, such as N, Si, S, O, F, and P. The term "substituted alkene" refers to an alkene that has one or more of its hydrogen atoms replaced by one or more substituent groups, such as halo groups, while the term "unsubstituted alkene" refers to an alkene that lacks such substituent groups. Combinations of the above terms can be used to refer to an alkene having a combination of characteristics. For example, the term "substituted lower alkene" can be used to refer to an alkene that includes from 1 to 20 carbon atoms and one or more substituent groups. Examples of alkenes include ethene, propene, cyclopropene, 1-butene, trans-2 butene, cis-2-butene, 1,3-butadiene, 2-methylpropene, cyclobutene, and charged, hetero, or substituted forms thereof.

As used herein, the term "alkenyl group" refers to a monovalent form of an alkene, including the more specific definitions of "alkenyl group" herein. For example, an alkenyl group can be envisioned as an alkene with one of its hydrogen atoms removed to allow bonding to another group. The term "lower alkenyl group" refers to a monovalent form of a lower alkene, while the term "upper alkenyl group" refers to a monovalent form of an upper alkene. The term "cycloalkenyl group" refers to a monovalent form of a cycloalkene, and the term "heteroalkenyl group" refers to a monovalent form of a heteroalkene. The term "substituted alkenyl group" refers to a monovalent form of a substituted alkene, while the term "unsubstituted alkenyl group" refers to a monovalent form of an unsubstituted alkene. Examples of alkenyl groups include ethenyl, 2-propenyl (i.e., allyl), isopropenyl, cyclopropenyl, butenyl, isobutenyl, t-butenyl, cyclobutenyl, and charged, hetero, or substituted forms thereof.

As used herein, the term "alkenylene group" refers to a bivalent form of an alkene, including the more specific definitions of "alkenylene group" herein. For example, an alkenylene group can be envisioned as an alkene with two of its hydrogen atoms removed to allow bonding to one or more additional groups. The term "lower alkenylene group" refers to a bivalent form of a lower alkene, while the term "upper alkenylene group" refers to a bivalent form of an upper alkene. The term "cycloalkenylene group" refers to a bivalent form of a cycloalkene, and the term "heteroalkenylene group" refers to a bivalent form of a heteroalkene. The term "substituted alkenylene group" refers to a bivalent form of a substituted alkene, while the term "unsubstituted alkenylene group" refers to a bivalent form of an unsubstituted alkene. Examples of alkenyl groups include ethenylene, propenylene, 2-methylpropenylene, and charged, hetero, or substituted forms thereof.

As used herein, the term "alkyne" refers to an unsaturated hydrocarbon that includes one or more carbon-carbon triple bonds, including the more specific definitions of "alkyne" herein. In some embodiments, an alkyne can also include one or more carbon-carbon double bonds. For certain embodiments, an alkyne can include from 2 to 100 carbon atoms. The term "lower alkyne" refers to an alkyne that includes from 2 to 20 carbon atoms, such as from 2 to 10 carbon atoms, while the term "upper alkyne" refers to an alkyne that includes more than 20 carbon atoms, such as from 21 to 100 carbon atoms. The term "cycloalkyne" refers to an alkyne that includes one or more ring structures. The term "heteroalkyne" refers to an alkyne that has one or more of its carbon atoms replaced by one or more heteroatoms, such as N, Si, S, O, F, and P. The term "substituted alkyne" refers to an alkyne that has one or more of its hydrogen atoms replaced by one or more substituent groups, such as halo groups, while the term "unsubstituted alkyne" refers to an alkyne that lacks such substituent groups. Combinations of the above terms can be used to refer to an alkyne having a combination of characteristics. For example, the term "substituted lower alkyne" can be used to refer to an alkyne that includes from 1 to 20 carbon atoms and one or more substituent groups. Examples of alkynes include ethyne (i.e., acetylene), propyne, 1-butyne, 1-buten-3-yne, 1-pentyne, 2-pentyne, 3-penten-1-yne, 1-penten-4-yne, 3-methyl-1-butyne, and charged, hetero, or substituted forms thereof.

As used herein, the term "alkynyl group" refers to a monovalent form of an alkyne, including the more specific definitions of "alkynyl group" herein. For example, an alkynyl group can be envisioned as an alkyne with one of its hydrogen atoms removed to allow bonding to another group. The term "lower alkynyl group" refers to a monovalent form of a lower alkyne, while the term "upper alkynyl group" refers to a monovalent form of an upper alkyne. The term "cycloalkynyl group" refers to a monovalent form of a cycloalkyne, and the term "heteroalkynyl group" refers to a monovalent form of a heteroalkyne. The term "substituted alkynyl group" refers to a monovalent form of a substituted alkyne, while the term "unsubstituted alkynyl group" refers to a monovalent form of an unsubstituted alkyne. Examples of alkynyl groups include ethynyl, propynyl, isopropynyl, butynyl, isobutynyl, t-butynyl, and charged, hetero, or substituted forms thereof.

As used herein, the term "alkynylene group" refers to a bivalent form of an alkyne, including the more specific definitions of "alkynylene group" herein. For example, an alkynylene group can be envisioned as an alkyne with two of its hydrogen atoms removed to allow bonding to one or more additional groups of a molecule. The term "lower alkynylene group" refers to a bivalent form of a lower alkyne, while the term "upper alkynylene group" refers to a bivalent form of an upper alkyne. The term "cycloalkynylene group" refers to a bivalent form of a cycloalkyne, and the term "heteroalkynylene group" refers to a bivalent form of a heteroalkyne. The term "substituted alkynylene group" refers to a bivalent form of a substituted alkyne, while the term "unsubstituted alkynylene group" refers to a bivalent form of an unsubstituted alkyne. Examples of alkynylene groups include ethynylene, propynylene, 1-butynylene, 1-buten-3-ynylene, and charged, hetero, or substituted forms thereof.

As used herein, the term "arene" refers to an aromatic hydrocarbon, including the more specific definitions of "arene" herein. For certain embodiments, an arene can include from 5 to 100 carbon atoms. The term "lower arene" refers to an arene that includes from 5 to 20 carbon atoms, such as from 5 to 14 carbon atoms, while the term "upper arene" refers to an arene that includes more than 20 carbon atoms, such as from 21 to 100 carbon atoms. The term "monocyclic arene" refers to an arene that includes a single aromatic ring structure, while the term "polycyclic arene" refers to an arene that includes more than one aromatic ring structure, such as two or more aromatic ring structures that are bonded via a carbon-carbon bond or that are fused together. The term "heteroarene" refers to an arene that has one or more of its carbon atoms replaced by one or more heteroatoms, such as N, Si, S, O, F, and P. The term "substituted arene" refers to an arene that has one or more of its hydrogen atoms replaced by one or more substituent groups, such as alkyl groups, alkenyl groups, alkynyl groups, halo groups, hydroxy groups, alkoxy groups, alkenoxy groups, alkynoxy groups, aryloxy groups, carboxy groups, cyano groups, nitro groups, amino groups, N-substituted amino groups, silyl groups, and siloxy groups, while the term "unsubstituted arene" refers to an arene that lacks such substituent groups. Combinations of the above terms can be used to refer to an arene having a combination of characteristics. For example, the term "monocyclic lower alkene" can be used to refer to an arene that includes from 5 to 20 carbon atoms and a single aromatic ring structure. Examples of arenes include benzene, biphenyl, naphthalene, anthracene, pyridine, pyridazine, pyrimidine, pyrazine, quinoline, isoquinoline, and charged, hetero, or substituted forms thereof.

As used herein, the term "aryl group" refers to a monovalent form of an arene, including the more specific definitions of "aryl group" herein. For example, an aryl group can be envisioned as an arene with one of its hydrogen atoms removed to allow bonding to another group. The term "lower aryl group" refers to a monovalent form of a lower arene, while the term "upper aryl group" refers to a monovalent form of an upper arene. The term "monocyclic aryl group" refers to a monovalent form of a monocyclic arene, while the term "polycyclic aryl group" refers to a monovalent form of a polycyclic arene. The term "heteroaryl group" refers to a monovalent form of a heteroarene. The term "substituted aryl group" refers to a monovalent form of a substituted arene, while the term "unsubstituted arene group" refers to a monovalent form of an unsubstituted arene. Examples of aryl groups include phenyl, biphenylyl, naphthyl, pyridinyl, pyridazinyl, pyrimidinyl, pyrazinyl, quinolyl, isoquinolyl, and charged, hetero, or substituted forms thereof.

As used herein, the term "imine" refers to an organic compound that includes one or more carbon-nitrogen double bonds, including the more specific definitions of "imine" herein. For certain embodiments, an imine can include from 1 to 100 carbon atoms. The term "lower imine" refers to an imine that includes from 1 to 20 carbon atoms, such as from 1 to 10 carbon atoms, while the term "upper imine" refers to an imine that includes more than carbon atoms, such as from 21 to 100 carbon atoms. The term "cycloimine" refers to an imine that includes one or more ring structures. The term "heteroimine" refers to an imine that has one or more of its carbon atoms replaced by one or more heteroatoms, such as N, Si, S, O, F, and P. The term "substituted imine" refers to an imine that has one or more of its hydrogen atoms replaced by one or more substituent groups, such as halo groups, while the term "unsubstituted imine" refers to an imine that lacks such substituent groups. Combinations of the above terms can be used to refer to an imine having a combination of characteristics. For example, the term "substituted lower imine" can be used to refer to an imine that includes from 1 to 20 carbon atoms and one or more substituent groups. Examples of imines include $R_1CH=NR_2$, where $R_1$ and $R_2$ are independently selected from hydride groups, alkyl groups, alkenyl groups, and alkynyl groups.

As used herein, the term "iminyl group" refers to a monovalent form of an imine, including the more specific definitions of "iminyl" herein. For example, an iminyl group can be envisioned as an imine with one of its hydrogen atoms removed to allow bonding to another group. The term "lower iminyl group" refers to a monovalent form of a lower imine, while the term "upper iminyl group" refers to a monovalent form of an upper imine. The term "cycloiminyl group" refers to a monovalent form of a cycloimine, and the term "heteroiminyl group" refers to a monovalent form of a heteroimine. The term "substituted iminyl group" refers to a monovalent form of a substituted imine, while the term "unsubstituted iminyl group" refers to a monovalent form of an unsubstituted imine. Examples of iminyl groups include $—R_1CH=NR_2$, $R_3CH=NR_4—$, $—CH=NR_5$, and $R_6CH=N—$, where $R_1$ and $R_4$ are independently selected from alkylene groups, alkenylene groups, and alkynylene groups, and $R_2$, $R_3$, $R_5$, and $R_6$ are independently selected from hydride groups, alkyl groups, alkenyl groups, and alkynyl groups.

As used herein, the term "alcohol" refers to an organic compound that includes one or more hydroxy groups. For certain embodiments, an alcohol can also be referred to as a substituted hydrocarbon, such as a substituted arene that has one or more of its hydrogen atoms replaced by one or more hydroxy groups. Examples of alcohols include ROH, where R is selected from alkyl groups, alkenyl groups, alkynyl groups, and aryl groups.

As used herein, the term "ketone" refers to a molecule that includes one or more groups of the form: —CO—. Examples of ketones include $R_1—CO—R_2$, where $R_1$ and $R_2$ are independently selected from alkyl groups, alkenyl groups, alkynyl groups, and aryl groups, and $R_3—CO—R_4—CO—R_5$, where $R_3$ and $R_5$ are independently selected from alkyl groups, alkenyl groups, alkynyl groups, and aryl groups, and $R_4$ is selected from alkylene groups, alkenylene groups, and alkynylene groups.

As used herein, the term "carboxylic acid" refers to an organic compound that includes one or more carboxy groups. For certain embodiments, a carboxylic acid can also be referred to as a substituted hydrocarbon, such as a substituted arene that has one or more of its hydrogen atoms replaced by one or more carboxy groups. Examples of carboxylic acids include RCOOH, where R is selected from alkyl groups, alkenyl groups, alkynyl groups, and aryl groups.

As used herein, the term "hydride group" refers to —H.

As used herein, the term "halo group" refers to —X, where X is a halogen. Examples of halo groups include fluoro, chloro, bromo, and iodo.

As used herein, the term "hydroxy group" refers to —OH.

As used herein, the term "alkoxy group" refers to —OR, where R is an alkyl group.

As used herein, the term "alkenoxy group" refers to —OR, where R is an alkenyl group.

As used herein, the term "alkynoxy group" refers to —OR, where R is an alkynyl group.

As used herein, the term "aryloxy group" refers to —OR, where R is an aryl group.

As used herein, the term "carboxy group" refers to —COOH.

As used herein, the term "alkylcarbonyloxy group" refers to RCOO—, where R is an alkyl group.

As used herein, the term "alkenylcarbonyloxy group" refers to RCOO—, where R is an alkenyl group.

As used herein, the term "alkynylcarbonyloxy group" refers to RCOO—, where R is an alkynyl group.

As used herein, the term "arylcarbonyloxy group" refers to RCOO—, where R is an aryl group.

As used herein, the term "thio group" refers to —SH.

As used herein, the term "alkylthio group" refers to —SR, where R is an alkyl group.

As used herein, the term "alkenylthio group" refers to —SR, where R is an alkenyl group.

As used herein, the term "alkynylthio group" refers to —SR, where R is an alkynyl group.

As used herein, the term "arylthio group" refers to —SR, where R is an aryl group.

As used herein, the term "cyano group" refers to —CN.

As used herein, the term "nitro group" refers to —$NO_2$.

As used herein, the term "amino group" refers to —$NH_2$.

As used herein, the term "N-substituted amino group" refers to an amino group that has one or more of its hydrogen atoms replaced by one or more substituent groups. Examples of N-substituted amino groups include —$NR_1R_2$, where $R_1$ and $R_2$ are independently selected from hydride groups, alkyl groups, alkenyl groups, alkynyl groups, and aryl groups, and at least one of $R_1$ and $R_2$ is not a hydride group.

As used herein, the term "alkylcarbonylamino group" refers to —NHCOR, where R is an alkyl group.

As used herein, the term "N-substituted alkylcarbonylamino group" refers to an alkylcarbonylamino group that has its hydrogen atom replaced by a substituent group. Examples of N-substituted alkylcarbonylamino groups include —$NR_1COR_2$, where $R_1$ is selected from alkyl groups, alkenyl groups, alkynyl groups, and aryl groups, and $R_2$ is an alkyl group.

As used herein, the term "alkenylcarbonylamino group" refers to —NHCOR, where R is an alkenyl group.

As used herein, the term "N-substituted alkenylcarbonylamino group" refers to an alkenylcarbonylamino group that has its hydrogen atom replaced by a substituent group. Examples of N-substituted alkenylcarbonylamino groups include —$NR_1COR_2$, where $R_1$ is selected from alkyl groups, alkenyl groups, alkynyl groups, and aryl groups, and $R_2$ is an alkenyl group.

As used herein, the term "alkynylcarbonylamino group" refers to —NHCOR, where R is an alkynyl group.

As used herein, the term "N-substituted alkynylcarbonylamino group" refers to an alkynylcarbonylamino group that has its hydrogen atom replaced by a substituent group. Examples of N-substituted alkynylcarbonylamino groups include —$NR_1COR_2$, where $R_1$ is selected from alkyl groups, alkenyl groups, alkynyl groups, and aryl groups, and $R_2$ is an alkynyl group.

As used herein, the term "arylcarbonylamino group" refers to —NHCOR, where R is an aryl group.

As used herein, the term "N-substituted arylcarbonylamino group" refers to an arylcarbonylamino group that has its hydrogen atom replaced by a substituent group. Examples of N-substituted arylcarbonylamino groups include —$NR_1COR_2$, where $R_1$ is selected from alkyl groups, alkenyl groups, alkynyl groups, and aryl groups, and $R_2$ is an aryl group.

As used herein, the term "silyl group" refers to —$SiR_1R_2R_3$, where $R_1$, $R_2$, and $R_3$ are independently selected from, for example, hydride groups, alkyl groups, alkenyl groups, alkynyl groups, and aryl groups.

As used herein, the term "siloxy group" refers to —$OSiR_1R_2R_3$, where $R_1$, $R_2$, and $R_3$ are independently selected from, for example, hydride groups, alkyl groups, alkenyl groups, alkynyl groups, and aryl groups.

As used herein, the term "ether linkage" refers to —O—.

As used herein, the term "specific capacity" refers to the amount (e.g., total or maximum amount) of electrons or lithium ions a material is able to hold (or discharge) per unit mass and can be expressed in units of mAh/g. In certain aspects and embodiments, specific capacity can be measured in a constant current discharge (or charge) analysis which includes discharge (or charge) at a defined rate over a defined voltage range against a defined counterelectrode. For example, specific capacity can be measured upon discharge at a rate of about 0.05 C (e.g., about 7.5 mA/g) from 4.95 V to 2.0 V versus a Li/Li$^+$ counterelectrode. Other discharge rates and other voltage ranges also can be used, such as a rate of about 0.1 C (e.g., about 15 mA/g), or about 0.5 C (e.g., about 75 mA/g), or about 1.0 C (e.g., about 150 mA/g).

As used herein, a rate "C" refers to either (depending on context) the discharge current as a fraction or multiple relative to a "1 C" current value under which a battery (in a substantially fully charged state) would substantially fully discharge in one hour, or the charge current as a fraction or multiple relative to a "1 C" current value under which the battery (in a substantially fully discharged state) would substantially fully charge in one hour.

As used herein, the terms "cycle" or "cycling" refer to complementary discharging and charging processes.

As used herein, the term "rated charge voltage" refers to an upper end of a voltage range during operation of a battery, such as a maximum voltage during charging, discharging, and/or cycling of the battery. In some aspects and some embodiments, a rated charge voltage refers to a maximum voltage upon charging a battery from a substantially fully discharged state through its (maximum) specific capacity at an initial cycle, such as the $1^{st}$ cycle, the $2^{nd}$ cycle, or the $3^{rd}$ cycle. In some aspects and some embodiments, a rated charge voltage refers to a maximum voltage during operation of a battery to substantially maintain one or more of its performance characterics, such as one or more of coulombic efficiency, retention of specific capacity, retention of energy density, and rate capability.

As used herein, the term "rated cut-off voltage" refers to a lower end of a voltage range during operation of a battery, such as a minimum voltage during charging, discharging, and/or cycling of the battery. In some aspects and some embodiments, a rated cut-off voltage refers to a minimum voltage upon discharging a battery from a substantially fully charged state through its (maximum) specific capacity at an initial cycle, such as the $1^{st}$ cycle, the $2^{nd}$ cycle, or the $3^{rd}$ cycle, and, in such aspects and embodiments, a rated cut-off voltage also can be referred as a rated discharge voltage. In some aspects and some embodiments, a rated cut-off voltage refers to a minimum voltage during operation of a battery to substantially maintain one or more of its performance characterics, such as one or more of coulombic efficiency, retention of specific capacity, retention of energy density, and rate capability.

As used herein, the "maximum voltage" refers to the voltage at which both the anode and the cathode are fully charged. In an electrochemical cell, each electrode may have a given specific capacity and one of the electrodes will be the limiting electrode such that one electrode will be fully charged and the other will be as fully charged as it can be for that specific pairing of electrodes. The process of matching the specific capacities of the electrodes to achieve the desired capacity of the electrochemical cell is "capacity matching."

To the extent certain battery characteristics can vary with temperature, such characteristics are specified at room temperature (25° C.), unless the context clearly dictates otherwise.

Certain embodiments of the invention relate to electrolyte solutions that provide a number of desirable characteristics when implemented within batteries, such as high stability during battery cycling to high voltages at or above 4.2 V, high specific capacity upon charge or discharge, high coulombic efficiency, excellent retention of specific capacity and energy density over several cycles of charging and discharging, high rate capability, reduced electrolyte decomposition, reduced resistance and its build-up during cycling, and improved calendar life. The electrolyte solutions provide these performance characteristics over a wide range of operational temperatures, encompassing about −40° C. or less and up to about 60° C., up to about 80° C., or more. In some embodiments, these performance characteristics can at least partially derive from the presence of a set of additives or compounds, which can impart high voltage and high temperature stability to an electrolyte while retaining or improving battery performance.

For example, in terms of their stability, electrolytes that include compounds according to some embodiments of the invention can undergo little or no decomposition (beyond any initial decomposition related to film formation at battery electrodes or as part of initial cycling) when batteries incorporating the electrolytes are cycled at least up to a redox potential of a high voltage cathode material, such as at least about 4.2 V or about 4.5 V and up to about 4.95 V, up to about 5 V, up to about 5.5 V, up to about 6 V or more, as measured relative to a lithium metal anode (Li/Li$^+$ anode). These voltages may vary for other counterelectrodes, but the improved performance is retained according to some embodiments. Such reduction in electrolyte decomposition, in turn, yields one or more of the following benefits: (1) mitigation against loss of electrolyte; (2) mitigation against the production of undesirable by-products that can affect battery performance; (3) mitigation against the production of gaseous by-products that can affect battery safety; and (4) reduced resistance and its build-up during cycling.

Also, batteries incorporating the electrolyte solutions including compounds according to certain embodiments can exhibit high coulombic efficiency, as expressed in terms of a ratio of a specific capacity upon discharge to a specific capacity upon charge for a given cycle. As measured upon cycling at a rate of 1 C (or another reference rate higher or lower than 1 C, such as 0.1 C, 0.05 C, 0.5 C, 5 C, or 10 C), batteries incorporating the improved electrolytes can have a coulombic efficiency at the 1$^{st}$ cycle (or another initial cycle, such as the 2$^{nd}$ cycle, the 3$^{rd}$ cycle, the 4$^{th}$ cycle, the 5$^{th}$ cycle, the 6$^{th}$ cycle, the 7$^{th}$ cycle, the 8$^{th}$ cycle, the 9$^{th}$ cycle, or the 10$^{th}$ cycle) or an average coulombic efficiency over an initial set of cycles, such as cycles 1 through 3, cycles 1 through 5, cycles 3 through 10, cycles 5 through 10, or cycles 5 through 15, that is at least about 60%, such as at least about 70%, at least about 80%, at least about 90%, or at least about 95%, and up to about 97%, up to about 98%, up to about 99%, up to about 99.8%, up to about 99.9%, up to about 99.99%, up to about 99.999%, or more. Stated in another way, and as measured upon cycling at a substantially constant current of 150 mA/g (or another reference current higher or lower than 150 mA/g, such as 15 mA/g, 7.5 mA/g, 75 mA/g, 750 mA/g, or 1,500 mA/g), batteries incorporating the electrolyte solutions including compounds of certain embodiments can have a coulombic efficiency at the 1$^{st}$ cycle (or another initial cycle, such as the 2$^{nd}$ cycle, the 3$^{rd}$ cycle, the 4$^{th}$ cycle, the 5$^{th}$ cycle, the 6$^{th}$ cycle, the 7$^{th}$ cycle, the 8$^{th}$ cycle, the 9$^{th}$ cycle, or the 10$^{th}$ cycle) or an average coulombic efficiency over an initial set of cycles, such as cycles 1 through 3, cycles 1 through 5, cycles 3 through 10, cycles 5 through 10, or cycles 5 through 15, that is at least about 60%, such as at least about 70%, at least about 80%, at least about 90%, or at least about 95%, and up to about 97%, up to about 98%, up to about 99%, up to about 99.8%, up to about 99.9%, up to about 99.99%, up to about 99.999%, or more. The stated values for current can be per unit mass of a cathode active material, and can be expressed in units of mA/(g of the cathode active material).

In addition, batteries incorporating the electrolyte solutions including compounds of certain embodiments can exhibit excellent capacity retention defined in terms of a specific capacity (both upon charge and upon discharge) over several charging and discharging cycles, such that, after 100 cycles, after 200 cycles, after 300 cycles, after 400 cycles, after 500 cycles, after 600 cycles, after 1,000 cycles, or even after 5,000 cycles from an initial cycle, at least about 50%, at least about 60%, at least about 70%, at least about 75%, at least about 80%, or at least about 85%, and up to about 90%, up to about 95%, up to about 98%, or more of an initial or maximum specific capacity at the 1$^{st}$ cycle (or another initial cycle, such as the 2$^{nd}$ cycle, the 3$^{rd}$ cycle, the 4$^{th}$ cycle, the 5$^{th}$ cycle, the 6$^{th}$ cycle, the 7$^{th}$ cycle, the 8$^{th}$ cycle, the 9$^{th}$ cycle, or the 10$^{th}$ cycle) is retained, as measured upon cycling at a rate of 1 C (or another reference rate higher or lower than 1 C, such as 0.1 C, 0.05 C, 0.5 C, 5 C, or 10 C) or upon cycling at a substantially constant current of 150 mA/g (or another reference current higher or lower than 150 mA/g, such as 15 mA/g, 7.5 mA/g, 75 mA/g, 750 mA/g, or 1,500 mA/g). The stated values for current can be per unit mass of a cathode active material, and can be expressed in units of mA/(g of the cathode active material).

In addition, batteries incorporating the electrolyte solutions including compounds of certain embodiments can exhibit excellent efficiency retention defined in terms of a coulombic efficiency over several charging and discharging cycles, such that, after 100 cycles, after 200 cycles, after 300 cycles, after 400 cycles, after 500 cycles, after 600 cycles, after 1,000 cycles, or even after 5,000 cycles from an initial cycle, at least about 70%, at least about 80%, at least about 90%, or at least about 95%, and up to about 97%, up to about 98%, up to about 99%, up to about 99.9%, or more of an initial or maximum coulombic efficiency at the 1$^{st}$ cycle (or another initial cycle, such as the 2$^{nd}$ cycle, the 3$^{th}$ cycle, the 4$^{th}$ cycle, the 5 cycle, the 6$^{th}$ cycle, the 7$^{th}$ cycle, the 8$^{th}$ cycle, the 9$^{th}$ cycle, or the 10 cycle) is retained, as measured upon cycling at a rate of 1 C (or another reference rate higher or lower than 1 C, such as 0.1 C, 0.05 C, 0.5 C, 5 C, or 10 C) or upon cycling at a substantially constant current of 150 mA/g (or another reference current higher or lower than 150 mA/g, such as 15 mA/g, 7.5 mA/g, 75 mA/g, 750 mA/g, or 1,500 mA/g). The stated values for current can be per unit mass of a cathode active material, and can be expressed in units of mA/(g of the cathode active material).

In terms of rate capability or power performance, batteries incorporating the electrolyte solutions including compounds of certain embodiments can exhibit excellent rate capability defined in terms of retention of specific capacity (both upon charge and upon discharge) when charged, discharged, or cycled at higher rates, such that, as measured at a high rate of 1 C (or another high rate that is n times a reference, low rate, with n>1 such as n=5, n=10, n=20, or n=100), at least about 60%, at least about 70%, at least about 75%, at least about 80%, at least about 85%, at least about 90%, or at least about 95%, and up to about 99%, up to about 99.5%, up to about 99.9%, or more of a low rate or maximum specific capacity at a rate of 0.05 C (or another reference rate higher or lower than 0.05 C, such as 0.1 C) is retained. Stated in another way, batteries incorporating the electrolyte solutions including compounds of certain embodiments can exhibit excellent retention of specific capacity (both upon charge and upon discharge) when charged, discharged, or cycled at higher currents, such that, as measured at a substantially constant current of 150 mA/g (or another current that is n times a reference current, with n>1 such as n=5, n=10, n=20, or n=100), at least about 60%, at least about 70%, at least about 75%, at least about 80%, at least about 85%, at least about 90%, or at least about 95%, and up to about 99%, up to about 99.5%, up to about 99.9%, or more of a low rate or maximum specific capacity at a substantially constant current of 7.5 mA/g (or another reference current higher or lower than 7.5 mA/g, such as 15 mA/g) is retained. The stated values for current can be per unit mass of a cathode active material, and can be expressed in units of mA/(g of the cathode active material).

Likewise, batteries incorporating the electrolyte solutions including compounds of certain embodiments can exhibit excellent rate capability defined in terms of retention of energy density when cycled at higher rates, such that, as measured at a rate of 1 C (or another rate that is n times a reference rate, with n>1 such as n=5, n=10, n=20, or n=100), at least about 60%, at least about 70%, at least about 75%, at least about 80%, at least about 85%, at least about 90%, or at least about 95%, and up to about 99%, up to about 99.5%, up to about 99.9%, or more of a low rate or maximum coulombic efficiency at a rate of 0.05 C (or another reference rate higher or lower than 0.05 C, such as 0.1 C) is retained. Stated in another way, batteries incorporating the electrolyte solutions including compounds of certain embodiments can exhibit excellent retention of energy density when cycled at higher currents, such that, as measured at a substantially constant current of 150 mA/g (or another current that is n times a reference current, with n>1 such as n=5, n=10, n=20, or n=100), at least about 60%, at least about 70%, at least about 75%, at least about 80%, at least about 85%, at least about 90%, or at least about 95%, and up to about 99%, up to about 99.5%, up to about 99.9%, or more of a low rate or maximum coulombic efficiency at a substantially constant current of 7.5 mA/g (or another reference current higher or lower than 7.5 mA/g, such as 15 mA/g) is retained. The stated values for current can be per unit mass of a cathode active material, and can be expressed in units of mA/(g of the cathode active material).

In addition, batteries incorporating the electrolyte solutions including compounds of certain embodiments can have a reduced resistance and a reduced resistance build-up during cycling. Such reduced resistance, in turn, yields one or more of the following benefits: (1) efficient removal of Li ions from electrodes; (2) higher specific capacity and higher energy density; (3) reduced hysteresis in a voltage profile between charging and discharging; and (4) mitigation against temperature increase during cycling.

Advantageously, the electrolyte solutions including compounds of certain embodiments can provide these performance characteristics over a wide range of operational temperatures, such as when batteries incorporating the electrolyte solutions including compounds of certain embodiments are charged, discharged, or cycled from about −40° C. to about 80° C., from about −40° C. to about 60° C., from about −40° C. to about 25° C., from about −40° C. to about 0° C., from about 0° C. to about 60° C., from about 0° C. to about 25° C., from about 25° C. to about 60° C., or other ranges encompassing temperatures greater than or below 25° C. The improved electrolytes also can provide these performance characteristics over a wide range of operational voltages between a rated cut-off voltage and a rated charge voltage, such as when the batteries are charged, discharged, or cycled between voltage ranges encompassing about 2 V to about 4.2 V, about 2 V to about 4.3 V, about 2 V to about 4.5 V, about 2 V to about 4.6 V, about 2 V to about 4.7 V, about 2 V to about 4.95 V, about 3 V to about 4.2 V, about 3 V to about 4.3 V, about 3 V to about 4.5 V, about 3 V to about 4.6 V, about 3 V to about 4.7 V, about 3 V to about 4.9 V, about 2 V to about 6 V, about 3 V to about 6 V, about 4.2 V to about 6 V, about 4.5 V to about 6 V, about 2 V to about 5.5 V, about 3 V to about 5.5 V, about 4.5 V to about 5.5 V, about 2 V to about 5 V, about 3 V to about 5 V, about 4.5 V to about 5 V, or about 5 V to about 6 V, as measured relative to a lithium metal anode (Li/Li anode). Stated in another way, the batteries incorporating the electrolyte solutions including compounds of certain embodiments have a rated charge voltage of at least about 4.2 V, at least about 4.3 V, at least about 4.5 V, at least about 4.6 V, at least about 4.7 V, or at least about 5 V, and up to about 5.5 V, up to about 6 V or more, as measured relative to anodes included within the batteries and upon charging at a rate of 1 C (or another reference rate higher or lower than 1 C, such as 0.1 C, 0.05 C, 0.5 C, 5 C, or 10 C) or upon charging at a substantially constant current of 150 mA/g (or another reference current higher or lower than 150 mA/g, such as 15 mA/g, 7.5 mA/g, 75 mA/g, 750 mA/g, or 1,500 mA/g). The batteries can be charged to the rated charge voltage while substantially retaining the performance characteristics specified above, such as in terms of coulombic efficiency, retention of specific capacity, retention of coulombic efficiency, and rate capability.

A high voltage electrolyte according to some embodiments of the invention can be formed with reference to the formula:

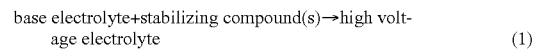
base electrolyte+stabilizing compound(s)→high voltage electrolyte  (1)

A high temperature electrolyte according to some embodiments of the invention can be formed with reference to the formula:

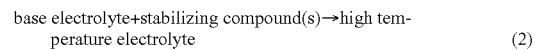
base electrolyte+stabilizing compound(s)→high temperature electrolyte  (2)

In formulas (1) and (2), the base electrolyte can include a set of solvents and a set of salts, such as a set of Li-containing salts in the case of Li-ion batteries. Examples of suitable solvents include nonaqueous electrolyte solvents for use in Li-ion batteries, including carbonates, such as ethylene carbonate, dimethyl carbonate, ethyl methyl carbonate, propylene carbonate, methyl propyl carbonate, and diethyl carbonate; sulfones; silanes; nitriles; esters; ethers; and combinations thereof. Additional examples of suitable solvents include those discussed in Xu et al., "Sulfone-based Electrolytes for Lithium-Ion Batteries," *Journal of the Electrochemical Society*, 149 (7) A920-A926 (2002); and Nagahama et al., "High Voltage Performances of $Li_2NiPO_4F$ Cathode with Dinitrile-Based Electrolytes," *Journal of the Electrochemical Society*, 157 (6) A748-A752 (2010); the disclosures of which are incorporated herein by reference in their entirety. Examples of suitable salts include Li-containing salts for use in Li-ion batteries, such as lithium hexafluorophosphate ("$LiPF_6$"), lithium perchlorate ("$LiClO_4$"), lithium tetrafluoroborate ("$LiBF_4$"), lithium trifluoromethane sulfonate ("$LiCF_3SO_3$"), lithium bis(trifluoromethane sulfonyl) imide ("$LiN(CF_3SO_2)_2$"), lithium bis (perfluoroethyl sulfonyl) imide ("$LiN(CF_3CF_2SO_2)_2$"), lithium bis(oxalato)borate ("$LiB(C_2O_4)_2$"), lithium difluoro oxalato borate ("LiF$_2$BC$_2$O$_4$"), and combinations thereof. Other suitable solvents and salts can be used to yield high voltage and high temperature electrolytes having low electronic conductivity, high Li ion solubility, low viscosity, high thermal stability, and other desirable characteristics.

In formulas (1) and (2), the stabilizing compound(s) is a set of additives that can correspond to a single additive, a pair of different additives, or a combination of three or more different additives. Examples of suitable stabilizing additives include silicon-containing compounds, such as silanes, siloxanes, and other organosilicon compounds including a SiX$_4$ moiety or a SiR$_3$ moiety. One or more of the stabilizing additives described herein can be used in combination with one or more conventional additives to impart improved performance characteristics.

Examples of suitable silicon-containing compounds include silanes represented with reference to the formula:

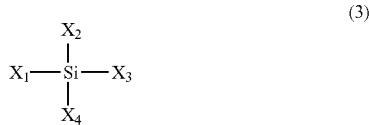

(3)

In formula (3), X$_1$, X$_2$, X$_3$, and X$_4$ can be the same or different, and, in some embodiments, at least one of X$_1$, X$_2$, X$_3$, and X$_4$ is an organic group including from 1 to 20 carbon atoms. For other embodiments, at least one of X$_1$, X$_2$, X$_3$, and X$_4$ is an organic group including more than carbon atoms. X$_1$, X$_2$, X$_3$, and X$_4$ can be independently selected from, for example, hydride group, halo groups, hydroxy group, thio group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, N-substituted arylcarbonylamino groups, boron-containing groups, aluminum-containing groups, silicon-containing groups (e.g., silyl groups and siloxy groups), phosphorus-containing groups, and sulfur-containing groups.

Examples of suitable silane compounds include, but are not limited to: 1,2-Bis(chlorodimethylsilyl)ethane, Bis(trimethylsilylmethyl)sulfide, Tetrakis(trimethylsilyl)silane, Tetraethylsilane, 4-(Trimethylsilyl)-3-butyn-2-one, Trivinylmethylsilane, Dimethyldichlorosilane, Hexamethyldisilane, Tris(trimethylsilyl)silane, Vinyl(trifluoromethyl)dimethylsilane, Tetravinylsilane, 1,3-Bis[(trimethylsilyl)ethynyl]benzene, 1,2-Bis(methyldifluorosilyl)ethane, 2,2-Bis-(trimethylsilyl)dithiane, Phenyltrimethoxysilane, Pentafluorophenyltriethoxysilane, and combinations thereof.

According to certain embodiments, suitable silicon-containing compounds according to formula (3) include compounds where at least one of X$_1$, X$_2$, X$_3$, and X$_4$ includes a nitrogen atom or group. X$_1$, X$_2$, X$_3$, and X$_4$ can be the same or different, and, in some embodiments, at least one of X$_1$, X$_2$, X$_3$, and X$_4$ is an organic group including from 1 to 20 carbon atoms. For other embodiments, at least one of X$_1$, X$_2$, X$_3$, and X$_4$ is an organic group including more than 20 carbon atoms. In some embodiments, at least one of X$_1$, X$_2$, X$_3$, and X$_4$ includes an ether linkage, and, in other embodiments, at least one of X$_1$, X$_2$, X$_3$, and X$_4$ includes a silicon atom or another heteroatom. X$_1$, X$_2$, X$_3$, and X$_4$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, N-substituted arylcarbonylamino groups, and heterocycle groups.

In certain preferred embodiments, X$_1$, X$_2$, and X$_3$ are alkyl groups, and in particular methyl groups. In certain preferred embodiments where each of X$_1$, X$_2$, and X$_3$ are methyl groups, these silicon-containing compounds are referred to as NTMS compounds after the silicon-nitrogen bond ("N") and the trimethylsilyl ("TMS") provided by each of X$_1$, X$_2$, and X$_3$ being methyl groups. As described in more detail below, NTMS compounds exhibit desirable properties as additives according to certain embodiments of the invention.

Examples of suitable NTMS compounds include, but are not limited to: Bis(trimethylsilyl)carbodiimide, Trimethylsilylazide, Bis(trimethylsilyl)urea, N,O-Bis(trimethylsilyl)trifluoroacetamide, N,O-Bis(trimethylsilyl)acetamide, (N,N-Dimethylamino)triethylsilane, Methylsilatrane, Trimethylsilyl isocyanate, Tetraisocyanatosilane, 1-Trimethylsilyl-1,2,4-triazole, 2-(Trimethylsilyl)thiazole, Heptamethyldisilazane, and combinations thereof.

According to certain embodiments, suitable silicon-containing compounds according to formula (3) include compounds where at least one of X$_1$, X$_2$, X$_3$, and X$_4$ includes a carbon atom or group. X$_1$, X$_2$, X$_3$, and X$_4$ can be the same or different, and, in some embodiments, at least one of X, X$_2$, X$_3$, and X$_4$ is an organic group including from 1 to 20 carbon atoms. For other embodiments, at least one of X$_1$, X$_2$, X$_3$, and X$_4$ is an organic group including more than 20 carbon atoms. In some embodiments, at least one of X, X$_2$, X$_3$, and X$_4$ includes an ether linkage, and, in other embodiments, at least one of X$_1$, X$_2$, X$_3$, and X$_4$ includes a silicon atom or another heteroatom. X$_1$, X$_2$, X$_3$, and X$_4$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, N-substituted arylcarbonylamino groups, and heterocycle groups.

In certain preferred embodiments, X, X$_2$, and X$_3$ are alkyl groups, and in particular methyl groups. In certain preferred embodiments where each of X$_1$, X$_2$, and X$_3$ are methyl groups, these silicon-containing compounds are referred to as CTMS compounds after the silicon-carbon bond ("C") and the trimethylsilyl ("TMS") provided by each of X$_1$, X$_2$, and X$_3$ being methyl groups. As described in more detail below, CTMS compounds exhibit desirable properties as additives according to certain embodiments of the invention.

Examples of suitable CTMS compounds include, but are not limited to: 2-(Trimethylsilyl) thiazole, Bis(trimethylsilylmethyl)sulfide, 1,3-Bis[(trimethylsilyl)ethynyl]benzene, 4-(Trimethylsilyl)-3-butyn-2-one, 2,2-Bis-(trimethylsilyl) dithiane, and combinations thereof.

According to certain embodiments, suitable silicon-containing compounds according to formula (3) include compounds where at least one of $X_1$, $X_2$, $X_3$, and $X_4$ includes a fluorine atom or group. $X_1$, $X_2$, $X_3$, and $X_4$ can be the same or different, and, in some embodiments, at least one of $X_1$, $X_2$, $X_3$, and $X_4$ is an organic group including from 1 to 20 carbon atoms. For other embodiments, at least one of $X_1$, $X_2$, $X_3$, and $X_4$ is an organic group including more than 20 carbon atoms. In some embodiments, at least one of $X_1$, $X_2$, $X_3$, and $X_4$ includes an ether linkage, and, in other embodiments, at least one of $X$, $X_2$, $X_3$, and $X_4$ includes a silicon atom or another heteroatom. $X_1$, $X_2$, $X_3$, and $X_4$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, N-substituted arylcarbonylamino groups, and heterocycle groups.

Examples of compounds according to certain embodiments of the invention in which $X_4$ includes a fluorine atom or group include, but are not limited to: Tridecafluoro-1,1,2,2-tetrahydrooctyl)triethoxysilane, 1h,1h,2h,2h-Perfluorooctyl-triethoxysilane, (Pentafluorophenyl)triethoxysilane, Bis(1h,1h,2h,2h-perfluoroooctyl)tetramethyldisiloxane, 1,3-Bis(heptadecafluoro-1,1,2,2-tetrahydrodecyl) tetramethyldisiloxane, 1,2-Bis(methyldifluorosilyl)ethane, 1-3-Bis(trifluoropropyl)tetramethyldislioxane, Vinyl(trifluoromethyl)dimethylsilane, and combinations thereof.

In certain preferred embodiments, $X_1$, $X_2$, and $X_3$ are alkyl groups, and in particular methyl groups. In such preferred embodiments where each of $R_1$, $R_2$, and $R_3$ are methyl groups, these silicon-containing compounds are referred to as trimethylsilyl ("TMS") compounds provided by each of $X_1$, $X_2$, and $X_3$ being methyl groups. TMS compounds that also contain a fluorine atom or group can exhibit desirable properties as additives according to certain embodiments of the invention.

Examples of suitable TMS compounds which also contain a fluorine atom or group include, but are not limited to: Trimethylsilyl trifluoroacetate, N,O-Bis(trimethylsilyl)trifluoroacetamide, and combinations thereof.

According to certain embodiments, suitable silicon-containing compounds according to formula (3) include compounds where at least one of $X_1$, $X_2$, $X_3$, and $X_4$ includes an aromatic ring. $X_1$, $X_2$, $X_3$, and $X_4$ can be the same or different, and, in some embodiments, at least one of $X_1$, $X_2$, $X_3$, and $X_4$ is an organic group including from 1 to 20 carbon atoms. For other embodiments, at least one of $X_1$, $X_2$, $X_3$, and $X_4$ is an organic group including more than 20 carbon atoms. In some embodiments, at least one of $X_1$, $X_2$, $X_3$, and $X_4$ includes an ether linkage, and, in other embodiments, at least one of $X_1$, $X_2$, $X_3$, and $X_4$ includes a silicon atom or another heteroatom. $X_1$, $X_2$, $X_3$, and $X_4$ can be independently selected from, for example, hydride-group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, N-substituted arylcarbonylamino groups, and heterocycle groups.

Examples of compounds according to certain embodiments of the invention in which $X_4$ includes an aromatic ring include, but are not limited to: 1,3-Bis[(trimethylsilyl)ethynyl]benzene, Phenyltrimethoxysilane, Pentafluorophenyltriethoxysilane, and combinations thereof.

According to certain embodiments, suitable silicon-containing compounds according to formula (3) include compounds where at least one of $X_1$, $X_2$, $X_3$, and $X_4$ includes one or more unsaturated bond. $X_1$, $X_2$, $X_3$, and $X_4$ can be the same or different, and, in some embodiments, at least one of $X_1$, $X_2$, $X_3$, and $X_4$ is an organic group including from 1 to 20 carbon atoms. For other embodiments, at least one of $X_1$, $X_2$, $X_3$, and $X_4$ is an organic group including more than 20 carbon atoms. In some embodiments, at least one of $X_1$, $X_2$, $X_3$, and $X_4$ includes an ether linkage, and, in other embodiments, at least one of $X_1$, $X_2$, $X_3$, and $X_4$ includes a silicon atom or another heteroatom. $X_1$, $X_2$, $X_3$, and $X_4$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, N-substituted arylcarbonylamino groups, and heterocycle groups.

Examples of compounds according to certain embodiments of the invention in which $X_4$ includes one or more unsaturated bond include, but are not limited to: Bis(trimethylsilyl)carbodiimide, Tris(trimethylsilyloxy)ethylene, Isopropenoxytrimethylsilane, 4-(Trimethylsilyl)-3-butyn-2-one, Trivinylmethylsilane, Trivinylmethoxysilane, Vinyl(trifluoromethyl)dimethylsilane, Bis(trimethylsilyl) itaconate, Hexavinyldisiloxane, Trivinylethoxysilane, Allyltris(trimethoxysilyloxy)silane, 1,3-Bis[(trimethylsilyl)ethynyl]benzene, Phenyltrimethoxysilane, Pentafluorophenyltriethoxysilane, and combinations thereof.

According to certain embodiments, suitable silicon-containing compounds according to formula (3) include compounds where at least one of $X_1$, $X_2$, $X_3$, and $X_4$ includes an oxygen atom or group. $X_1$, $X_2$, $X_3$, and $X_4$ can be the same or different, and, in some embodiments, at least one of $X_1$, $X_2$, $X_3$, and $X_4$ is an organic group including from 1 to 20 carbon atoms. For other embodiments, at least one of $X_1$, $X_2$, $X_3$, and $X_4$ is an organic group including more than 20 carbon atoms. In some embodiments, at least one of $X_1$, $X_2$, $X_3$, and $X_4$ includes an ether linkage, and, in other embodiments, at least one of $X_1$, $X_2$, $X_3$, and $X_4$ includes a silicon atom or another heteroatom. $X_1$, $X_2$, $X_3$, and $X_4$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, N-substituted arylcarbonylamino groups, and heterocycle groups.

Examples of compounds according to certain embodiments of the invention in which $X_4$ includes an oxygen atom or group include, but are not limited to: 1,3-Bis(trimethylsiloxy)-1,3-dimethyldisiloxane, Tris(trimethylsilyl)phosphate, Decamethyltetrasiloxane, (Tridecafluoro-1,1,2,2-tetrahydrooctyl)triethoxysilane, Trimethylsilyl trifluoroacetate, Tris(trimethylsilyloxy)silane, Silicon tetraacetate, Tetramethyl orthosilicate, Decamethylcyclopentasiloxane, Tris(trimethylsilyloxy)ethylene, Ethoxytrimethylsilane, Octakis(dimethylsiloxy)-t8-silsesquioxane, Isopropenoxytrimethylsilane, Hexamethyldisiloxane, Phenyltrimethoxysilane, Pentafluorophenyltriethoxysilane, Hexamethylcyclotrisiloxane, Tris(trimethylsilyl)phosphite, N,O-Bis(trimethylsilyl)acetamide, Tris(trimethylsilyl) borate, Tetrakis(trimethylsilyloxy)silane, Tetrakis(dimethylsilyloxy)silane, Bis(tridecafluoro-1,1,2,2-tetrahydrooctyl)tetramethyldisiloxane, (Cyclohexenyloxy)trimethylsilane, Mono-(trimethylsilyl) phosphite, 2-(3,4-Epoxycyclohexyl)ethyltrimethoxysilane, Trimethyl-n-propoxysilane, Methoxytrimethylsilane, Tetrakis(trimethylsiloxy)titanium, Bis(trimethoxysilylpropyl) urea, 1,3-Bis(trifluoropropyl)tetramethyldisiloxane, Methacryloxypropylsilatrane, Triethoxysilylundecanal ethylene glycol acetal, Tris(trimethylsiloxy)antimony, Trivinylmethoxysilane, Tetradecamethylhexasiloxane, Methyltris(trimethylsiloxy)silane, Dodecamethylcyclohexasiloxane, Bis(trimethylsilyl)itaconate, Methylsilatrane, Hexavinyldisiloxane, 3-Ethylheptamethyltrisiloxane, 1,3-Bis(heptadecafluoro-1,1,2,2-tetrahydrodecyl)tetramethyldisiloxane, Trivinylethoxysilane, 1,1,1,3,3-Pentamethyl-3-acetoxydisiloxane, Bis(trimethylsilyl)adipate, Allyltris(trimethoxysilyloxy)silane, Trimethylsilyl polyphosphate, Dodecamethylcyclohexasiloxane, and combinations thereof.

In certain preferred embodiments, $X_1$, $X_2$, and $X_3$ are alkyl groups, and in particular methyl groups. In such preferred embodiments where each of $X_1$, $X_2$, and $X_3$ are methyl groups, these silicon-containing compounds are referred to as OTMS compounds after the silicon-oxygen bond ("O") and the trimethylsilyl ("TMS") provided by each of $X_1$, $X_2$, and $X_3$ being methyl groups. As described in more detail below, OTMS compounds exhibit desirable properties as additives according to certain embodiments of the invention.

Examples of suitable OTMS compounds include, but are not limited to: 1,3-Bis(trimethylsiloxy)-1,3-dimethyldisiloxane, decamethyltetrasiloxane, Trimethylsilyl trifluoroacetate, Ethoxytrimethylsilane, Isopropenoxytrimethylsilane, Hexamethyldisiloxane, Tris(trimethylsilyl)phosphate, Tris(trimethylsilyl)phosphite, Tetrakis(trimethylsilyloxy)silane, Tetrakis(trimethylsilyloxy)silane, Tris(dimethylsilyloxy)ethylene, N,O-Bis(trimethylsilyl)acetamide, Tris(trimethylsilyl) borate, Bis(tridecafluoro-1,1,2,2-tetrahydrooctyl)tetramethyldisiloxane, Trimethyl-n-propoxysilane, (Cyclohexenyloxy)trimethylsilane, Mono-(trimethylsilyl) phosphite, Methoxytrimethylsilane, Tetrakis(trimethylsiloxy)titanium, 1,3-Bis(trifluoropropyl)tetramethyldisiloxane, Tris(trimethylsiloxy)antimony, Trivinylmethoxysilane, Tetradecamethylhexasiloxane, Methyltris(trimethylsiloxy)silane, Dodecamethylcyclohexasiloxane, Bis(trimethylsilyl)itaconate, 3-Ethylheptamethyltrisiloxane, 1,3-Bis(heptadecafluoro-1,1,2,2-tetrahydrodecyl)tetramethyldisiloxane, 1,1,1,3,3-Pentamethyl-3-acetoxydisiloxane, Bis(trimethylsilyl)adipate, Allyltris(trimethoxysilyloxy)silane, Trimethylsilyl polyphosphate, and combinations thereof.

Desirable performance characteristics can be obtained by the inclusion of at least one A and at least one silicon-A bond in the silane according to formula (3), where A is a carbon atom or a heteroatom, such as one selected from boron, aluminum, silicon, phosphorus, sulfur, fluorine, chlorine, bromine, and iodine atoms. For example, at least one of X, $X_2$, $X_3$, and $X_4$ can include A that is bonded to the silicon of formula (3), and remaining ones of $X_1$, $X_2$, $X_3$, and $X_4$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. It is contemplated that multiple ones of $X_1$, $X_2$, $X_3$, and $X_4$ can each include A that is bonded to the silicon of formula (3), such that the silane according to formula (3) can include multiple silicon-A bonds, such as in the range of 2 to 4 or 3 to 4. It is also contemplated that multiple ones of $X_1$, $X_2$, $X_3$, and $X_4$ can include different and respective A's that are bonded to the silicon of formula (3), such that the silane according to formula (3) can include multiple silicon-A bonds (with respect to the different A's), such as in the range of 2 to 4 or 3 to 4. The number of silicon-A bonds can be increased beyond 4, for example, by the inclusion of silicon and silicon-A bonds within one or more of X, $X_2$, $X_3$, and $X_4$.

Desirable performance characteristics also can be obtained by the inclusion of at least one A and at least one silicon-O-A bond in the silane according to formula (3), where O is oxygen, and A is a carbon atom or a heteroatom, such as one selected from boron, aluminum, silicon, phosphorus, and sulfur atoms. For example, at least one of $X_1$, $X_2$, $X_3$, and $X_4$ can include O-A that is bonded to the silicon of formula (3) via a silicon-O-A bond, and remaining ones of $X_1$, $X_2$, $X_3$, and $X_4$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. It is contemplated that multiple ones of $X_1$, $X_2$, $X_3$, and $X_4$ can each include O-A that is bonded to the silicon of formula (3) via a silicon-O-A bond, such that the silane according to formula (3) can include multiple silicon-O-A bonds, such as in the range of 2 to 4 or 3 to 4. It is also contemplated that multiple ones of $X_1$, $X_2$, $X_3$, and $X_4$ can include different and respective A's that are bonded to the silicon of formula (3) via oxygen atoms, such that the silane according to formula (3) can include multiple silicon-O-A bonds (with respect to the different A's), such as in the range of 2 to 4 or 3 to 4. The number of silicon-O-A bonds can be increased beyond 4, for example, by the inclusion of silicon, oxygen, and silicon-O-A bonds within one or more of $X_1$, $X_2$, $X_3$, and $X_4$.

In the case that A is boron, particular examples of silicon-containing compounds according to formula (3) include silicon-containing boranes represented with reference to the formulas:

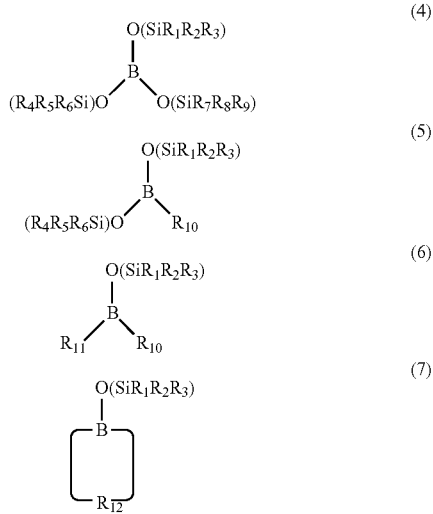

In formulas (4) through (7), $R_1$, $R_2$, and $R_3$ can correspond to $X_1$, $X_2$, and $X_3$ according to formula (3). $R_1$, $R_2$, $R_3$, $R_4$, $R_5$, $R_6$, $R_7$, $R_8$, $R_9$, $R_{10}$, and $R_{11}$ can be the same or different, and, in some embodiments, at least one of $R_1$, $R_2$, $R_3$, $R_4$, $R_5$, $R_6$, $R_7$, $R_8$, $R_9$, $R_{10}$, and $R_{11}$ is an organic group including from 1 to 20 carbon atoms. For other embodiments, at least one of $R_1$, $R_2$, $R_3$, $R_4$, $R_5$, $R_6$, $R_7$, $R_8$, $R_9$, $R_{10}$, and $R_{11}$ is an organic group including more than 20 carbon atoms. In some embodiments, at least one of $R_1$, $R_2$, $R_3$, $R_4$, $R_5$, $R_6$, $R_7$, $R_8$, $R_9$, $R_{10}$, and $R_{11}$ includes an ether linkage, and, in other embodiments, at least one of $R_1$, $R_2$, $R_3$, $R_4$, $R_5$, $R_6$, $R_7$, $R_8$, $R_9$, $R_{10}$, and $R_{11}$ includes a silicon atom or another heteroatom. $R_1$, $R_2$, $R_3$, $R_4$, $R_5$, $R_6$, $R_7$, $R_8$, $R_9$, $R_{10}$, and $R_{11}$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. In formula (7), $R_{12}$ is a bivalent, organic group including from 1 to 20 carbon atoms in some embodiments, and, for other embodiments, $R_{12}$ is a bivalent, organic group including more than 20 carbon atoms. $R_{12}$ can be selected from, for example, alkylene groups, alkenylene groups, and alkynylene groups.

In the case that A is aluminum, particular examples of silicon-containing compounds according to formula (3) include those represented with reference to the formulas:

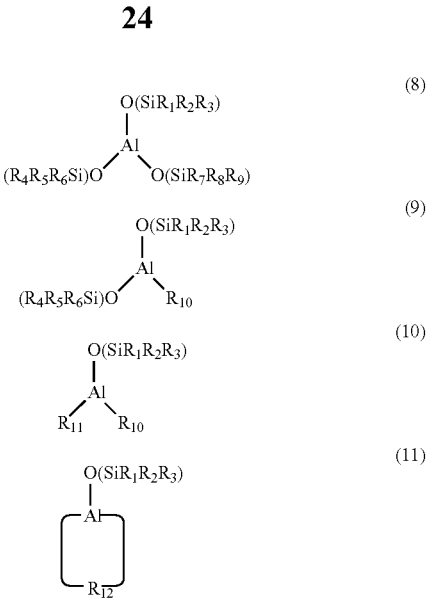

In formulas (8) through (11), $R_1$, $R_2$, and $R_3$ can correspond to $X_1$, $X_2$, and $X_3$ according to formula (3). $R_1$, $R_2$, $R_3$, $R_4$, $R_5$, $R_6$, $R_7$, $R_8$, $R_9$, $R_{10}$, and $R_{11}$ can be the same or different, and, in some embodiments, at least one of $R_1$, $R_2$, $R_3$, $R_4$, $R_5$, $R_6$, $R_7$, $R_8$, $R_9$, $R_{10}$, and $R_{11}$ is an organic group including from 1 to 20 carbon atoms. For other embodiments, at least one of $R_1$, $R_2$, $R_3$, $R_4$, $R_5$, $R_6$, $R_7$, $R_8$, $R_9$, $R_{10}$, and $R_{11}$ is an organic group including more than 20 carbon atoms. In some embodiments, at least one of $R_1$, $R_2$, $R_3$, $R_4$, $R_5$, $R_6$, $R_7$, $R_8$, $R_9$, $R_{10}$, and $R_{11}$ includes an ether linkage, and, in other embodiments, at least one of $R_1$, $R_2$, $R_3$, $R_4$, $R_5$, $R_6$, $R_7$, $R_8$, $R_9$, $R_{10}$, and $R_{11}$ includes a silicon atom or another heteroatom. $R_1$, $R_2$, $R_3$, $R_4$, $R_5$, $R_6$, $R_7$, $R_8$, $R_9$, $R_{10}$, and $R_{11}$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. In formula (II), $R_{12}$ is a bivalent, organic group including from 1 to 20 carbon atoms in some embodiments, and, for other embodiments, $R_{12}$ is a bivalent, organic group including more than 20 carbon atoms. $R_{12}$ can be selected from, for example, alkylene groups, alkenylene groups, and alkynylene groups.

In the case that A is carbon, particular examples of silicon-containing compounds according to formula (3) include those represented with reference to the formulas:

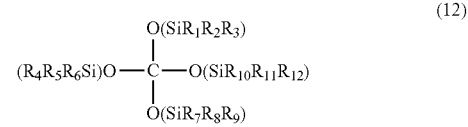

$$(R_4R_5R_6Si)O-\underset{\underset{O(SiR_7R_8R_9)}{|}}{\overset{\overset{O(SiR_1R_2R_3)}{|}}{C}}-R_{13} \quad (13)$$

$$(R_4R_5R_6Si)O-\underset{\underset{R_{14}}{|}}{\overset{\overset{O(SiR_1R_2R_3)}{|}}{C}}-R_{13} \quad (14)$$

$$R_{15}-\underset{\underset{R_{14}}{|}}{\overset{\overset{O(SiR_1R_2R_3)}{|}}{C}}-R_{13} \quad (15)$$

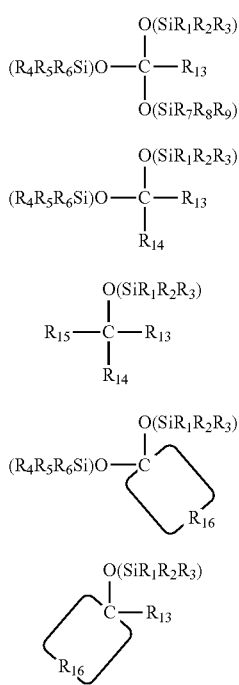

In formulas (12) through (17), $R_1$, $R_2$, and $R_3$ can correspond to $X_1$, $X_2$, and $X_3$ according to formula (3). $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ can be the same or different, and, in some embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ is an organic group including from 1 to 20 carbon atoms. For other embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ is an organic group including more than 20 carbon atoms. In some embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ includes an ether linkage, and, in other embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ includes a silicon atom or another heteroatom. $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. In formulas (16) and (17), $R_{16}$ is a bivalent, organic group including from 1 to 20 carbon atoms in some embodiments, and, for other embodiments, $R_{16}$ is a bivalent, organic group including more than 20 carbon atoms. $R_{16}$ can be selected from, for example, alkylene groups, alkenylene groups, and alkynylene groups.

In the case that A is carbon, additional examples of silicon-containing compounds according to formula (3) include those represented with reference to the formulas:

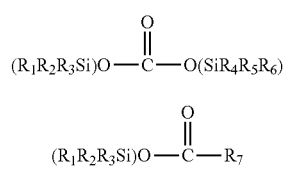

In formulas (18) and (19), $R_1$, $R_2$, and $R_3$ can correspond to $X_1$, $X_2$, and $X_3$ according to formula (3). $R_1$, $R_2$, $R_3$, $R_4$, $R_5$, $R_6$, and $R_7$ can be the same or different, and, in some embodiments, at least one of $R_1$, $R_2$, $R_3$, $R_4$, $R_5$, $R_6$, and $R_7$ is an organic group including from 1 to 20 carbon atoms. For other embodiments, at least one of $R_1$, $R_2$, $R_3$, $R_4$, $R_5$, $R_6$, and $R_7$ is an organic group including more than 20 carbon atoms. In some embodiments, at least one of $R_1$, $R_2$, $R_3$, $R_4$, $R_5$, $R_6$, and $R_7$ includes an ether linkage, and, in other embodiments, at least one of $R_1$, $R_2$, $R_3$, $R_4$, $R_5$, $R_6$, and $R_7$ includes a silicon atom or another heteroatom. $R_1$, $R_2$, $R_3$, $R_4$, $R_5$, $R_6$, and $R_7$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. In some embodiments, $R_7$ does not include any carbonyl group of the form —CO—, and, in other embodiments, $R_7$ does not include any sulfonyl group of the form —$SO_2$—.

In certain preferred embodiments, compounds of formula (19) alkyl groups comprise $R_1$, $R_2$, and $R_3$. In some embodiments, $R_1$, $R_2$, and $R_3$ are methyl groups. Examples of such trimethylsilyl compounds in which $R_7$ is chosen such that the compound comprises an ester include, but are not limited to: Silicon tetraacetate, Bis(trimethylsilyl)itaconate, Bis(trimethylsilyl)adipate, 1,1,1,3,3-Pentamethyl-3-acetoxydisiloxane, Trimethylsilyl trifluoroacetate, and combinations thereof.

In the case that A is silicon, particular examples of silicon-containing compounds according to formula (3) include silanes represented with reference to the formulas:

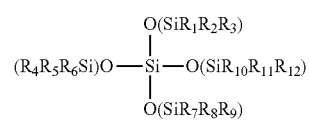

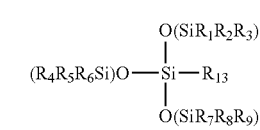

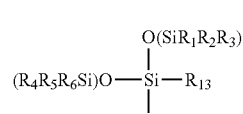

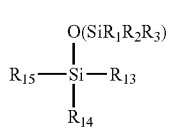# (23)

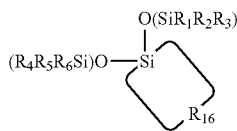# (24)

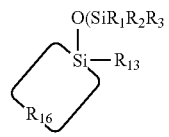# (25)

In formulas (20) through (25), $R_1$, $R_2$, and $R_3$ can correspond to $X_1$, $X_2$, and $X_3$ according to formula (3). $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ can be the same or different, and, in some embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ is an organic group including from 1 to 20 carbon atoms. For other embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ is an organic group including more than 20 carbon atoms. In some embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ includes an ether linkage, and, in other embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ includes a silicon atom or another heteroatom. $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. In formulas (24) and (25), $R_{16}$ is a bivalent, organic group including from 1 to 20 carbon atoms in some embodiments, and, for other embodiments, $R_{16}$ is a bivalent, organic group including more than 20 carbon atoms. $R_{16}$ can be selected from, for example, alkylene groups, alkenylene groups, and alkynylene groups. In some embodiments, the silanes according to formulas (20) through (25) are non-polymeric and have molecular weights no greater than about 10,000 daltons, such as no greater than about 5,000 daltons, no greater than about 4,000 daltons, no greater than about 3,000 daltons, no greater than about 2,000 daltons, no greater than about 1,000 daltons, no greater than about 900 daltons, no greater than about 800 daltons, no greater than about 700 daltons, no greater than about 600 daltons, or no greater than about 500 daltons.

Examples of compounds according to certain embodiments of the invention in which A is silicon include, but are not limited to: Decamethylcyclopentasiloxane, Octakis(dimethylsiloxy)-t8-silsesquioxane, Hexamethylcyclotrisiloxane, Octaphenyl-t8-silsesquioxane, Dodecamethylcyclohexasiloxane, and combinations thereof.

In the case that A is phosphorus, particular examples of silicon-containing compounds according to formula (3) include phosphines represented with reference to the formulas:

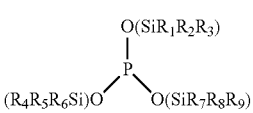# (26)

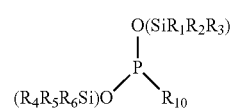# (27)

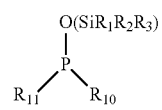# (28)

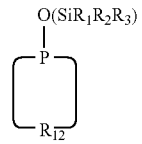# (29)

In formulas (26) through (29), $R_1$, $R_2$, and $R_3$ can correspond to $X_1$, $X_2$, and $X_3$ according to formula (3). $R_1$, $R_2$, $R_3$, $R_4$, $R_5$, $R_6$, $R_7$, $R_8$, $R_9$, $R_{10}$, and $R_{11}$ can be the same or different, and, in some embodiments, at least one of $R_1$, $R_2$, $R_3$, $R_4$, $R_5$, $R_6$, $R_7$, $R_8$, $R_9$, $R_{10}$, and $R_{11}$ is an organic group including from 1 to 20 carbon atoms. For other embodiments, at least one of $R_1$, $R_2$, $R_3$, $R_4$, $R_5$, $R_6$, $R_7$, $R_8$, $R_9$, $R_{10}$, and $R_{11}$ is an organic group including more than 20 carbon atoms. In some embodiments, at least one of $R_1$, $R_2$, $R_3$, $R_4$, $R_5$, $R_6$, $R_7$, $R_8$, $R_9$, $R_{10}$, and $R_{11}$ includes an ether linkage, and, in other embodiments, at least one of $R_1$, $R_2$, $R_3$, $R_4$, $R_5$, $R_6$, $R_7$, $R_8$, $R_9$, $R_{10}$, and $R_{11}$ includes a silicon atom or another heteroatom. $R_1$, $R_2$, $R_3$, $R_4$, $R_5$, $R_6$, $R_7$, $R_8$, $R_9$, $R_{10}$, and $R_{11}$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. In formula (29), $R_{12}$ is a bivalent, organic group including from 1 to 20 carbon atoms in some embodiments, and, for other embodiments, $R_{12}$ is a bivalent, organic group including more than 20 carbon atoms. $R_{12}$ can be selected from, for example, alkylene groups, alkenylene groups, and alkynylene groups.

In the case that A is phosphorus, additional examples of silicon-containing compounds according to formula (3) include phosphoranes represented with reference to the formulas:

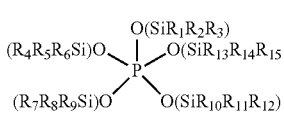
(30)

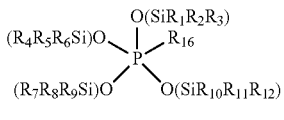
(31)

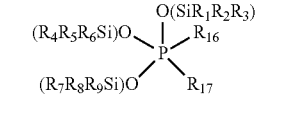
(32)

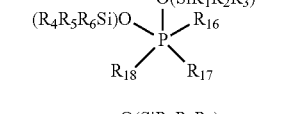
(33)

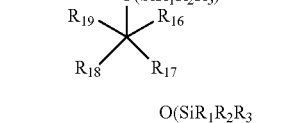
(34)

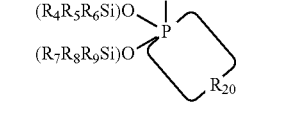
(35)

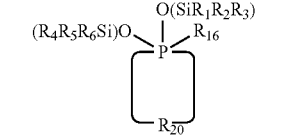
(36)

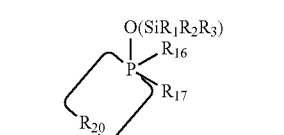
(37)

In formulas (30) through (37), $R_1$, $R_2$, and $R_3$ can correspond to $X_1$, $X_2$, and $X_3$ according to formula (3). $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ can be the same or different, and, in some embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ is an organic group including from 1 to 20 carbon atoms. For other embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ is an organic group including more than 20 carbon atoms. In some embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ includes an ether linkage, and, in other embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ includes a silicon atom or another heteroatom. $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. In formulas (35) through (37), $R_{20}$ is a bivalent, organic group including from 1 to 20 carbon atoms in some embodiments, and, for other embodiments, $R_{20}$ is a bivalent, organic group including more than 20 carbon atoms. $R_{20}$ can be selected from, for example, alkylene groups, alkenylene groups, and alkynylene groups.

In the case that A is phosphorus, additional examples of silicon-containing compounds according to formula (3) include phosphates and phosphate derivatives represented with reference to the formulas:

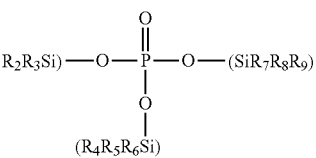
(38)

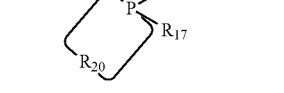
(39)

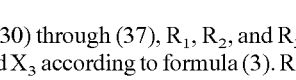
(40)

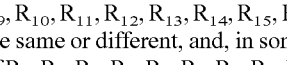

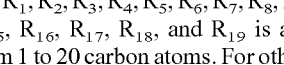
(41)

In formulas (38) through (41), $R_1$, $R_2$, and $R_3$ can correspond to $X_1$, $X_2$, and $X_3$ according to formula (3). $R_1$, $R_2$, $R_3$, $R_4$, $R_5$, $R_6$, $R_7$, $R_8$, $R_9$, $R_{10}$, and $R_{11}$ can be the same or different, and, in some embodiments, at least one of $R_1$, $R_2$, $R_3$, $R_4$, $R_5$, $R_6$, $R_7$, $R_8$, $R_9$, $R_{10}$, and $R_{11}$ is an organic group including from 1 to 20 carbon atoms. For other embodiments, at least one of $R_1$, $R_2$, $R_3$, $R_4$, $R_5$, $R_6$, $R_7$, $R_8$, $R_9$, $R_{10}$, and $R_{11}$ is an organic group including more than 20 carbon atoms. In some embodiments, at least one of $R_1$, $R_2$, $R_3$, $R_4$, $R_5$, $R_6$, $R_7$, $R_8$, $R_9$, $R_{10}$, and $R_{11}$ includes an ether linkage, and, in other embodiments, at least one of $R_1$, $R_2$, $R_3$, $R_4$, $R_5$, $R_6$, $R_7$, $R_8$, $R_9$, $R_{10}$, and $R_{11}$ includes a silicon atom or another heteroatom. $R_1$, $R_2$, $R_3$, $R_4$, $R_5$, $R_6$, $R_7$, $R_8$, $R_9$, $R_{10}$, and $R_{11}$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. In formula (41), $R_{12}$ is a bivalent, organic group including from 1 to 20 carbon atoms in some embodiments, and, for other embodiments, $R_{12}$ is a bivalent, organic group including more than 20 carbon atoms. $R_{12}$ can be selected from, for example, alkylene groups, alkenylene groups, and alkynylene groups.

A particular example of a phosphate according to formula (38) is Tris(trimethylsilyl) phosphate represented with reference to the formula:

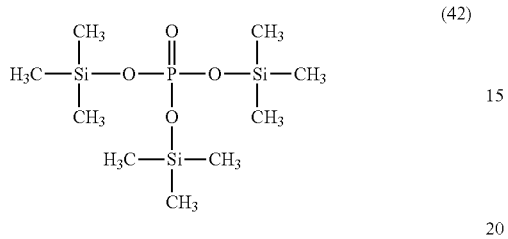
(42)

In formula (42), it is contemplated that one or more of the methyl groups can be modified, such as by substituting a constituent hydrogen atom with another chemical element or functional group, or can be replaced by another alkyl group, an alkenyl group, an alkynyl group, or an aryl group, either in a substituted or an unsubstituted form. Other functionalizations or modifications of the phosphate set forth in formula (42) are contemplated. Other examples of compounds according to certain embodiments of the invention in which A is phosphorus include, but are not limited to: Tris(trimethylsilyl)phosphate, Tris(trimethylsilyl)phosphite, Trimethylsilyl polyphosphate, and combinations thereof.

In the case that A is sulfur, particular examples of silicon-containing compounds according to formula (3) include sulfides represented with reference to the formulas:

(43)

(44)

In formulas (43) and (44), $R_1$, $R_2$, and $R_3$ can correspond to $X_1$, $X_2$, and $X_3$ according to formula (3). $R_1$, $R_2$, $R_3$, $R_4$, $R_5$, $R_6$, and $R_7$ can be the same or different, and, in some embodiments, at least one of $R_1$, $R_2$, $R_3$, $R_4$, $R_5$, $R_6$, and $R_7$ is an organic group including from 1 to 20 carbon atoms. For other embodiments, at least one of $R_1$, $R_2$, $R_3$, $R_4$, $R_5$, $R_6$, and $R_7$ is an organic group including more than 20 carbon atoms. In some embodiments, at least one of $R_1$, $R_2$, $R_3$, $R_4$, $R_5$, $R_6$, and $R_7$ includes an ether linkage, and, in other embodiments, at least one of $R_1$, $R_2$, $R_3$, $R_4$, $R_5$, $R_6$, and $R_7$ includes a silicon atom or another heteroatom. $R_1$, $R_2$, $R_3$, $R_4$, $R_5$, $R_6$, and $R_7$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups.

In the case that A is sulfur, additional examples of silicon-containing compounds according to formula (3) include those represented with reference to the formulas:

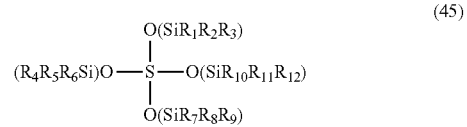
(45)

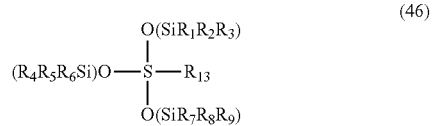
(46)

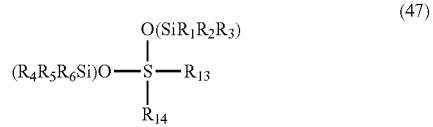
(47)

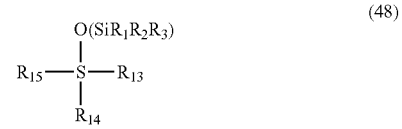
(48)

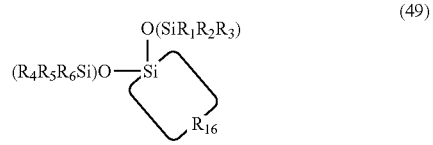
(49)

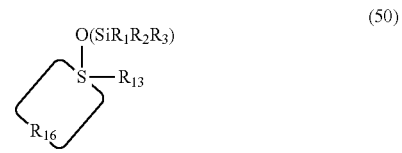
(50)

In formulas (45) through (50), $R_1$, $R_2$, and $R_3$ can correspond to $X_1$, $X_2$, and $X_3$ according to formula (3). $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ can be the same or different, and, in some embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ is an organic group including from 1 to 20 carbon atoms. For other embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ is an organic group including more than 20 carbon atoms. In some embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ includes an ether linkage, and, in other embodiments, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ includes a silicon atom or another heteroatom. $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups. In formulas (49) and (50), $R_{16}$ is a bivalent, organic group including from 1 to 20 carbon atoms in some embodiments, and, for other embodiments, $R_{16}$ is a bivalent, organic group including more than 20 carbon atoms. $R_{16}$ can be selected from, for example, alkylene groups, alkenylene groups, and alkynylene groups.

In the case that A is sulfur, additional examples of silicon-containing compounds according to formula (3) include sulfoxides represented with reference to the formulas:

(51)

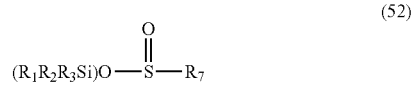

(52)

In formulas (51) and (52), $R_1$, $R_2$, and $R_3$ can correspond to $X_1$, $X_2$, and $X_3$ according to formula (3). $R_1$, $R_2$, $R_3$, $R_4$, $R_5$, $R_6$, and $R_7$ can be the same or different, and, in some embodiments, at least one of $R_1$, $R_2$, $R_3$, $R_4$, $R_5$, $R_6$, and $R_7$ is an organic group including from 1 to 20 carbon atoms. For other embodiments, at least one of $R_1$, $R_2$, $R_3$, $R_4$, $R_5$, $R_6$, and $R_7$ is an organic group including more than 20 carbon atoms. In some embodiments, at least one of $R_1$, $R_2$, $R_3$, $R_4$, $R_5$, $R_6$, and $R_7$ includes an ether linkage, and, in other embodiments, at least one of $R_1$, $R_2$, $R_3$, $R_4$, $R_5$, $R_6$, and $R_7$ includes silicon or another heteroatom. $R_1$, $R_2$, $R_3$, $R_4$, $R_5$, $R_6$, and $R_7$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups.

In the case that A is sulfur, additional examples of silicon-containing compounds according to formula (3) include sulfonates represented with reference to the formulas:

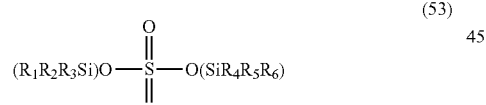

(53)

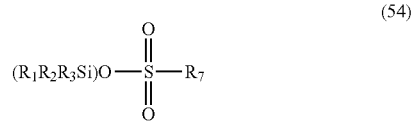

(54)

In formulas (53) and (54), $R_1$, $R_2$, and $R_3$ can correspond to $X_1$, $X_2$, and $X_3$ according to formula (3). $R_1$, $R_2$, $R_3$, $R_4$, $R_5$, $R_6$, and $R_7$ can be the same or different, and, in some embodiments, at least one of $R_1$, $R_2$, $R_3$, $R_4$, $R_5$, $R_6$, and $R_7$ is an organic group including from 1 to 20 carbon atoms. For other embodiments, at least one of $R_1$, $R_2$, $R_3$, $R_4$, $R_5$, $R_6$, and $R_7$ is an organic group including more than 20 carbon atoms. In some embodiments, at least one of $R_1$, $R_2$, $R_3$, $R_4$, $R_5$, $R_6$, and $R_7$ includes an ether linkage, and, in other embodiments, at least one of $R_1$, $R_2$, $R_3$, $R_4$, $R_5$, $R_6$, $R_7$, and $R_7$ includes a silicon atom or another heteroatom. $R_1$, $R_2$, $R_3$, $R_4$, $R_5$, $R_6$, and $R_7$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups.

A particular example of a sulfonate according to formula (54) includes $R_7$ as a halo substituted alkyl group, namely t-Butyldimethylsilyl trifluoromethane sulfonate represented with reference to the formula:

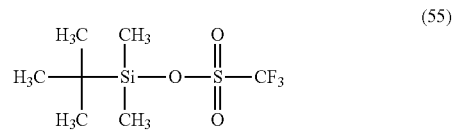

(55)

In formula (55), it is contemplated that one or more of the alkyl groups and the alkylfluoride group can be modified, such as by substituting a constituent hydrogen or fluorine atom with another chemical element or functional group, or can be replaced by another alkyl group, an alkenyl group, an alkynyl group, or an aryl group, either in a substituted or an unsubstituted form. Other functionalizations or modifications of the sulfonate set forth in formula (55) are contemplated.

Further examples of suitable silicon-containing compounds include silicon-containing polymers, such as a polyphosphate with silicon-containing side groups represented with reference to the formula:

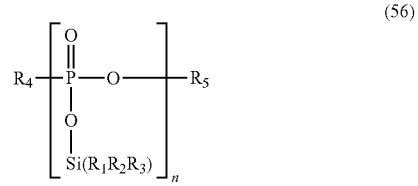

(56)

In formula (56), n is a non-negative integer that is at least one or greater than one and represents the number of repeat units included in the polyphosphate. For certain embodiments, n is in the range of 1 to 10, such as 2 to 10, and, in other embodiments, n is at least 10, such as at least 20, at least 50, at least 100, at least 500, or at least 1,000, and up to 5,000, up to 10,000, up to 50,000, up to 100,000 or more. $R_1$, $R_2$, $R_3$, $R_4$, and $R_5$ can be the same or different, and, in some embodiments, at least one of $R_1$, $R_2$, $R_3$, $R_4$, and $R_5$ is an organic group including from 1 to 20 carbon atoms. For other embodiments, at least one of $R_1$, $R_2$, $R_3$, $R_4$, and $R_5$ is an organic group including more than 20 carbon atoms. In some embodiments, at least one of $R_1$, $R_2$, $R_3$, $R_4$, and $R_5$ includes an ether linkage, and, in other embodiments, at least one of $R_1$, $R_2$, $R_3$, $R_4$, and $R_5$ includes a silicon atom or another heteroatom. $R_1$, $R_2$, $R_3$, $R_4$, and $R_5$ can be independently selected from, for example, hydride group, hydroxy group, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonylamino groups, N-substituted alkynylcarbonylamino groups, arylcarbonylamino groups, and N-substituted arylcarbonylamino groups.

Further, compounds of the various formulas (3) through (56) may be formulated as salts along with suitable ions. Such compounds can contain any of the many substitutions described in the formulas (3) through (56) in order to interact with a counter-ion. Examples of suitable silicon-containing salts include, but are not limited to: Calcium metasilicate, Tris[N,N-bis(trimethylsilyl)amide]erbium(III), Sodium hexafluorosilicate, and combinations thereof.

It is understood that certain compounds fall into more than one family or group as described in formulas (3) through (56) and the associated description. Many compounds of embodiments of the invention preferably contain one or more TMS structures. Such TMS structures can facilitate the appropriate decomposition of additives to improve the performance of conventional electrolytes. Without being bound by a particular theory or mode of action, the presence of silicon in additives can facilitate the formation of a silicon-containing film, layer, coating, or region on or within electrode materials. Such film formation is described in more detail below.

Referring back to formulas (1) and (2), an amount of a particular compound can be expressed in terms of a weight percent of the compound relative to a total weight of the electrolyte solution (or wt. %). For example, an amount of a compound can be in the range of about 0.01 wt. % to about 30 wt. %, such as from about 0.05 wt. % to about 30 wt. %, from about 0.01 wt. % to about 20 wt. %, from about 0.2 wt. % to about 15 wt. %, from about 0.2 wt. % to about 10 wt. %, from about 0.2 wt. % to about 5 wt. %, or from about 5 wt. % to about 10 wt. %, and, in the case of a combination of multiple compounds, a total amount of the compounds can be in the range of about 0.01 wt. % to about 30 wt. %, such as from about 0.05 wt. % to about 30 wt. %, from about 0.01 wt. % to about 20 wt. %, from about 0.2 wt. % to about 15 wt. %, from about 0.2 wt. % to about 10 wt. %, from about 0.2 wt. % to about 5 wt. %, or from about 5 wt. % to about 10 wt. %. An amount of a compound also can be expressed in terms of a ratio of the number of moles of the compound per unit surface area of either, or both, electrode materials. For example, an amount of a compound can be in the range of about $10^{-7}$ mol/m$^2$ to about $10^{-2}$ mol/m$^2$, such as from about $10^{-7}$ mol/m$^2$ to about $10^{-5}$ mol/m$^2$, from about $10^{-5}$ mol/m$^2$ to about $10^{-3}$ mol/m$^2$, from about $10^{-6}$ mol/m$^2$ to about $10^{-4}$ mol/m$^2$, or from about $10^{-4}$ mol/m$^2$ to about $10^{-2}$ mol/m$^2$. As further described below, a compound can be consumed or can react, decompose, or undergo other modifications during initial battery cycling. As such, an amount of a compound can refer to an initial amount of the compound used during the formation of the electrolyte solutions according to formulas (1) or (2), or can refer to an initial amount of the additive within the electrolyte solution prior to battery cycling (or prior to any significant amount of battery cycling).

Resulting performance characteristics of a battery can depend upon the identity of a particular compound used to form the high voltage electrolyte according to formulas (1) or (2), an amount of the compound used, and, in the case of a combination of multiple compounds, a relative amount of each compound within the combination. Accordingly, the resulting performance characteristics can be fine-tuned or optimized by proper selection of the set of compounds and adjusting amounts of the compounds in formulas (1) or (2). For example, in the case of certain phosphates when used as an additive compound, such as tris(trimethylsilyl) phosphate, a desirable amount of the compound can be in the range of about 0.5 wt. % to about 3 wt. %, such as from about 1 wt. % to about 2 wt. %. Fine-tuning of an amount of an additive compound can depend upon factors such as battery configuration and characteristics of a cathode material or anode material.

The formation according to formulas (1) or (2) can be carried out using a variety of techniques, such as by mixing the base electrolyte and the set of additives, dispersing the set of additives within the base electrolyte, dissolving the set of additives within the base electrolyte, or otherwise placing these components in contact with one another. The set of additives can be provided in a liquid form, a powdered form (or another solid form), or a combination thereof. The set of additives can be incorporated in the electrolyte solutions of formulas (1) or (2) prior to, during, or subsequent to battery assembly.

The electrolyte solutions described herein can be used for a variety of batteries containing a high voltage cathode or a low voltage cathode, and in batteries operated at high temperatures. For example, the electrolyte solutions can be substituted in place of, or used in conjunction with, conventional electrolytes for Li-ion batteries for operations at or above 4.2 V.

FIG. 1 illustrates a Li-ion battery 100 implemented in accordance with an embodiment of the invention. The battery 100 includes an anode 102, a cathode 106, and a separator 108 that is disposed between the anode 102 and the cathode 106. In the illustrated embodiment, the battery 100 also includes a high voltage electrolyte 104, which is disposed between the anode 102 and the cathode 106 and remains stable during high voltage battery cycling.

The operation of the battery 100 is based upon reversible intercalation and de-intercalation of Li ions into and from host materials of the anode 102 and the cathode 106. Other implementations of the battery 100 are contemplated, such as those based on conversion chemistry. Referring to FIG. 1, the voltage of the battery 100 is based on redox potentials of the anode 102 and the cathode 106, where Li ions are accommodated or released at a lower potential in the former and a higher potential in the latter. To allow both a higher energy density and a higher voltage platform to deliver that energy, the cathode 106 includes an active cathode material for high voltage operations at or above 4.2 V. Suitable high voltage cathode materials include those having a specific capacity of at least about 10 mAh/g, at least about 20 mAh/g, at least about 30 mAh/g, at least about 40 mAh/g, or at least about 50 mAh/g, as measured upon discharge at a rate of 0.1 C (or another reference rate higher or lower than 0.1 C, such as 0.05 C, 0.5 C, or 1 C) from about 6 V to about 4.5 V, from about 6 V to about 5 V, from about 5.5 V to about 4.5 V, or from about 5 V to about 4.5 V relative to a lithium metal anode (Li/Li$^+$ anode) or other counterelectrode. Suitable high voltage cathode materials also include those having a specific capacity of at least about 10 mAh/g, at least about 20 mAh/g, at least about 30 mAh/g, at least about 40 mAh/g, or at least about 50 mAh/g, as measured upon discharge at a substantially constant current of 15 mA/g (or another reference current higher or lower than 15 mA/g, such as 7.5 mA/g, 75 mA/g, or 150 mA/g) from about 6 V to about 4.5 V, from about 6 V to about 5 V, from about 5.5 V to about 4.5 V, or from about 5 V to about 4.5 V relative to a lithium metal anode (Li/Li anode) or other counterelectrode. The stated values for specific capacity and current can be per unit mass of a cathode active material, and can be expressed in units of mAh/(g of the cathode active material) and mA/(g of the cathode active material), respectively. Examples of suitable high voltage cathode materials include phosphates, fluorophosphates, fluorosulphates, fluorosilicates, spinels, Li-rich layered oxides, and composite layered oxides. Further examples of suitable cathode materials include: spinel structure lithium metal oxides, layered structure lithium metal oxides, lithium-rich layered structured lithium metal oxides, lithium metal silicates, lithium metal phosphates, metal fluorides, metal oxides, sulfur, and metal sulfides. Examples of suitable anode materials include conventional anode materials used in Li-ion batteries, such as lithium, graphite ("$Li_x C_6$"), and other carbon, silicate, or oxide-based anode materials.

For example, a class of suitable high voltage phosphates can be represented as: $Li_a(M1_b M2_c M3_d M4_e)_f PO_4$, where M1, M2, M3, and M4 can be the same or different, M1 is Mn, Co, or Ni, M2 is a transition metal, such as Ti, V, Cr, Mn, Fe, Co, Ni, Zr, Nb, or Mo, M3 is a transition metal or a main group element, optionally excluding elements of Group VIA and Group VIIA, M4 is a transition metal or a main group element, optionally excluding elements of Group VIA and Group VIIA, $1.2 \geq a \geq 0.9$ (or $1.2 > a > 0.9$), $1 \geq b \geq 0.6$ (or $1 > b > 0.6$), $0.4 \geq c \geq 0$ (or $0.4 > c > 0$), $0.2 \geq d \geq 0$ (or $0.2 > d > 0$), $0.2 \geq e \geq 0$ (or $0.2 > e > 0$), and $1.2 \geq f \geq 0.9$ (or $1.2 > f > 0.9$). Additional details regarding this class of cathode materials can be found in Goodenough et al., "Challenges for Rechargeable Li Batteries," Chemistry of Materials 22, 587-603 (2010); Marom et al., "A review of advanced and practical lithium battery materials," J. Mater. Chem., 21, 9938 (2011); Zhi-Ping et al., "Li-Site and Metal-Site Ion Doping in Phosphate-Olivine $LiCoPO_4$ by First-Principles Calculation," Chin. Phys. Lett. 26 (3) 038202 (2009); and Fisher et al., "Lithium Battery Materials $LiMPO_4$ (M) Mn, Fe, Co, and Ni): Insights into Defect Association, Transport Mechanisms, and Doping Behavior," Chem. Mater. 2008, 20, 5907-5915; the disclosures of which are incorporated herein by reference in their entirety.

For example, another class of suitable high voltage phosphates can comprise lithium (Li), cobalt (Co), a first transition metal (M1), a second transition metal (M2) different from M1, and phosphate ($PO_4$), where M1 and M2 are each selected from iron (Fe), titanium (Ti), vanadium (V), niobium (Nb), zirconium (Zr), hafnium (Hf), molybdenum (Mo), tantalum (Ta), tungsten (W), manganese (Mn), copper (Cu), chromium (Cr), nickel (Ni), and zinc (Zn) (e.g., as dopants and/or oxides thereof), and can have molar ratios of Li:Co:M1:M2:$PO_4$ defined by $(1-x):(1-y-z):y:z:(1-a)$, respectively, optionally represented (as a shorthand notation) as: $Li_{(1-x)}:Co_{(1-y-z)}:M1_y:M2_z:(PO_4)_{(1-a)}$, where $-0.3 \leq x \leq 0.3$; $0.01 \leq y \leq 0.5$; $0.01 \leq z \leq 0.3$; $-0.5 \leq a \leq 0.5$; and $0.2 \leq 1-y-z \leq 0.98$. Preferably, M1 and M2 are each selected from iron (Fe), titanium (Ti), vanadium (V) and niobium (Nb) (e.g., as dopants and/or oxides thereof). Preferably, M1 is iron (Fe) (e.g., as a dopant and/or oxide thereof), M2 is selected from titanium (Ti), vanadium (V), and niobium (Nb) (e.g., as dopants and/or oxides thereof). Preferably, $-0.3 \leq x < 0$, $-0.2 \leq x < 0$, or $-0.1 \leq x < 0$. Preferably, M2 is Ti, and $0.05 \leq z \leq 0.25$ or $0.05 \leq z \leq 0.2$. Preferably, M2 is V, and $0.03 \leq z \leq 0.25$ or $0.05 \leq z \leq 0.2$. Preferably, $0.3 \leq 1-y-z \leq 0.98$, $0.5 \leq 1-y-z \leq 0.98$, or $0.7 \leq 1-y-z \leq 0.98$. Additional details regarding this class of olivine cathode materials can be found in co-pending and co-owned U.S. Provisional Application No. 61/426,733, entitled "Lithium Ion Battery Materials with Improved Properties" and filed on Dec. 23, 2010, the disclosure of which is incorporated herein by reference in its entirety.

For example, a class of suitable high voltage fluorophosphates can be represented as: $Li_a(M1_b M2_c M3_d M4_e)_f PO_4 F_g$, where M1, M2, M3, and M4 can be the same or different, M1 is Mn, Co, or Ni, M2 is a transition metal, such as Ti, V, Cr, Mn, Fe, Co, Ni, Zr, Nb, or Mo, M3 is a transition metal or a main group element, optionally excluding elements of Group VIA and Group VIIA, M4 is a transition metal or a main group element, optionally excluding elements of Group VIA and Group VIIA, $1.2 \geq a \geq 0.9$ (or $1.2 > a > 0.9$), $1 \geq b \geq 0.6$ (or $1 > b > 0.6$), $0.4 \geq c \geq 0$ (or $0.4 > c > 0$), $0.2 \geq d \geq 0$ (or $0.2 > d > 0$), $0.2 \geq e \geq 0$ (or $0.2 > e > 0$), $1.2 \geq f \geq 0.9$ (or $1.2 > f > 0.9$), and $1.2 \geq g \geq 0$ (or $1.2 > g > 0$).

For example, a class of suitable high voltage fluorosilicates can be represented as: $Li_a(M1_b M2_c M3_d M4_e)_f SiO_4 F$, where M1, M2, M3, and M4 can be the same or different, M1 is Mn, Co, or Ni, M2 is a transition metal, such as Ti, V, Cr, Mn, Fe, Co, Ni, Zr, Nb, or Mo, M3 is a transition metal or a main group element, optionally excluding elements of Group VIA and Group VIIA, M4 is a transition metal or a main group element, optionally excluding elements of Group VIA and Group VIIA, $1.2 \geq a \geq 0.9$ (or $1.2 > a > 0.9$), $1 \geq b \geq 0.6$ (or $1 > b > 0.6$), $0.4 \geq c \geq 0$ (or $0.4 > c > 0$), $0.2 \geq d \geq 0$ (or $0.2 > d > 0$), $0.2 \geq e \geq 0$ (or $0.2 > e > 0$), and $1.2 \geq f \geq 0.9$ (or $1.2 > f > 0.9$).

For example, another class of suitable high voltage fluorosilicates can be represented as: $Li_a(M1_b M2_c M3_d M4_e)_f SiO_4 F_g$, where M1, M2, M3, and M4 can be the same or different, M1 is Mn, Co, or Ni, M2 is a transition metal, such as Ti, V, Cr, Mn, Fe, Co, Ni, Zr, Nb, or Mo, M3 is a transition metal or a main group element, optionally excluding elements of Group VIA and Group VIIA, M4 is a transition metal or a main group element, optionally excluding elements of Group VIA and Group VIIA, $1.2 \geq a \geq 0.9$ (or $1.2 > a > 0.9$), $1 \geq b \geq 0.6$ (or $1 > b > 0.6$), $0.4 \geq c \geq 0$ (or $0.4 > c > 0$), $0.2 \geq d \geq 0$ (or $0.2 > d > 0$), $0.2 \geq e \geq 0$ (or $0.2 > e > 0$), $1.2 \geq f \geq 0.9$ (or $1.2 > f > 0.9$), and $1.2 \geq g \geq 0$ (or $1.2 > g > 0$).

For example, a class of suitable high voltage spinels can be represented as: $Li_a(M1_b M2_c M3_d M4_e)_f O_4$, where M1, M2, M3, and M4 can be the same or different, M1 is Mn or Fe, M2 is Mn, Ni, Fe, Co, or Cu, M3 is a transition metal, such as Ti, V, Cr, Mn, Fe, Co, Ni, Zr, Nb, or Mo, and M4 is a transition metal or a main group element, optionally excluding elements of Group VIA and Group VIIA, $1.2 \geq a \geq 0.9$ (or $1.2 > a > 0.9$), $1.7 \geq b \geq 1.2$ (or $1.7 > b > 1.2$), $0.8 \geq c \geq 0.3$ (or $0.8 > c > 0.3$), $0.1 \geq d \geq 0$ (or $0.1 > d > 0$), $0.1 \geq e \geq 0$ (or $0.1 > e > 0$), and $2.2 \geq f \geq 1.5$ (or $2.2 > f > 1.5$). LMNO-type cathode materials, such as $Li_{1.05}Mn_{0.5}Ni_{0.5}O_4$ and LMO-type materials, such as $LiMn_2O_4$ are included in this class. Additional details regarding this class of cathode materials can be found in Goodenough et al., "Challenges for Rechargeable Li Batteries," Chemistry of Materials 22, 587-603 (2010); Marom et al., "A review of advanced and practical lithium battery materials," J. Mater. Chem., 21, 9938 (2011); and Yi et al., "Recent developments in the doping of $LiNi_{0.5}Mn_{1.5}O_4$ cathode material for 5 V lithium-ion batteries," Ionics (2011) 17:383-389; the disclosures of which are incorporated herein by reference in their entirety.

For example, a class of suitable high voltage, Li-rich layered oxides can be represented as: $Li(Li_a M1_b M2_c M3_d M4_e)_f O_2$, where M1, M2, M3, and M4 can be the same or different, M1 is a transition metal, such as Mn, Fe, V, Co, or Ni, M2 is a transition metal, such as Mn, Fe, V, Co, or Ni, M3 is a transition metal, such as Mn, Fe, V, Co, or Ni, M4 is a transition metal or a main group element, optionally excluding elements of Group VIA and Group VIIA, $0.4 \geq a \geq 0.05$ (or $0.4>a>0.05$), $0.7 \geq b \geq 0.1$ (or $0.7>b>0.1$), $0.7 \geq c \geq 0.1$ (or $0.7>c>0.1$), $0.7 \geq d \geq 0.1$ (or $0.7>d>0.1$), $0.2 \geq e \geq 0$ (or $0.2>e>0$), and $1.2 \geq f \geq 0.9$ (or $1.2>f>0.9$). OLO-type cathode materials are included in this class. Additional details regarding this class of cathode materials can be found in Goodenough et al., "Challenges for Rechargeable Li Batteries," Chemistry of Materials 22, 587-603 (2010); Marom et al., "A review of advanced and practical lithium battery materials" J. Mater. Chem., 21, 9938 (2011); Johnson et al., "Synthesis, Characterization and Electrochemistry of Lithium Battery Electrodes: $xLi_2MnO_3$ $(1-x)LiMn_{0.333}Ni_{0.333}Co_{0.333}O_2$ ($0<x<0.7$)," Chem. Mater., 20, 6095-6106 (2008); and Kang et al., "Interpreting the structural and electrochemical complexity of $0.5Li_2MnO_3.0.5LiMO_2$ electrodes for lithium batteries ($M=Mn_{0.5-x}Ni_{0.5-x}Co_{2x}$, $0=x=0.5$)," J. Mater. Chem., 17, 2069-2077 (2007); the disclosures of which are incorporated herein by reference in their entirety.

For example, a class of suitable high voltage, composite layered oxides can be represented as: $(Li_2M1_aM2_bO_3)_c$ $(LiM3_dM4_eM5_fO_2)_g$, where M1, M2, M3, M4, and M5 can be the same or different, M1 is a transition metal, such as Mn, Fe, V, Co, or Ni, M2 is a transition metal, such as Mn, Fe, V, Co, or Ni, M3 is a transition metal, such as Mn, Fe, V, Co, or Ni, M4 is a transition metal, such as Mn, Fe, V, Co, or Ni, M5 is a transition metal or a main group element, optionally excluding elements of Group VIA and Group VIIA, $1.1 \geq a \geq 0$ (or $1.1>a>0$), $0.5 \geq b \geq 0$ (or $0.5>b>0$), $0.7 \geq c \geq 0$ (or $0.7>c>0$), $1 \geq d \geq 0$ (or $1>d>0$), $1 \geq e \geq 0$ (or $1>e>0$), $1 \geq f \geq 0$ (or $1>f>0$), and $1 \geq g \geq 0.5$ (or $1>g>0.5$). Additional details regarding this class of cathode materials can be found in Goodenough et al., "Challenges for Rechargeable Li Batteries," Chemistry of Materials 22, 587-603 (2010); Marom et al., "A review of advanced and practical lithium battery materials," J. Mater. Chem., 21, 9938 (2011); Johnson et al., "Synthesis, Characterization and Electrochemistry of Lithium Battery Electrodes: $xLi_2MnO_3$ $(1-x)LiMn_{0.333}Ni_{0.333}Co_{0.333}O_2$ ($0<x<0.7$)," Chem. Mater., 20, 6095-6106 (2008); and Kang et al., "Interpreting the structural and electrochemical complexity of $0.5Li_2MnO_3.0.5LiMO_2$ electrodes for lithium batteries ($M=Mn_{0.5-x}Ni_{0.5-x}Co_{2x}$, $0=x=0.5$)," J. Mater. Chem., 17, 2069-2077 (2007); the disclosures of which are incorporated herein by reference in their entirety.

Figure 2:
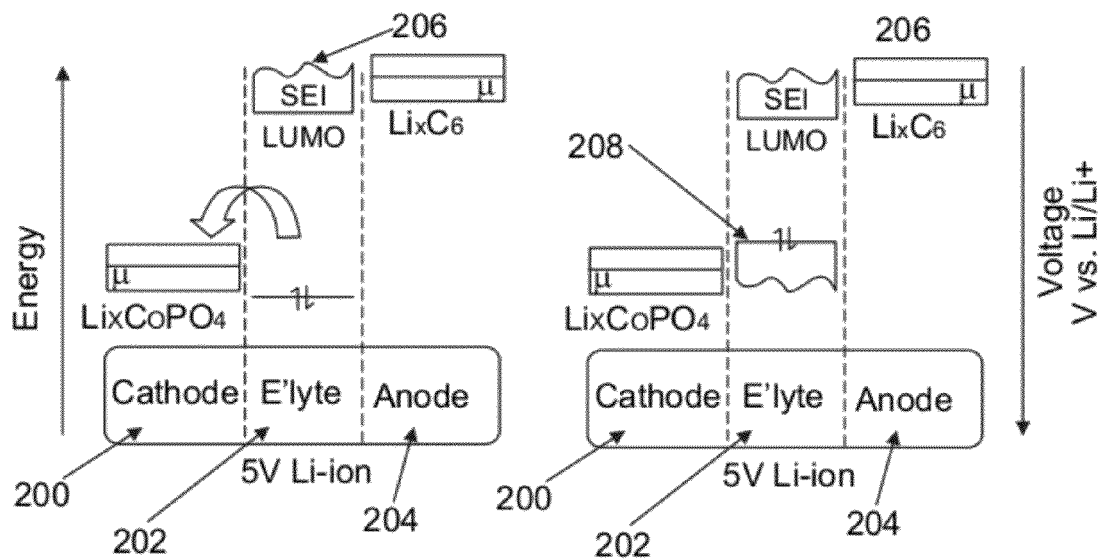
FIG. 2 illustrates the operation of a Li-ion battery and a graphical representation of an illustrative non-limiting mechanism of action of an electrolyte including an additive compound, according to an embodiment of the invention.

Attention next turns to FIG. 2, which illustrates operation of a Li-ion battery and an illustrative, non-limiting mechanism of action of an improved electrolyte, according to an embodiment of the invention. Without being bound by a particular theory not recited in the claims, the inclusion of a set of one or more stabilizing additive compounds in an electrolyte solution can, upon operation of the battery (e.g., during conditioning thereof) passivate a high voltage cathode material, thereby reducing or preventing reactions between bulk electrolyte components and the cathode material that can degrade battery performance.

Referring to FIG. 2, an electrolyte 202 includes a base electrolyte, and, during initial battery cycling, components within the base electrolyte can assist in the in-situ formation of a protective film (in the form of a solid electrolyte interface ("SEI") 206) on or next to an anode 204. The anode SEI 206 can inhibit reductive decomposition of the high voltage electrolyte 202. Preferably, and without being bound by theory not recited in the claims, for operation at voltages at or above 4.2 V, the electrolyte 202 can also include a set of additives that can assist in the in-situ formation of a protective film (in the form of a SEI 208 or another derivative) on or next to a cathode 200. The cathode SEI 208 can inhibit oxidative decomposition of the high voltage electrolyte 202 that can otherwise occur during high voltage operations. As such, the cathode SEI 208 can inhibit oxidative reactions in a counterpart manner to the inhibition of reductive reactions by the anode SEI 206. In the illustrated embodiment, the cathode SEI 208 can have a thickness in the sub-micron range, and can include a set of one or more chemical elements corresponding to, or derived from, those present in the set of one or more additives, such as silicon or other heteroatom included in the set of one or more additives. Advantageously, the set of one or more additives can preferentially passivate the cathode 200 and can selectively contribute towards film formation on the cathode 200, rather than the anode 204. Such preferential or selective film formation on the cathode 200 can impart stability against oxidative decomposition, with little or no additional film formation on the anode 204 (beyond the anode SEI 206) that can otherwise degrade battery performance through resistive losses. More generally, the set of one or more additives can decompose below a redox potential of the cathode material and above a redox potential of SEI formation on the anode 204.

Without being bound by a particular theory not recited in the claims, the formation of the cathode SEI 208 can occur through one or more of the following mechanisms:

(1) The set of additive compounds can decompose to form the cathode SEI 208, which inhibits further oxidative decomposition of electrolyte components.

(2) The set of additive compounds can form an intermediate product, such as a complex with $LiPF_6$ or a cathode material, which intermediate product then decomposes to form the cathode SEI 208 that inhibits further oxidative decomposition of electrolyte components.

(3) The set of additive compounds can form an intermediate product, such as a complex with $LiPF_6$, which then decomposes during initial charging. The resulting decomposition product can then further decompose during initial charging to form the cathode SEI 208, which inhibits further oxidative decomposition of electrolyte components.

(4) The set of additive compounds can stabilize the cathode material by preventing metal ion dissolution.

Other mechanisms of action of the electrolyte 202 are contemplated, according to an embodiment of the invention. For example, and in place of, or in combination with, forming or improving the quality of the cathode SEI 208, the set of one or more additives or a derivative thereof (e.g., their decomposition product) can form or improve the quality of the anode SEI 206, such as to reduce the resistance for Li ion diffusion through the anode SEI 206. As another example, the set of one or more additives or a derivative thereof (e.g., their decomposition product) can improve the stability of the electrolyte 202 by chemically reacting or forming a complex with other electrolyte components. As a further example, the set of one or more additives or a derivative thereof (e.g., their decomposition product) can scavenge decomposition products of other electrolyte components or dissolved electrode materials in the electrolyte 202 by chemical reaction or complex formation. Any one or more of the cathode SEI 208, the anode SEI 206, and the other decomposition products or complexes can be viewed as derivatives, which can include a set of one or more chemical elements corresponding to, or derived from, those present in the set of one or more additives, such as silicon or other heteroatom included in the set of additives.

The electrolyte solutions described herein can be conditioned prior to sale or use in a commercial application. For example, batteries including the electrolyte solutions can be conditioned by cycling prior to commercial sale or use in commerce. A method of conditioning a battery can, for example, include conditioning the battery for commercial sale. Such method can include, for example, providing a battery, and cycling such battery through at least 1, at least 2, at least 3, at least 4, or at least 5 cycles, each cycle including charging the battery and discharging the battery at a rate of 0.05 C (e.g., a current of 7.5 mA/g) between 4.95 V and 2.0 V (or another voltage range) versus a reference counterelectrode, such as a graphite anode. Charging and discharging can be carried out at a higher or lower rate, such as at a rate of 0.1 C (e.g., a current of 15 mA/g), at a rate of 0.5 C (e.g., a current of 75 mA/g), or at a rate of IC (e.g., a current of 150 mA/g).

The electrochemical stability of the electrolyte in battery cells can be assessed by measuring the residual current, or the current that passes through the cell after the battery is fully charged or discharged. Residual current can be measured by fully charging the cell and then applying a voltage above the equilibrium potential. As the cell is fully charged, the residual current reflects the extent of electrochemical decomposition of the materials in the cell. A low residual current as compared to control demonstrates enhanced electrochemical stability. Without being bound to a particular theory or mode of action, above the equilibrium potential of the cell the electrochemical decomposition of electrolytes will allow current to flow in a battery cell due at least in part to electron transfer from the negative electrode to the electrolyte and from the electrolyte to the cathode. Additive compounds according to embodiments of the invention improve the performance of electrolytes by any of the mechanisms proposed herein under conditions that may ordinarily cause electrolyte decomposition. Such improvements in electrochemical stability help solve problems present in known electrolyte solutions.

As will be appreciated from the many examples that follow, additive compounds of certain embodiments of the invention improve the performance of conventional electrolytes in high voltage cells both at room temperatures and at high temperatures. Further, compounds of certain embodiments of the invention improve the performance of conventional electrolytes in low voltage cells at high temperatures.

Electrolytes containing certain OMTS additives have shown an improvement in residual current as compared to conventional electrolytes in standard CR2032 (Hohsen) coin cells. The cells were held at 4.5V, 4.9V and 5.1V for 10 hours at 50 degrees C. and the residual current was observed. The lower residual current for the electrolytes containing certain OMTS additives indicates reduction in electrolyte decomposition.

OTMS additives according to certain embodiments improve the coulombic efficiency over the control electrolyte in a high voltage cell. Certain OTMS additives have shown an improvement in coulombic efficiency of as much as about 6% as compared to the control electrolyte.

Certain OTMS additives have shown an improvement of as much as about 19% in room temperature cycle life of a high voltage spinel (LMNO-type) cathode material as compared to the control electrolyte.

NTMS additives according to certain embodiments improve the room temperature cycle life over the control electrolyte in a high voltage cell. Certain NTMS additives have shown an improvement of as much as about 11% in room temperature cycle life of a high voltage spinel (LMNO-type) cathode material as compared to the control electrolyte.

Certain TMS additives according to certain embodiments improve cycle life and coulombic efficiency at higher additive concentrations than those used for certain OTMS and NTMS additives. Certain TMS additives have shown an improvement in coulombic efficiency of as much as about 3% as compared to the control electrolyte. Certain TMS additives have shown an improvement of as much as about 10% in room temperature cycle life of a high voltage spinel (LMNO-type) cathode material as compared to the control electrolyte.

Certain OTMS additives have shown an improvement of as much as about 110% in high temperature cycle life of a high voltage spinel (LMNO-type) cathode material as compared to the control electrolyte. Certain OTMS additives have shown an improvement of as much as about 200% in high temperature cycle life of an LMO-type cathode material as compared to the control electrolyte. Certain OTMS additives improve 1st cycle efficiency and $1^{st}$ cycle reversible capacity in a high voltage spinel (LMNO-type) cathode material as compared to the control electrolyte.

Certain OTMS additives have shown an improvement of as much as about 70% in high temperature cycle life of an NMC-type cathode material as compared to the control electrolyte. OTMS additives according to certain embodiments improve the room temperature cycle life over the control electrolyte in a NMC-type cathode material.

Certain OTMS additives have shown an improvement of as much as about 70% in room temperature cycle life of lithiated layered oxide (OLO-type) cathode materials as compared to the control electrolyte. Certain OTMS additives have shown an improvement of as much as about 130% in high temperature cycle life of high voltage OLO-type cathode materials as compared to the control electrolyte. Certain OTMS additives have shown an improvement of as much as about 2.5% in room temperature energy efficiency of high voltage OLO-type cathode materials as compared to the control electrolyte.

Certain OTMS additives have shown an improvement of as much as about 18% in coulombic efficiency of a high voltage olivine cathode material (CM1-type) as compared to the control electrolyte. Certain OTMS additives have shown an improvement of as much as about 400% in room temperature cycle life of a high voltage CM1-type cathode material as compared to the control electrolyte.

NTMS additives according to certain embodiments improve the room temperature cycle life over the control electrolyte in a high voltage cell. Certain NTMS additives have shown an improvement of as much as about 410% in room temperature cycle life of a high voltage CM1-type cathode material as compared to the control electrolyte.

EXAMPLES

The following examples describe specific aspects of some embodiments of the invention to illustrate and provide a description for those of ordinary skill in the art. The examples should not be construed as limiting the invention, as the examples merely provide specific methodology useful in understanding and practicing some embodiments of the invention.

Example 1

Methodology for Formation and Characterization of Battery Cells Including Stabilizing Additives Battery cells were formed in a high purity argon filled glove box (M-Braun, $O_2$ and humidity content <0.1 ppm). Initially, poly(vinylidene fluoride) (Sigma Aldrich), carbon black (Super P Li, TIMCAL), and a doped $LiCoPO_4$ cathode material $(Li_{(1-x)}:Co_{(1-y-z)}:Fe_y:Ti_z:(PO_4)_{(1-a)})$ were mixed in 1-methyl-2-pyrrolidinone (Sigma Aldrich), and the resulting slurry was deposited on an aluminum current collector and dried to form a composite cathode film. A lithium or graphite anode was used. In case of a graphite anode, a graphitic carbon (mesocarbon microbeads or MCMB) was mixed with poly(vinylidene fluoride) (Sigma Aldrich), carbon black (Super P Li, TIMCAL), using 1-methyl-2-pyrrolidinone (Sigma Aldrich) as a solvent, and the resulting slurry was deposited on a copper current collector and dried to form a composite anode film. Each battery cell including the composite cathode film, a Millipore glass fiber or a polypropylene separator, and the lithium or graphite anode was assembled in a coin cell-type assembly (CR2025, Hohsen). A conventional electrolyte was mixed with a stabilizing additive compound and added to the battery cell. The battery cell was sealed and cycled between a particular voltage range (e.g., about 2 V to about 4.95 V) at a particular temperature (e.g., room temperature or 25° C.).

Example 2

Characterization of Battery Cell Including Stabilizing Additive

Figure 3A:
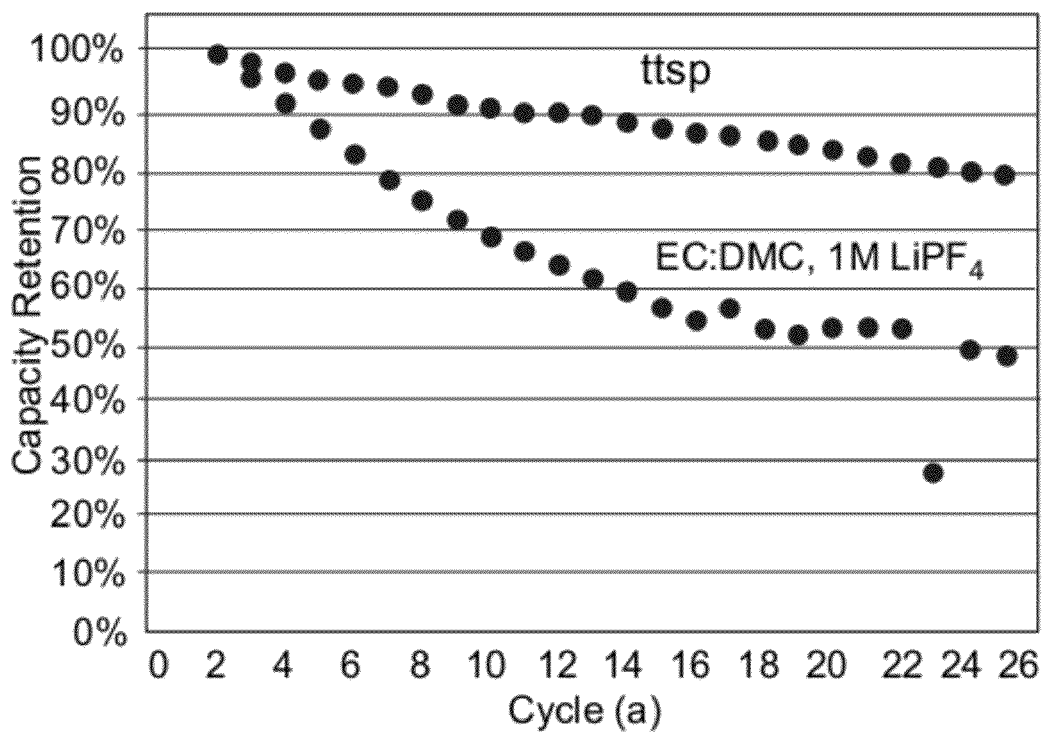
FIG. 3A compares capacity retention with and without a stabilizing additive over several cycles, and FIG. 3B compares coulombic efficiency with and without the stabilizing additive over several cycles, according to an embodiment of the invention.
Figure 3B:
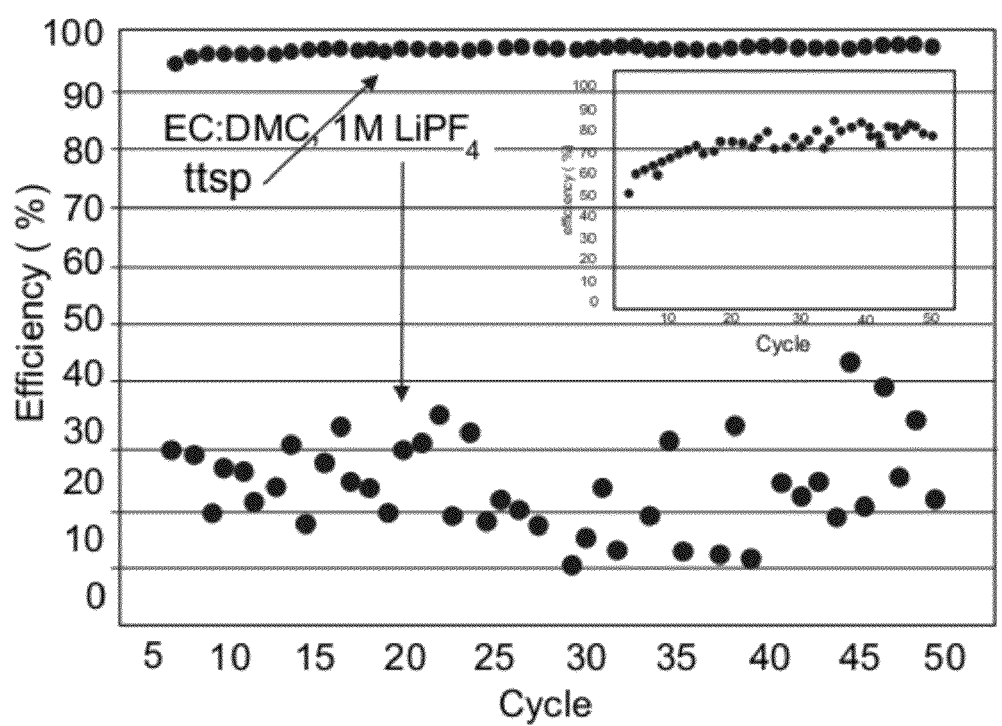

Using the methodology of Example 1, performance characteristics were measured for a test battery cell including about 10 wt. % of tris(trimethylsilyl) phosphate as a stabilizing additive (labeled as "ttsp") dispersed in a conventional electrolyte (ethylene carbonate, dimethyl carbonate, and 1M $LiPF_6$) and for a control battery cell including the conventional electrolyte but without the stabilizing additive (labeled as "EC/DMC, 1M $LiPF_6$"). Each of the test battery cell and the control battery cell included a doped $LiCoPO_4$ cathode material $(Li_{(1-x)}:Co_{(1-y-z)}:Fe_y:Ti_z:(PO_4)_{(1-a)})$. FIG. 3A (top) compares capacity retention with and without the stabilizing additive over several cycles, expressed in terms of a percentage of an initial specific capacity upon discharge retained at a particular cycle. As can be appreciated, the inclusion of the stabilizing additive improved cycle life, retaining about 78% of the initial discharge capacity after 26 cycles (compared to below about 50% without the stabilizing additive). FIG. 3B (bottom) compares coulombic efficiency with and without the stabilizing additive over several cycles, with an inset providing a magnified view of measured values of coulombic efficiency with the stabilizing additive. As can be appreciated, the inclusion of the stabilizing additive improved coulombic efficiency, which increased from an initial value of about 95% and reached a plateau or steady-state value of about 97% (compared to values in the range of about 10% to about 45% without the stabilizing additive).

Example 3

Characterization of Battery Cell Including Stabilizing Additive

Figure 4:
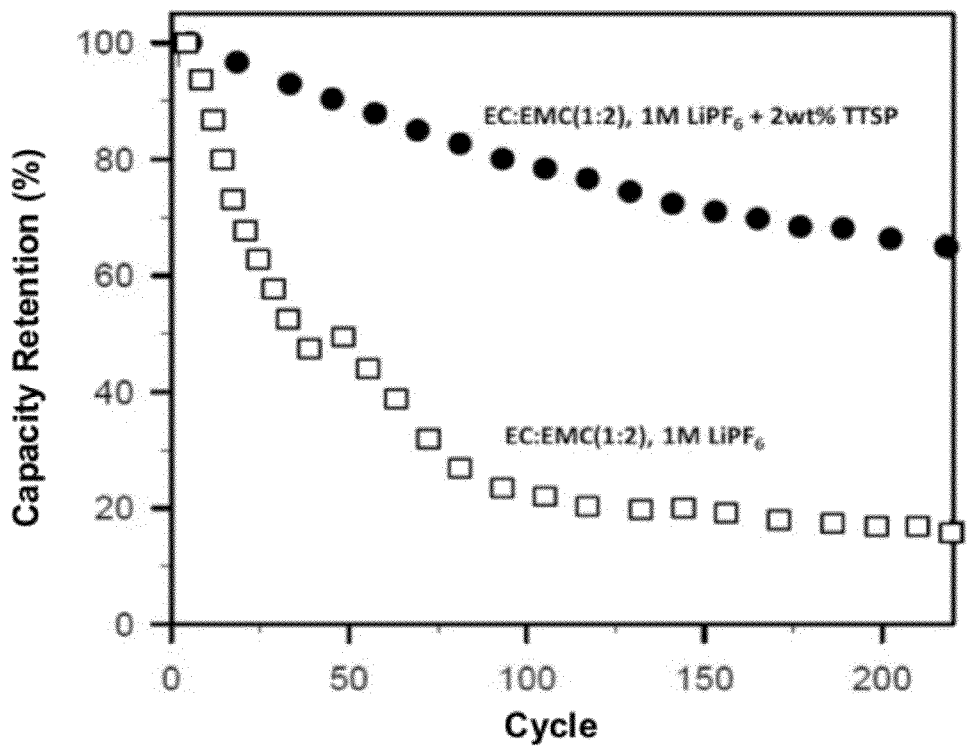
FIG. 4 compares capacity retention with and without a stabilizing additive over several cycles at 25° C., according to an embodiment of the invention.

Using the methodology of Example 1, performance characteristics were measured for a test battery cell including tris(trimethylsilyl) phosphate as a stabilizing additive (labeled as "ttsp") dispersed in a conventional electrolyte (ethylene carbonate, ethyl methyl carbonate, and 1M $LiPF_6$) and for a control battery cell including the conventional electrolyte but without the stabilizing additive (labeled as "EC: EMC, 1M $LiPF_6$"). Each of the test battery cell and the control battery cell included a doped $LiCoPO_4$ cathode material $(Li_{(1-x)}:Co_{(1-y-z)}:Fe_y:Ti_z:(PO_4)_{(1-a)})$, and was cycled between about 2 V to about 4.95 V at a current of about 150 mA/g and at room temperature (25° C.). FIG. 4 compares capacity retention with and without the stabilizing additive over several cycles, expressed in terms of a percentage of an initial specific capacity upon discharge retained at a particular cycle. As can be appreciated, the inclusion of the stabilizing additive improved cycle life, retaining about 80% of the initial discharge capacity after 100 cycles (compared to about 20% without the stabilizing additive) and about 68% of the initial discharge capacity after 200 cycles (compared to under about 20% without the stabilizing additive). The inclusion of the stabilizing additive also improved coulombic efficiency, retaining a value greater than about 98% after 100 cycles or more.

Figure 5:
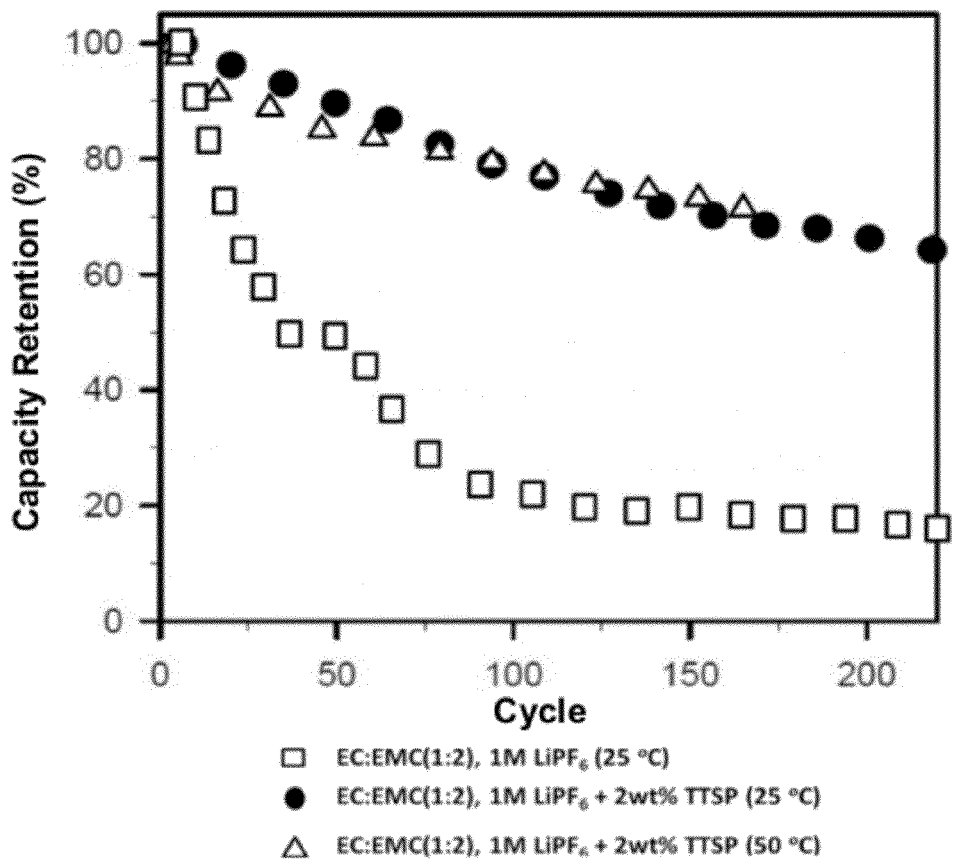
FIG. 5 superimposes results of measurements of capacity retention at 50° C. onto FIG. 4, according to an embodiment of the invention.

To assess stability at elevated temperatures, cycling was also carried out at 50° C. FIG. 5 superimposes results of measurements of capacity retention at 50° C. onto FIG. 4. As can be appreciated, desirable cycle life characteristics are retained at an elevated temperature of 50° C.

Example 4

Characterization of Battery Cell Including Stabilizing Additive

Using the methodology of Example 1, performance characteristics were measured for tris(trimethylsilyl) phosphate as a stabilizing additive dispersed in a conventional electrolyte (ethylene carbonate:ethyl methyl carbonate (1:2) and 1M $LiPF_6$). Each test battery cell included a doped $LiCoPO_4$ cathode material $(Li_{(1-x)}:Co_{(1-y-z)}:Fe_y:Ti_z:(PO_4)_{(1-a)})$ and a graphite anode. Measurements were carried out at different concentrations of the stabilizing additive, namely at about 0.25 wt. %, about 0.5 wt. %, about 1 wt. %, about 2 wt. %, about 10 wt. %, and about 15 wt. %.

Figure 6:
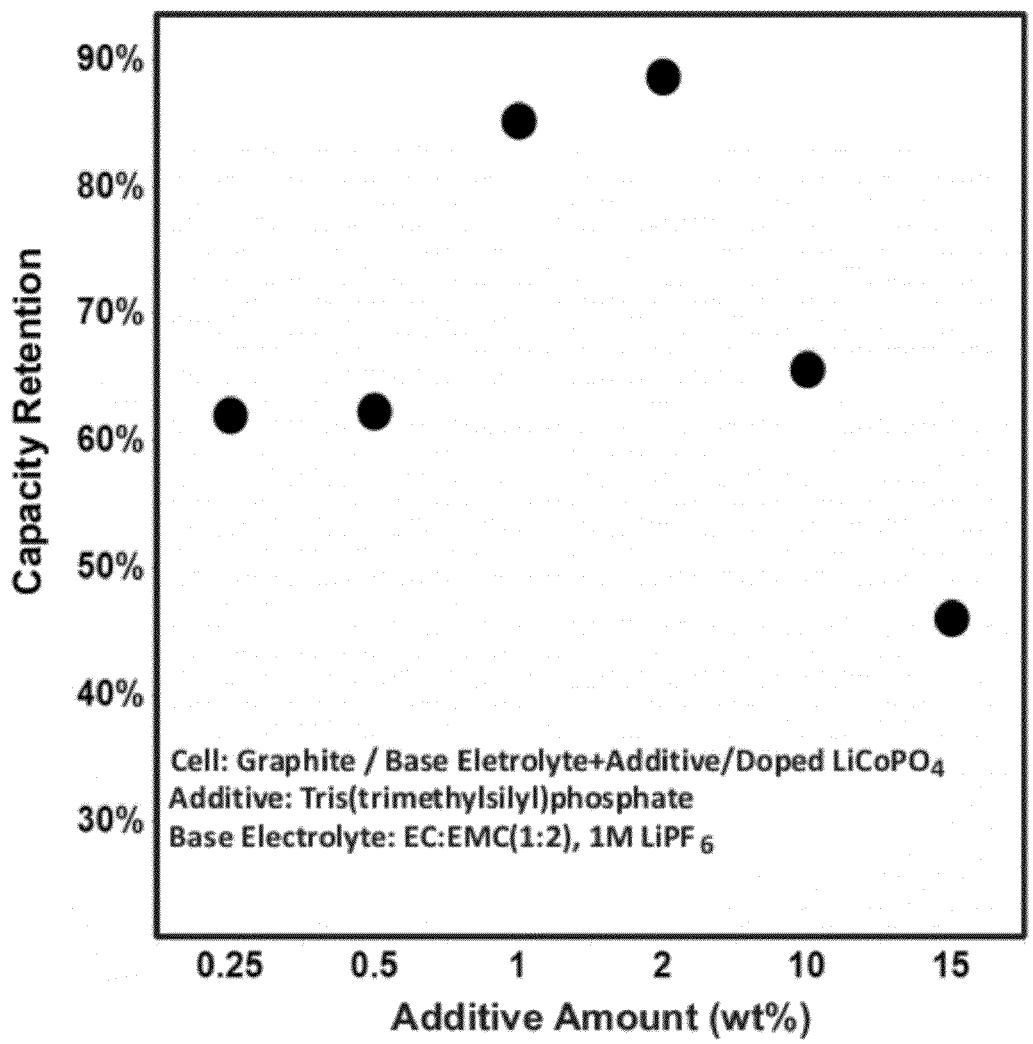
FIG. 6 is a plot of capacity retention at the 50th cycle as a function of concentration of a stabilizing additive, according to an embodiment of the invention.

FIG. 6 is a plot of capacity retention (expressed in terms of a percentage of a specific capacity upon discharge at the $5^{th}$ cycle retained after 50 cycles) as a function of the concentration of the stabilizing additive. As can be appreciated, capacity retention varied with the concentration of the stabilizing additive, ranging from about 60% at a low concentration of the stabilizing additive to about 45% at a high concentration of the stabilizing additive and peaking at about 90% for an intermediate concentration of the stabilizing additive.

Figure 7:
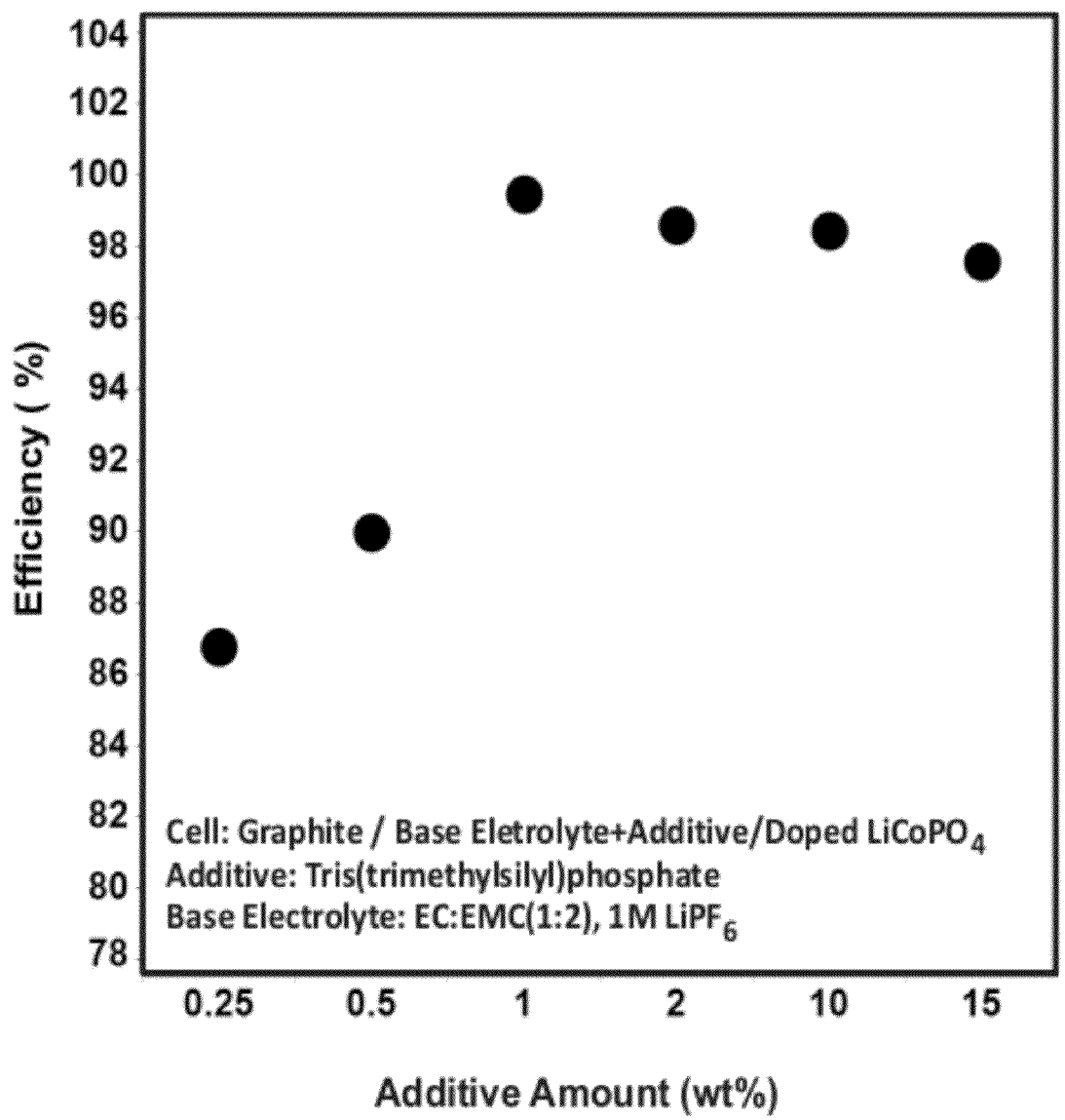
FIG. 7 is a plot of coulombic efficiency at the $50^{th}$ cycle as a function of concentration of a stabilizing additive, according to an embodiment of the invention.

FIG. 7 is a plot of coulombic efficiency at the $50^{th}$ cycle as a function of the concentration of the stabilizing additive. As can be appreciated, coulombic efficiency also varied with the concentration of the stabilizing additive, increasing from about 87% at a low concentration of the stabilizing additive to about 98% for an intermediate concentration of the stabilizing additive and exhibiting a slight decline for higher concentrations of the stabilizing additive.

Example 5

Characterization of Battery Cell Including Stabilizing Additive

Figure 8:
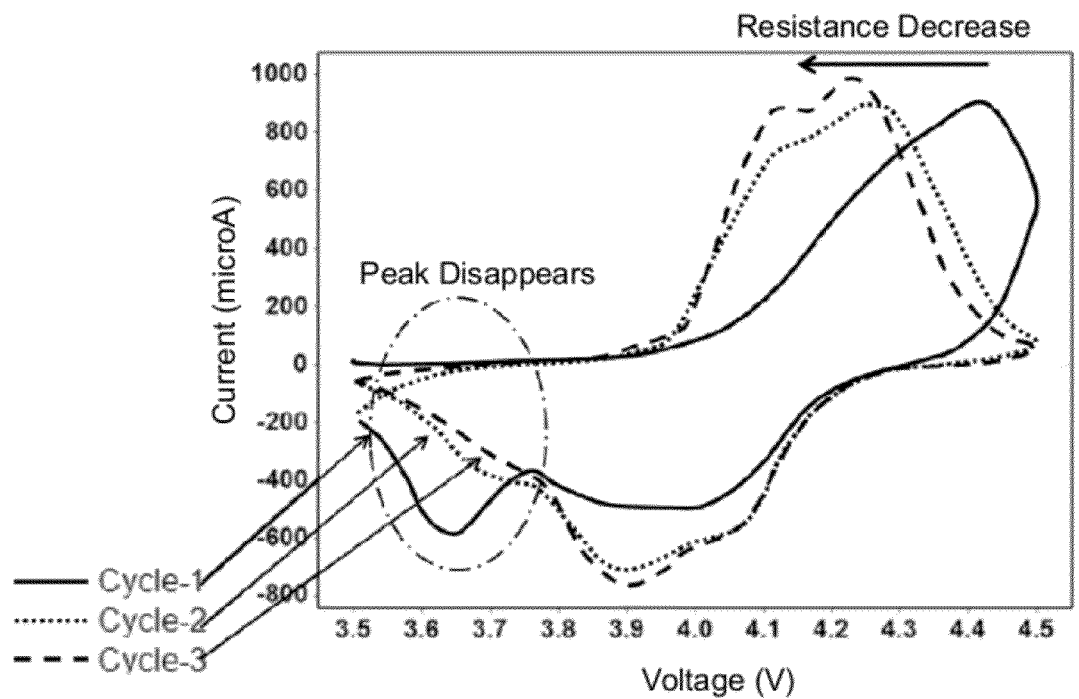
FIG. 8 sets forth superimposed cyclic voltammograms for the $1^{st}$ cycle through the $3^{rd}$ cycle, according to an embodiment of the invention.
Figure 9:
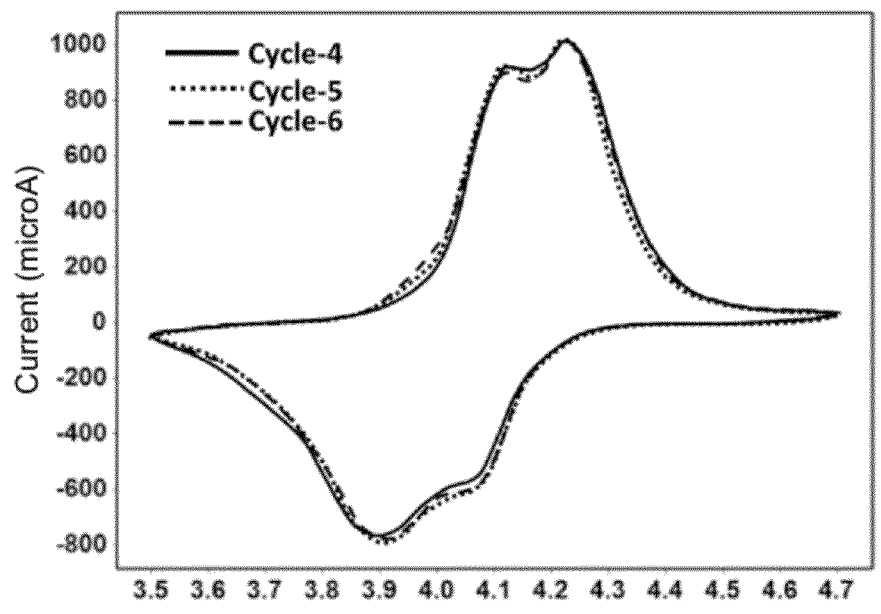
FIG. 9 sets forth superimposed cyclic voltammograms for the $4^{th}$ cycle through the $6^{th}$ cycle, according to an embodiment of the invention.

Using the methodology of Example 1, cyclic voltammetry measurements were carried out for 2 wt. % tris(trimethylsilyl) phosphate as a stabilizing additive dispersed in a conventional electrolyte (ethylene carbonate:ethyl methyl carbonate (1:2) and 1M $LiPF_6$). Measurements were carried out for a battery cell including a $LiMn_2O_4$ cathode and a Li anode. FIG. 8 sets forth superimposed cyclic voltammograms for the $1^{st}$ cycle through the $3^{rd}$ cycle, and FIG. 9 sets forth superimposed cyclic voltammograms for the $4^{th}$ cycle through the $6^{th}$ cycle. As can be appreciated, a large resistance build-up is initially observed during the charge phase of the $1^{st}$ cycle, and this resistance decreases during subsequent cycles (as indicated by the arrow labeled as "Resistance Decrease" in FIG. 8). Also, a peak at about 3.6 V is initially observed during the discharge phase of the $1^{st}$ cycle, and this peak gradually disappears during subsequent cycles (as indicated by the dotted-line oval region labeled as "Peak Disappears" in FIG. 8). Without being bound by a particular theory not recited in the claims, this transient behavior observed in the cyclic voltammograms can be indicative of formation of intermediate products (e.g., derivatives of electrolyte additives) that may be involved (directly or indirectly) in the formation of a protective film (e.g., a cathode SEI) on a cathode.

Example 6

Characterization of Battery Cell Including Stabilizing Additive

Figure 10:
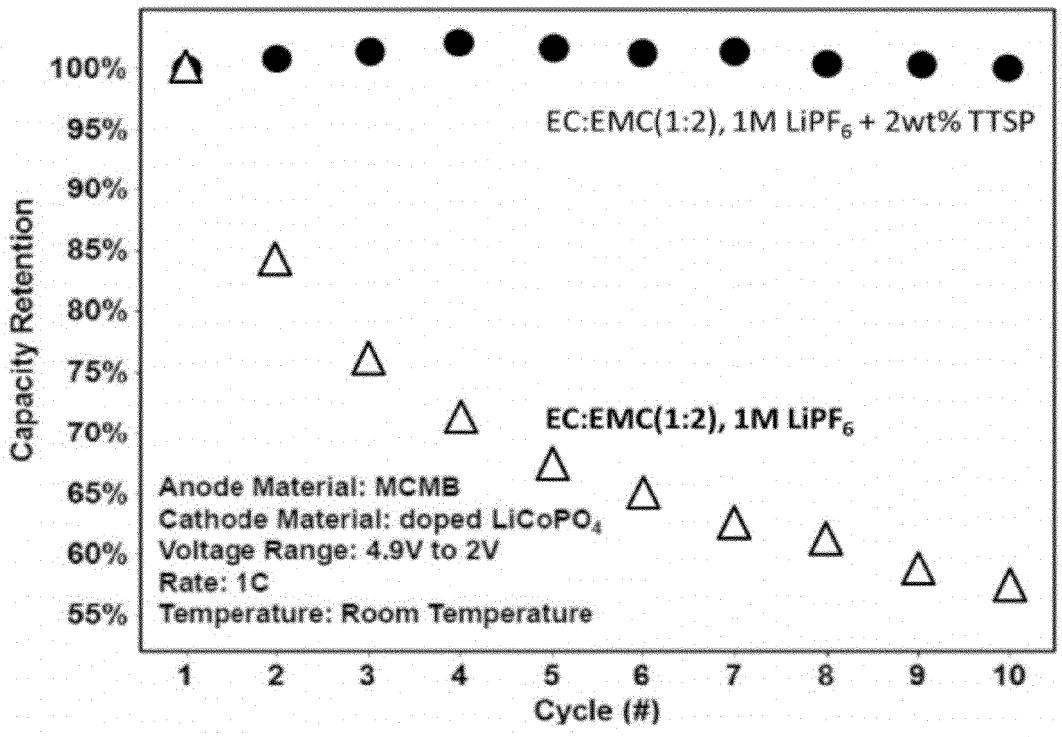
FIG. 10 compares capacity retention with and without a stabilizing additive over several cycles after aging, according to an embodiment of the invention.

Performance characteristics were measured for a test battery cell including tris(trimethylsilyl) phosphate as a stabilizing additive (labeled as "ttsp") dispersed in a conventional electrolyte (ethylene carbonate, ethyl methyl carbonate, and 1M $LiPF_6$) and for a control battery cell including the conventional electrolyte but without the stabilizing additive (labeled as "EC:EMC(1:2), 1M $LiPF_6$"). Each of the test battery cell and the control battery cell included a doped $LiCoPO_4$ cathode material ($Li_{(1-x)}$: $Co_{(1-y-z)}$:$Fe_y$:$Ti_z$:$(PO_4)_{(1-a)}$), was kept in a fully charged state at about 50° C. for 8 days, and was cycled between about 2 V to about 4.95 V at a rate of about 1 C (150 mA/g) and at room temperature (25° C.). FIG. 10 compares capacity retention with and without the stabilizing additive over several cycles, expressed in terms of a percentage of an initial specific capacity upon discharge retained at a particular cycle. As can be appreciated, the inclusion of the stabilizing additive improved cycle life subsequent to aging.

Example 7

Characterization of Battery Cells Including Stabilizing Additive

Figure 11:
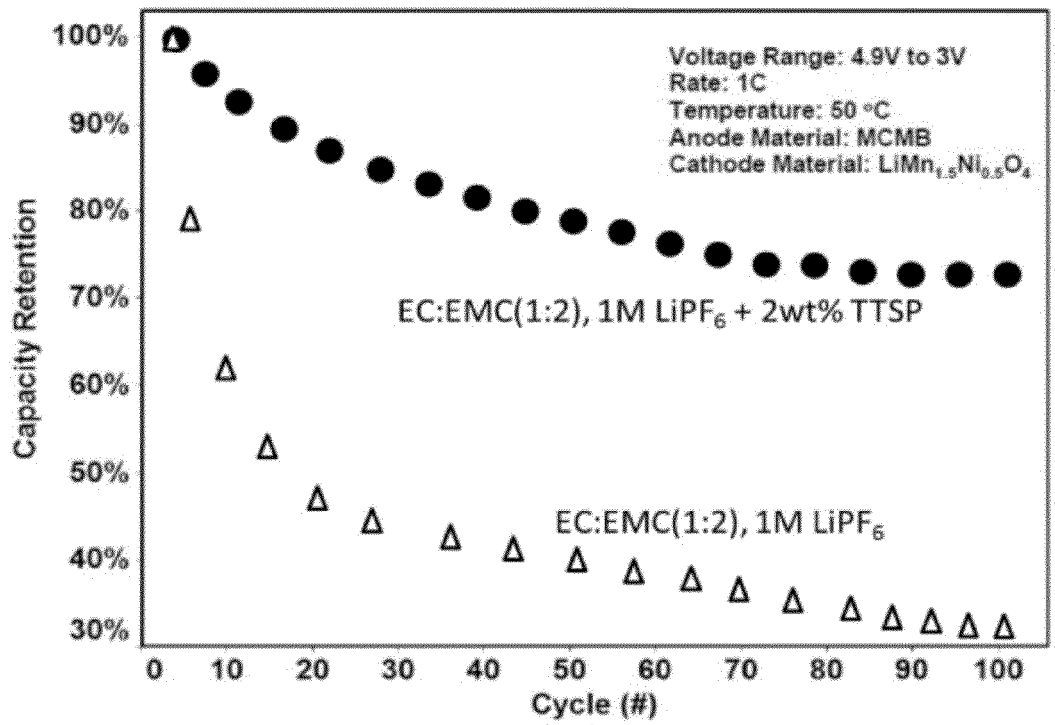
FIG. 11 compares capacity retention with and without a stabilizing additive over several cycles at 50° C. for a $LiMn_{1.5}Ni_{0.5}O_4$ cathode material, according to an embodiment of the invention.

The effectiveness of tris(trimethylsilyl) phosphate as a stabilizing additive was tested for other cathode materials. In one set of tests, performance characteristics were measured for a test battery cell including tris(trimethylsilyl) phosphate as a stabilizing additive (labeled as "ttsp") dispersed in a conventional electrolyte (ethylene carbonate, ethyl methyl carbonate, and 1M $LiPF_6$) and for a control battery cell including the conventional electrolyte but without the stabilizing additive (labeled as "EC:EMC(1:2), 1M $LiPF_6$"). Each of the test battery cell and the control battery cell included a $LiMn_{1.5}Ni_{0.5}O_4$ cathode material, and was cycled between about 3 V to about 4.9 V at a rate of about 1 C and about 50° C., after formation at room temperature. FIG. 11 compares capacity retention with and without the stabilizing additive over several cycles, expressed in terms of a percentage of an initial specific capacity upon discharge retained at a particular cycle. As can be appreciated, the inclusion of the stabilizing additive improved cycle life for the $LiMn_{1.5}Ni_{0.5}O_4$ cathode material.

Figure 12:
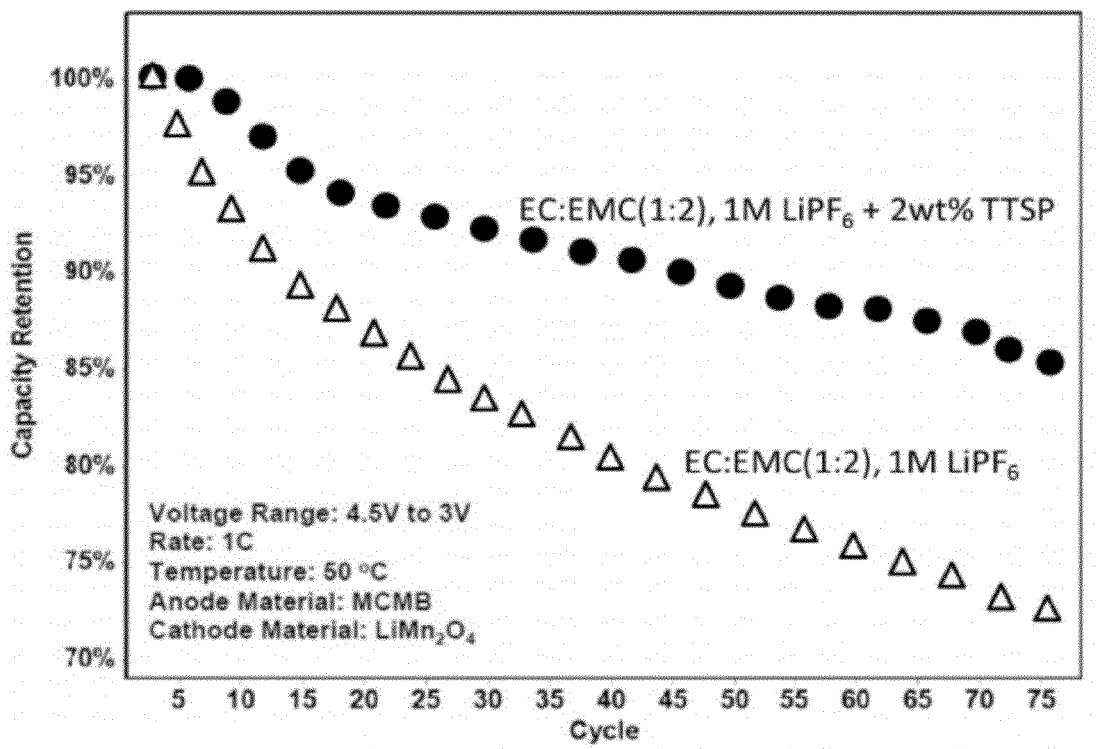
FIG. 12 compares capacity retention with and without a stabilizing additive over several cycles at 50° C. for a $LiMn_2O_4$ cathode material, according to an embodiment of the invention.
Figure 13:
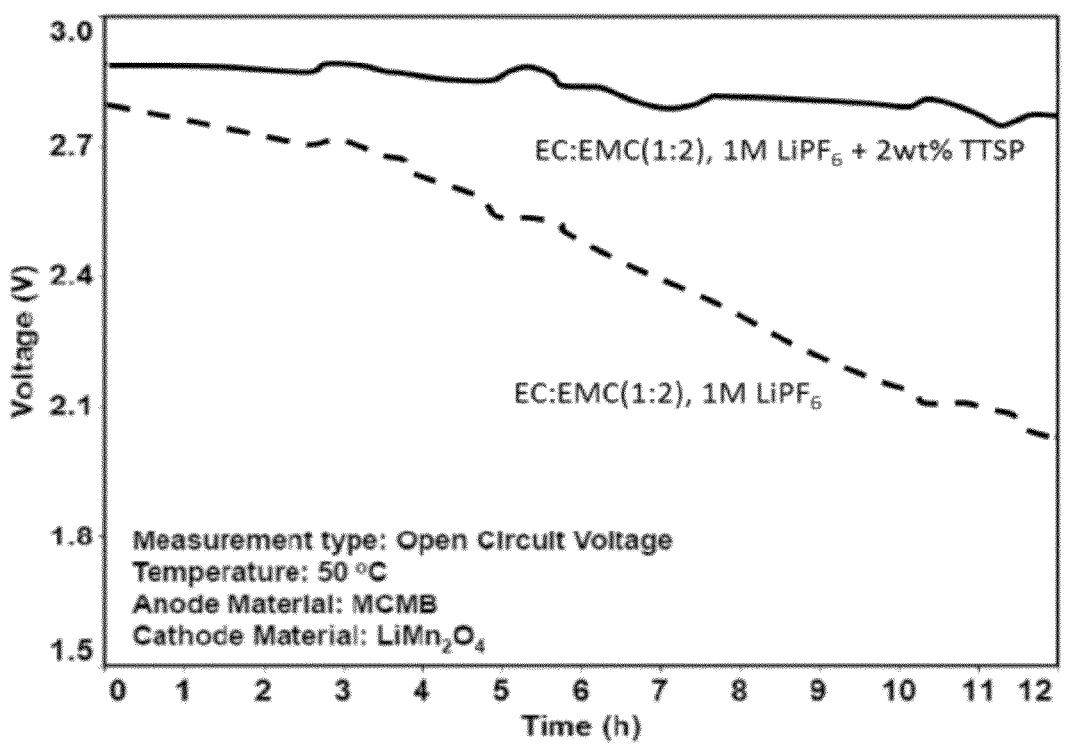
FIG. 13 sets forth open circuit voltage measurements at 50° C., according to an embodiment of the invention.
Figure 14:
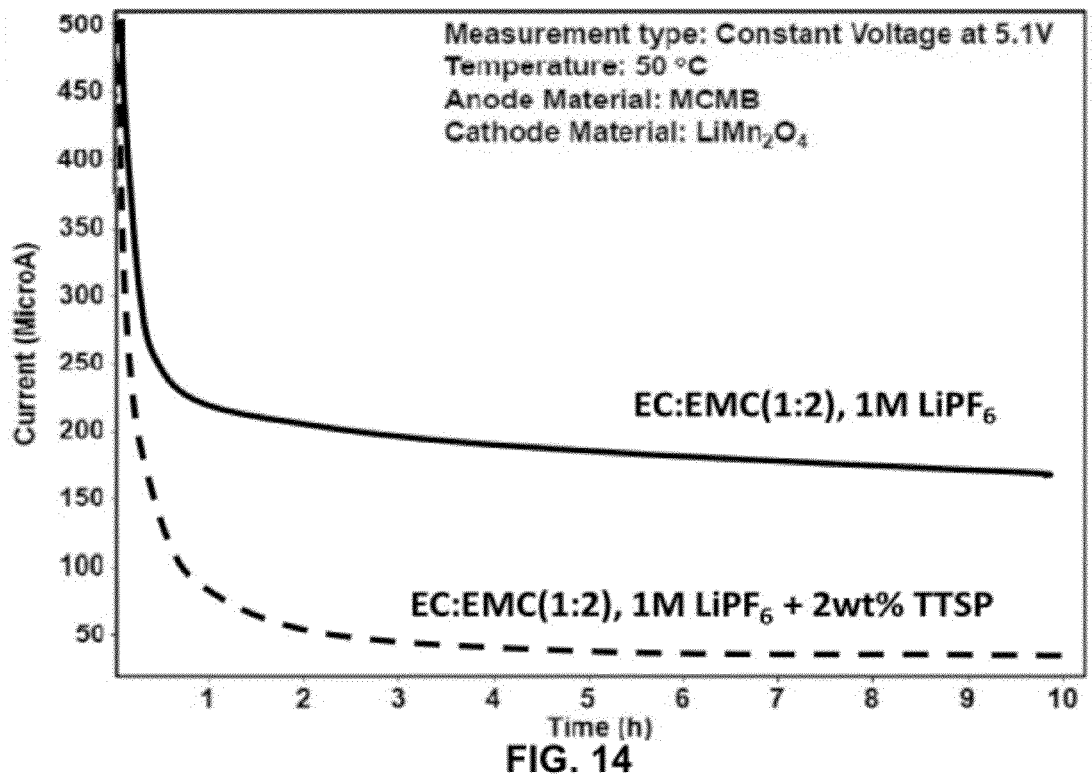
FIG. 14 sets forth residual current measurements at a constant voltage at 50° C., according to an embodiment of the invention.

In another set of tests, performance characteristics were measured for a test battery cell including tris(trimethylsilyl) phosphate as a stabilizing additive (labeled as "ttsp") dispersed in a conventional electrolyte (ethylene carbonate, ethyl methyl carbonate, and 1M $LiPF_6$) and for a control battery cell including the conventional electrolyte but without the stabilizing additive (labeled as "EC:EMC(1:2), 1M $LiPF_6$"). Each of the test battery cell and the control battery cell included a $LiMn_2O_4$ cathode material (about 4.2 V), and was cycled between about 3 V to about 4.5 V at a rate of about 1 C and about 50° C., after formation at room temperature. FIG. 12 compares capacity retention with and without the stabilizing additive over several cycles, expressed in terms of a percentage of an initial discharge capacity retained at a particular cycle. As can be appreciated, the inclusion of the stabilizing additive also improved cycle life for the $LiMn_2O_4$ cathode material. The inclusion of the stabilizing additive also yielded reduced self-discharge and a low residual current for the $LiMn_2O_4$ cathode material, as can be appreciated with reference to FIG. 13 (which sets forth open circuit voltage measurements at about 50° C., after formation at room temperature) and FIG. 14 (which sets forth residual current measurements at a constant voltage of about 5.1 V and at about 50° C.).

Example 8

Characterization of Battery Cells Including Stabilizing Additives

Performance characteristics were measured for various stabilizing additives dispersed in a conventional electrolyte (ethylene carbonate, dimethyl carbonate, and 1M $LiPF_6$). Each test battery cell and each control battery cell included a doped $LiCoPO_4$ cathode material ($Li_{(1-x)}$: $Co_{(1-y-z)}$:$Fe_y$:$Ti_z$: $(PO_4)_{(1-a)}$) and a lithium anode.

Figure 15:
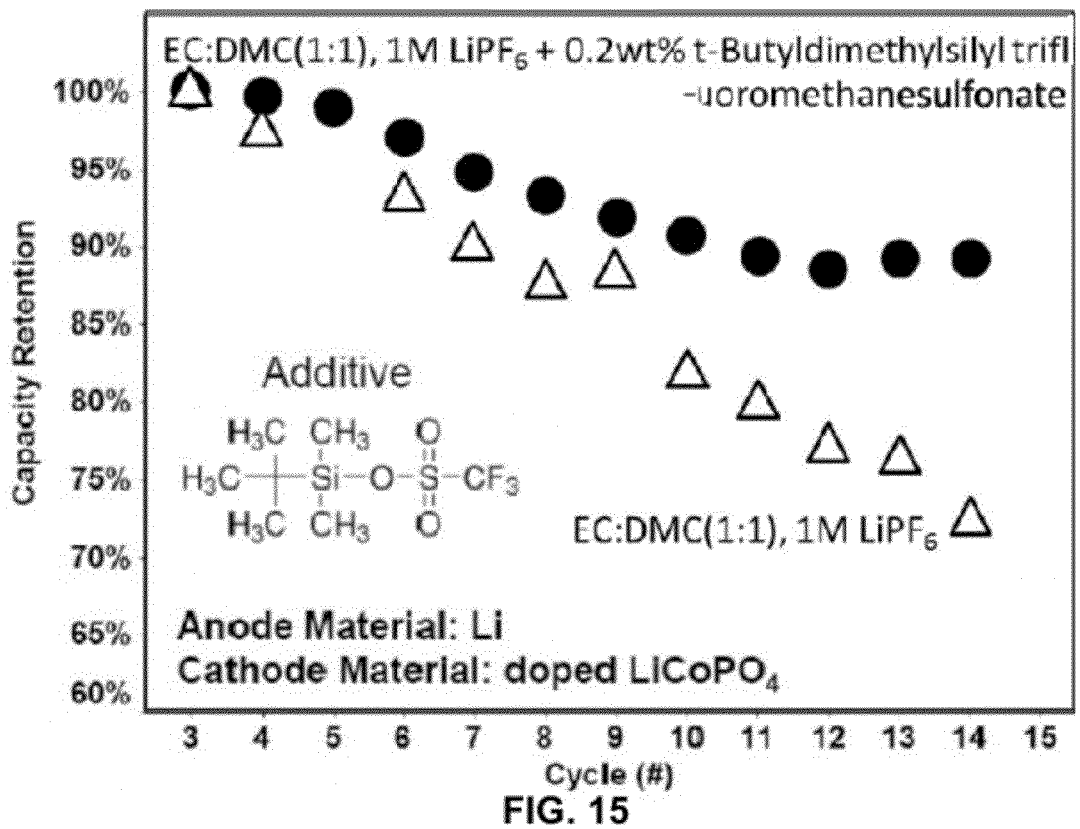
FIG. 15 compares capacity retention with and without a stabilizing additive over several cycles, according to an embodiment of the invention.

FIG. 15 compares capacity retention with and without t-butyldimethylsilyl trifluoromethane sulfonate as a stabilizing additive over several cycles, expressed in terms of a percentage of an initial specific capacity upon discharge retained at a particular cycle. As can be appreciated, the inclusion of the stabilizing additives improved cycle life.

Example 9

Characterization of Battery Cells Including Stabilizing Additives

Figure 16:
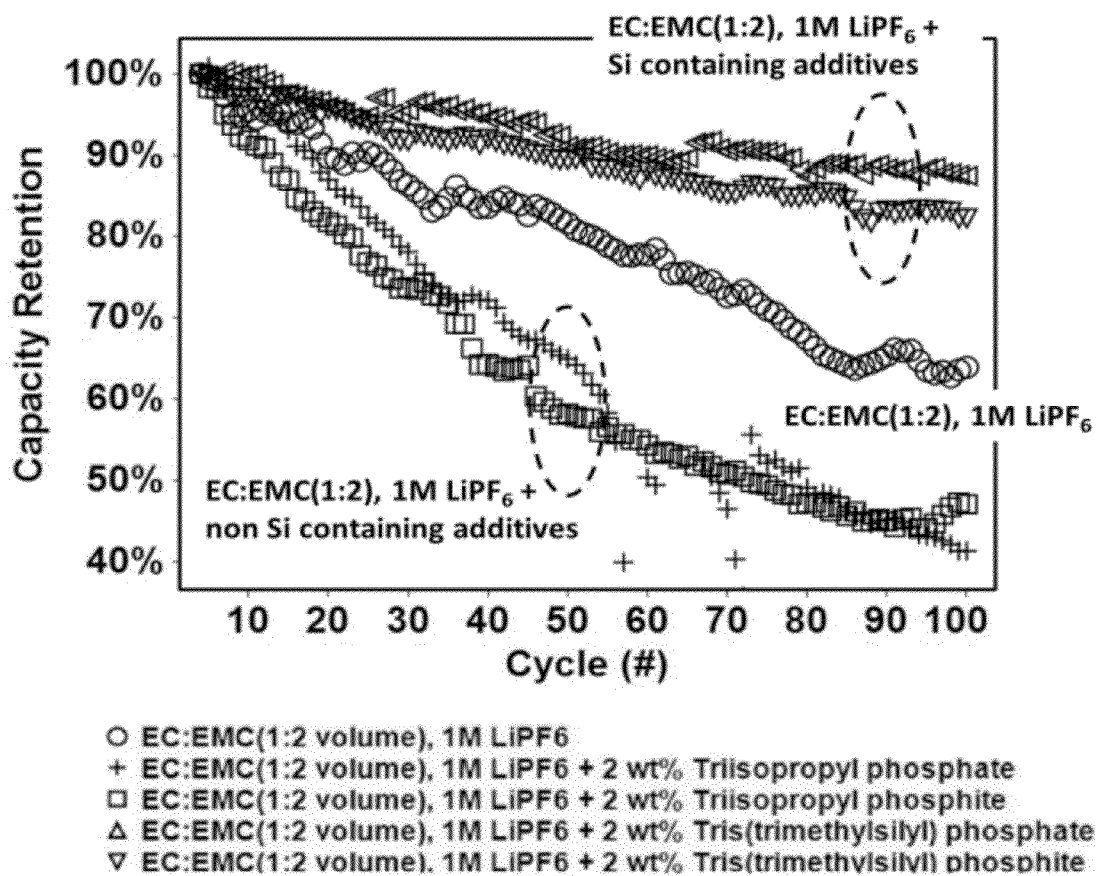
FIG. 16 compares capacity retention with stabilizing additives including silicon and stabilizing additives lacking silicon, according to an embodiment of the invention.

Using the methodology of Example 1, performance characteristics were measured for test battery cells including different stabilizing additives dispersed in a conventional electrolyte (ethylene carbonate, ethyl methyl carbonate, and 1M $LiPF_6$) and for a control battery cell including the conventional electrolyte but without a stabilizing additive. FIG. 16 compares capacity retention of the battery cells over several cycles, expressed in terms of a percentage of an initial specific capacity upon discharge retained at a particular cycle. Two different types of stabilizing additives were used. One type included silicon, and another type lacked silicon. A concentration of the stabilizing additives was about 2 wt. %. As can be appreciated, the inclusion of the silicon-containing stabilizing additives improved cycle life, retaining more than about 80% of the initial discharge capacity after 100 cycles compared to below about 65% without the stabilizing additives. In this example, the non-silicon-containing stabilizing additives deteriorated capacity retention to about 45% after 100 cycles.

Example 10

Characterization of Battery Cells Including Stabilizing Additives

Figure 17:
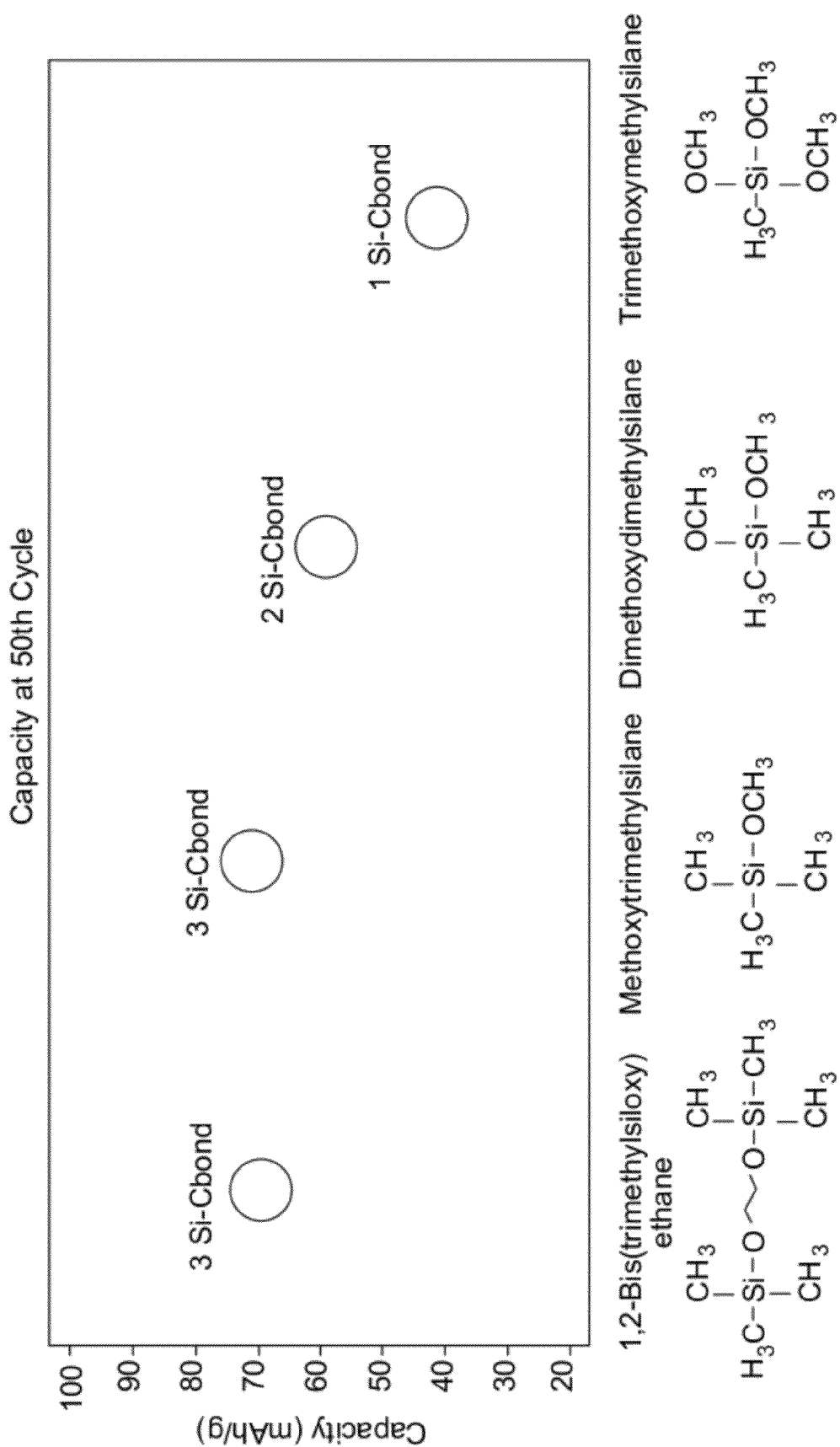
FIG. 17 compares specific capacity upon discharge at the 50 cycle for battery cells including various silicon-containing stabilizing additives, according to an embodiment of the invention.

Using the methodology of Example 1, performance characteristics were measured for silicon-containing stabilizing additives including different numbers of silicon-carbon bonds. FIG. 17 compares specific capacity upon discharge at the 50 cycle for battery cells including the stabilizing additives. As can be appreciated, the inclusion of stabilizing additives including 3 or more silicon-carbon bonds yielded higher discharge capacities at the 50$^{th}$ cycle compared to stabilizing additives including less than 3 silicon-carbon bonds.

Example 11

Characterization of Battery Cells Including Stabilizing Additives

Figure 18:
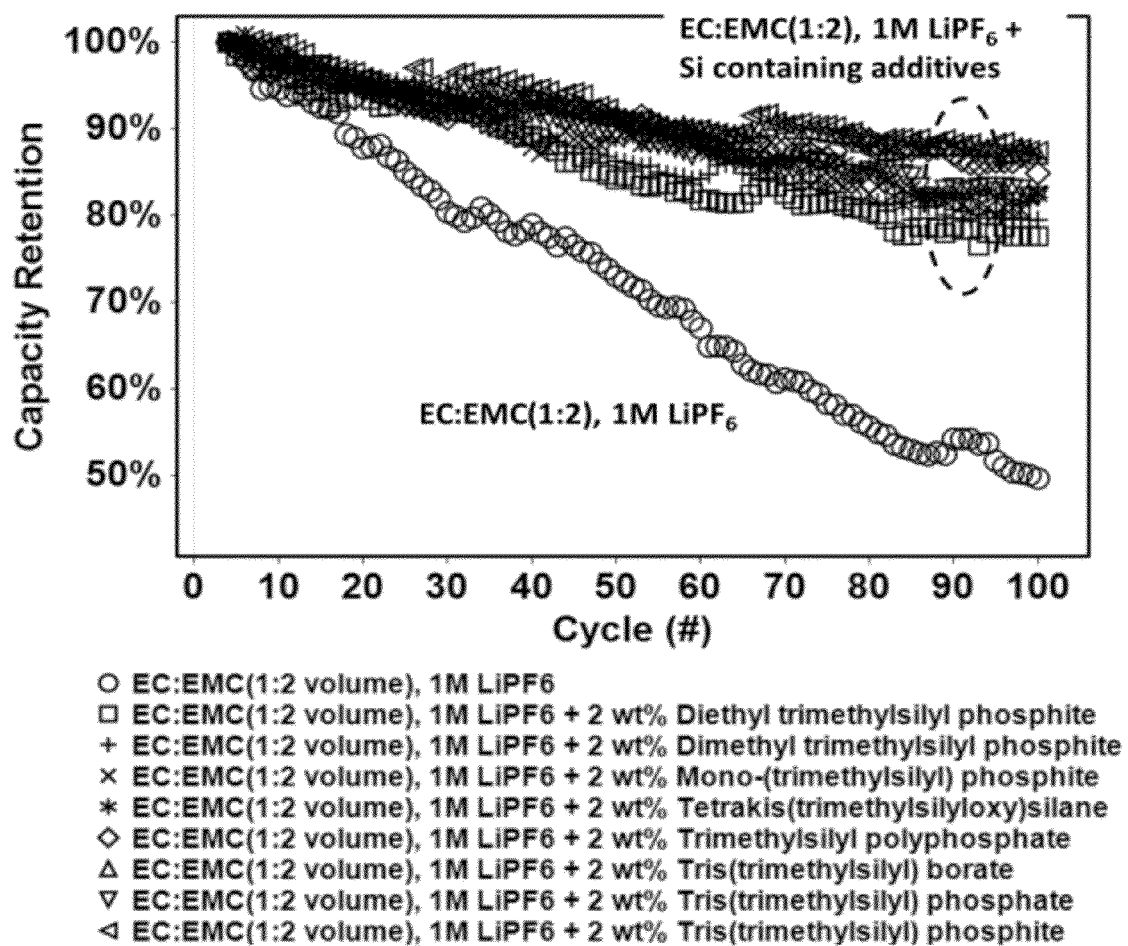
FIG. 18 compares capacity retention of silicon-containing stabilizing additives over several cycles, according to an embodiment of the invention.

Using the methodology of Example 1, performance characteristics were measured for test battery cells including different silicon-containing stabilizing additives dispersed in a conventional electrolyte (ethylene carbonate, ethyl methyl carbonate, and 1M LiPF$_6$) and for a control battery cell including the conventional electrolyte but without a stabilizing additive. Each of the stabilizing additives tested included a Si—O-A moiety, with A=P, B, or Si. FIG. 18 compares capacity retention of the battery cells over several cycles, expressed in terms of a percentage of an initial specific capacity upon discharge retained at a particular cycle. As can be appreciated, the inclusion of each of the stabilizing additives including the Si—O-A moiety improved cycle life.

Example 12

Characterization of Battery Cells Including Stabilizing Additives

Figure 19:
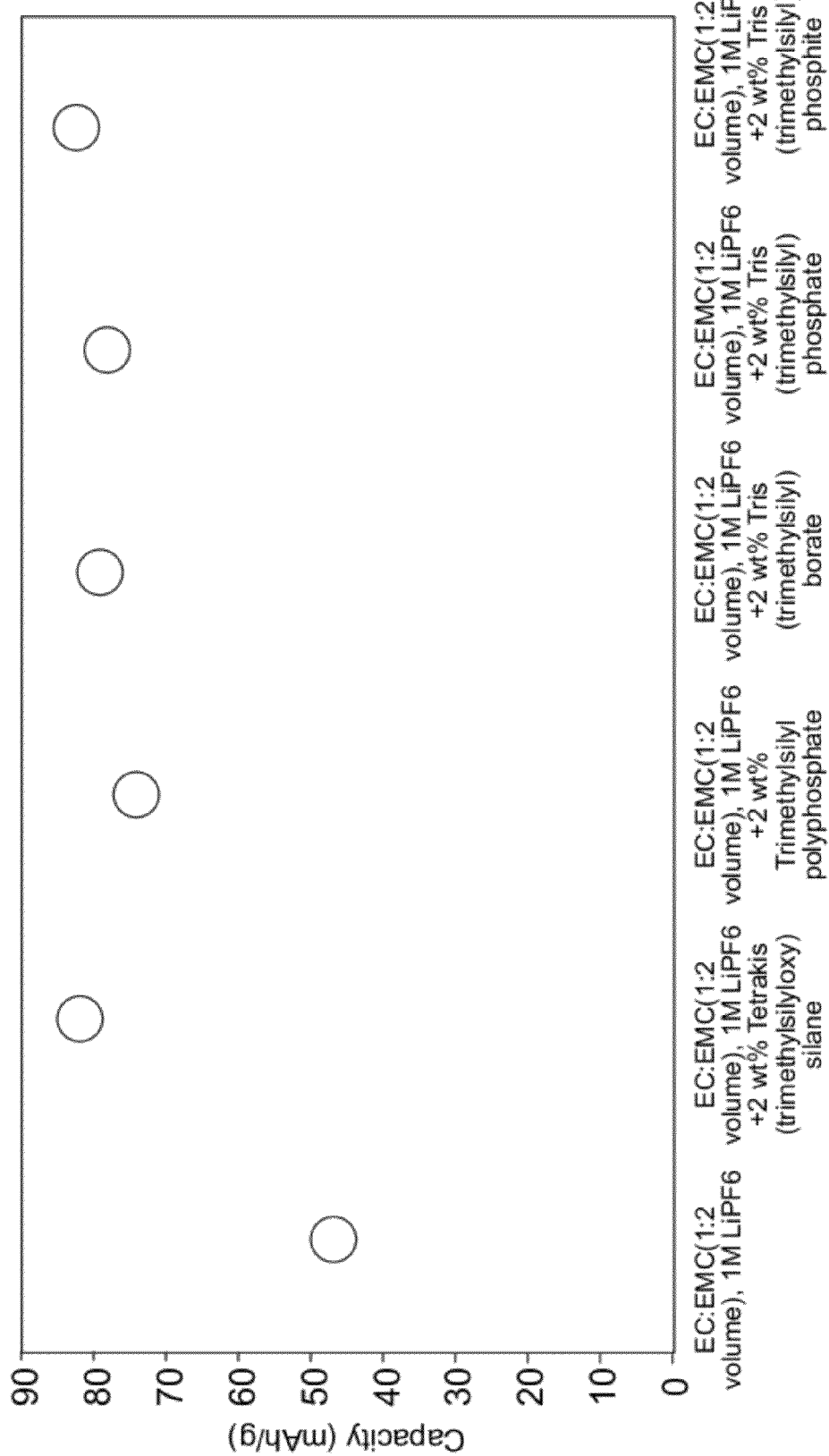
FIG. 19 compares specific capacity upon discharge at the $100^{th}$ cycle with and without silicon-containing stabilizing additives in conventional electrolytes, according to an embodiment of the invention.

Using the methodology of Example 1, performance characteristics were measured for test battery cells including different silicon-containing stabilizing additives dispersed in a conventional electrolyte (ethylene carbonate, ethyl methyl carbonate, and 1M LiPF$_6$) and for a control battery cell including the conventional electrolyte but without a stabilizing additive. FIG. 19 compares specific capacity upon discharge at the 100$^{th}$ cycle for the battery cells. A concentration of the stabilizing additives was about 2 wt. %. As can be appreciated, the inclusion of the silicon-containing stabilizing additives improved discharge capacity.

Example 13

Characterization of Battery Cells Including Stabilizing Additives

Figure 20:
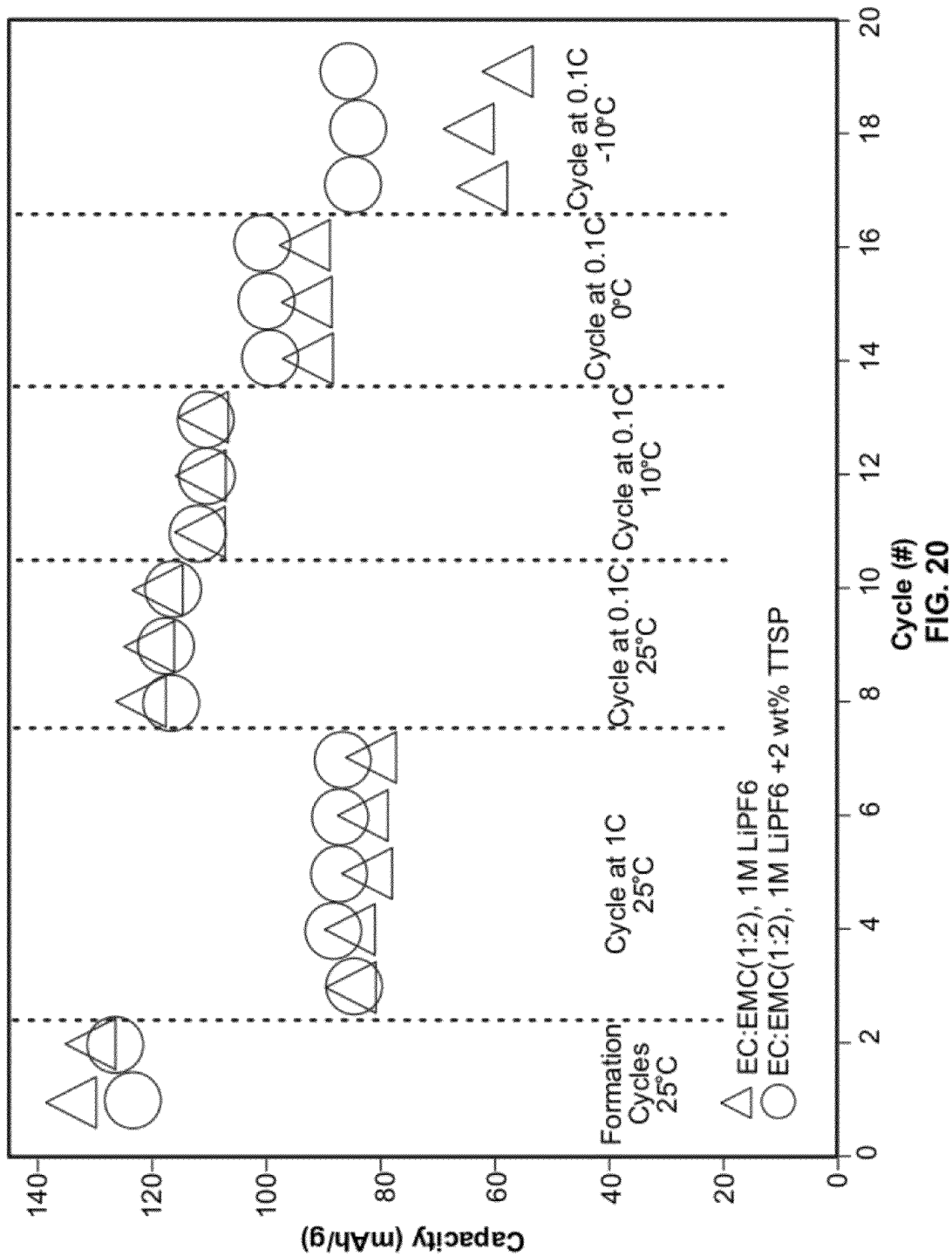
FIG. 20 compares specific capacity upon discharge at different temperatures with and without a silicon-containing stabilizing additive, according to an embodiment of the invention.

Using the methodology of Example 1, performance characteristics were measured for battery cells including about 2 wt. % tris(trimethylsilyl) phosphate as a stabilizing additive (labeled as "TTSP") dispersed in a conventional electrolyte (ethylene carbonate, ethyl methyl carbonate, and 1M LiPF$_6$) and including the conventional electrolyte but without the stabilizing additive (labeled as "EC:EMC (1:2), 1M LiPF$_6$"). To assess stability at reduced temperatures, cycling was carried out at about 10° C., about 0° C., and about −10° C., after initial cycling at room temperature (25° C.). FIG. 20 compares specific capacity upon discharge of the battery cells over several cycles at different temperatures. As can be appreciated, the inclusion of the stabilizing additive improved discharge capacity at temperatures below room temperature.

Example 14

Characterization of Battery Cells Including Stabilizing Additives

Figure 21:
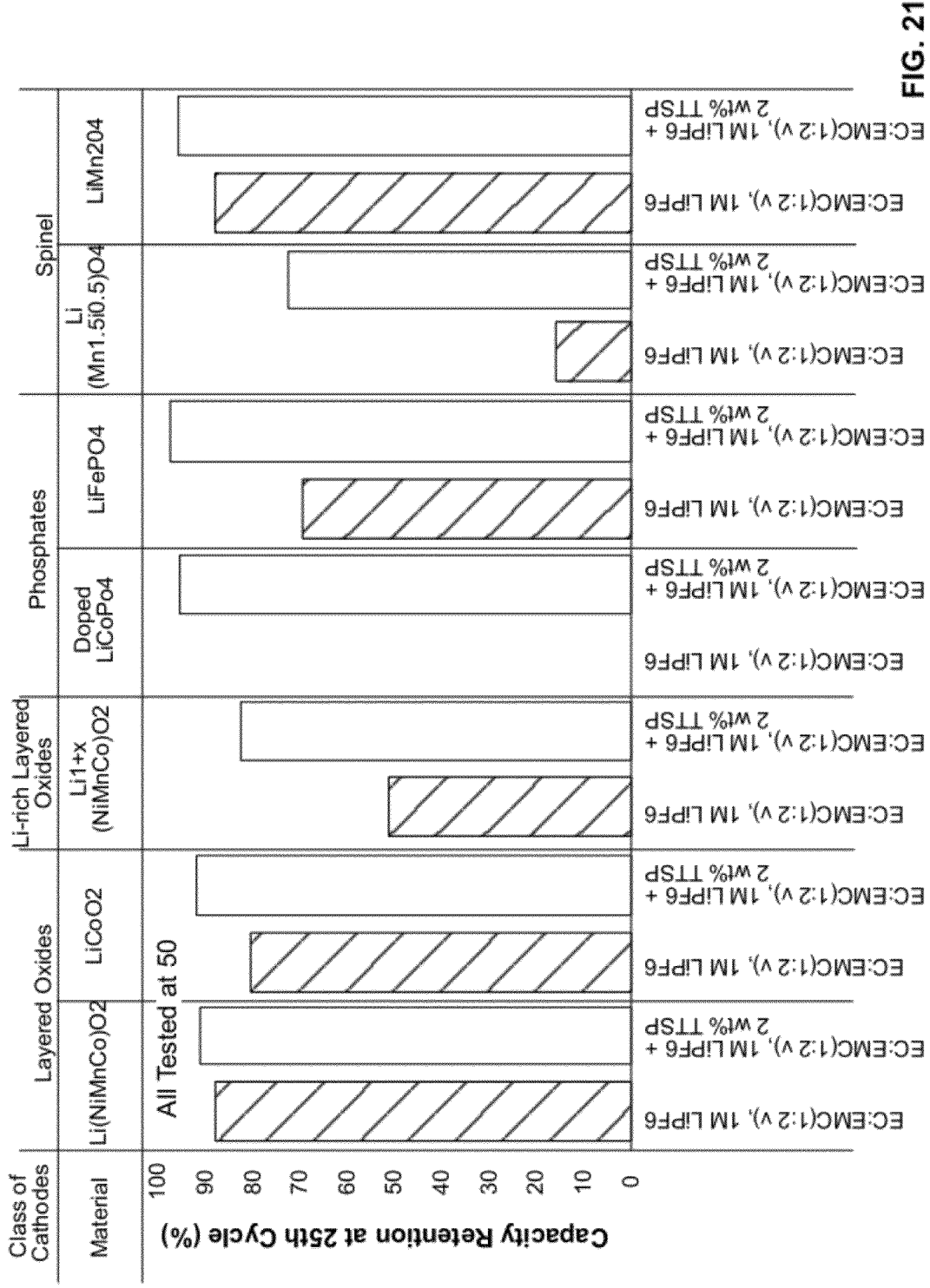
FIG. 21 compares capacity retention at the $25^{th}$ cycle with and without a silicon-containing stabilizing additive for various cathode materials, according to an embodiment of the invention.

Using the methodology of Example 1, the effectiveness of tris(trimethylsilyl) phosphate as a stabilizing additive was tested for various cathode materials at an elevated temperature of about 50° C. FIG. 21 compares capacity retention at the 25$^{th}$ cycle for battery cells including about 2 wt. % of the stabilizing additive (labeled as "TTSP") dispersed in a conventional electrolyte (ethylene carbonate, ethyl methyl carbonate, and 1M LiPF$_6$) and including the conventional electrolyte but without the stabilizing additive (labeled as "EC:EMC (1:2 v), 1M LiPF$_6$"). As can be appreciated, the inclusion of the stabilizing additive improved capacity retention for each cathode material.

Example 15

Characterization of Battery Cells Including Stabilizing Additives

Figure 22:
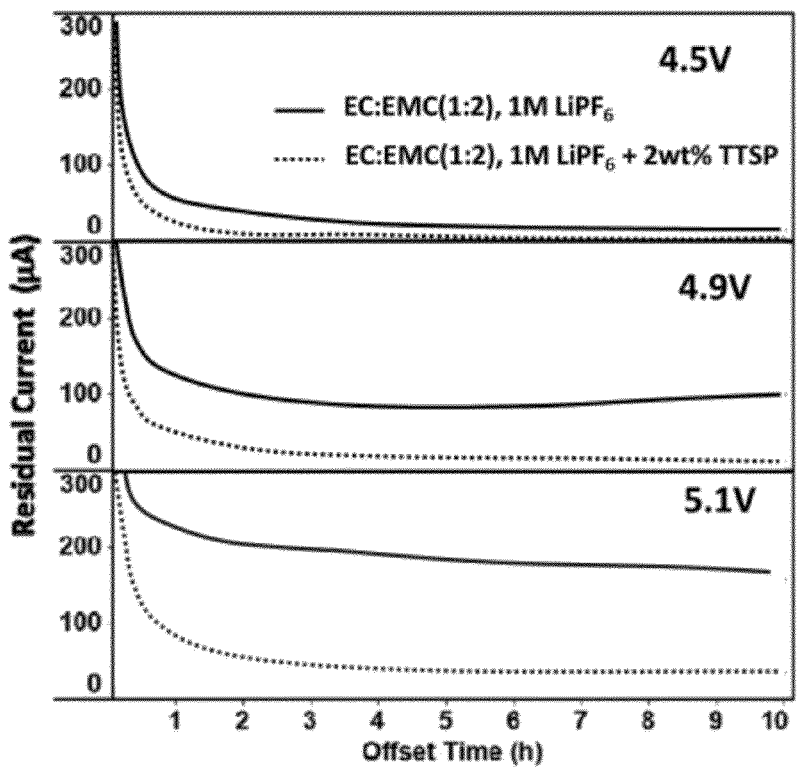
FIG. 22 sets forth residual current measurements for battery cells held at about 4.5V, about 4.9V, and about 5.1V for about 10 hours at 50 degrees C., according to an embodiment of the invention.

LiMn$_2$O$_4$ cathode films were assembled in half cells (including Li metal as an anode) in a coin cell-type assembly (CR2025, Hohsen). One cell included a conventional electrolyte (ethylene carbonate, ethyl methyl carbonate, and 1M LiPF$_6$) with tris(trimethylsilyl)phosphate (labeled as "TTSP") as a stabilizing additive, and another cell included the conventional electrolyte without the stabilizing additive (labeled as "EC:EMC (1:2), 1M LiPF$_6$"). The cells were held at about 4.5V, about 4.9V, and about 5.1V for about hours at 50° C., and their residual currents were measured, with results illustrated in FIG. 22. As can be appreciated, the cells including tris(trimethylsilyl)phosphate had lower residual currents, which is indicative of a reduction in electrolyte decomposition.

Example 16

Characterization of Battery Cells Including Stabilizing Additives

Figure 23:
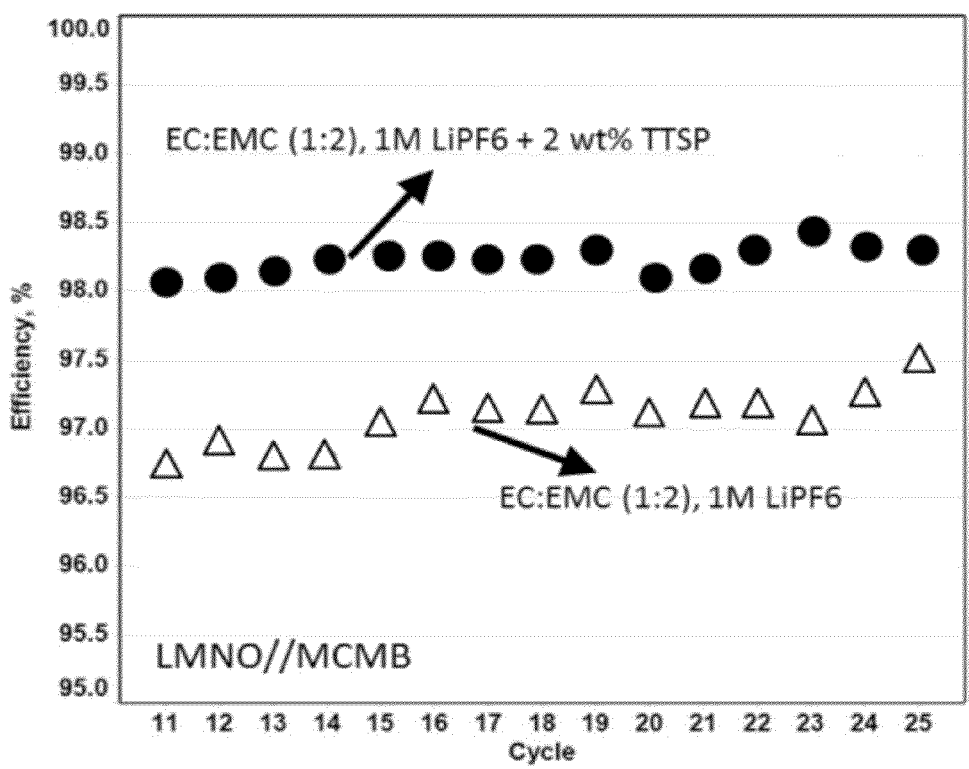
FIG. 23 compares coulombic efficiency with and without a stabilizing additive over several cycles for a $LiMn_{1.5}Ni_{0.5}O_4$ cathode material, according to an embodiment of the invention.

Battery cells each including a LiMn$_{1.5}$Ni$_{0.5}$O$_4$ cathode material and a graphite anode (MCMB) were assembled using the methodology of Example 1. One cell included a conventional electrolyte (ethylene carbonate, ethyl methyl carbonate, and 1M LiPF$_6$) with tris(trimethylsilyl)phosphate (labeled as "TTSP") as a stabilizing additive, and another cell included the conventional electrolyte without the stabilizing additive (labeled as "EC:EMC (1:2), 1M LiPF$_6$"). The cells were cycled at a rate of about 0.1 C for several cycles, and their coloumbic efficiency was measured at every cycle, with results illustrated in FIG. 23. As can be appreciated, the inclusion of tris(trimethylsilyl)phosphate improved coulombic efficiency.

Example 17

Characterization of Battery Cells Including Stabilizing Additives

Figure 24:
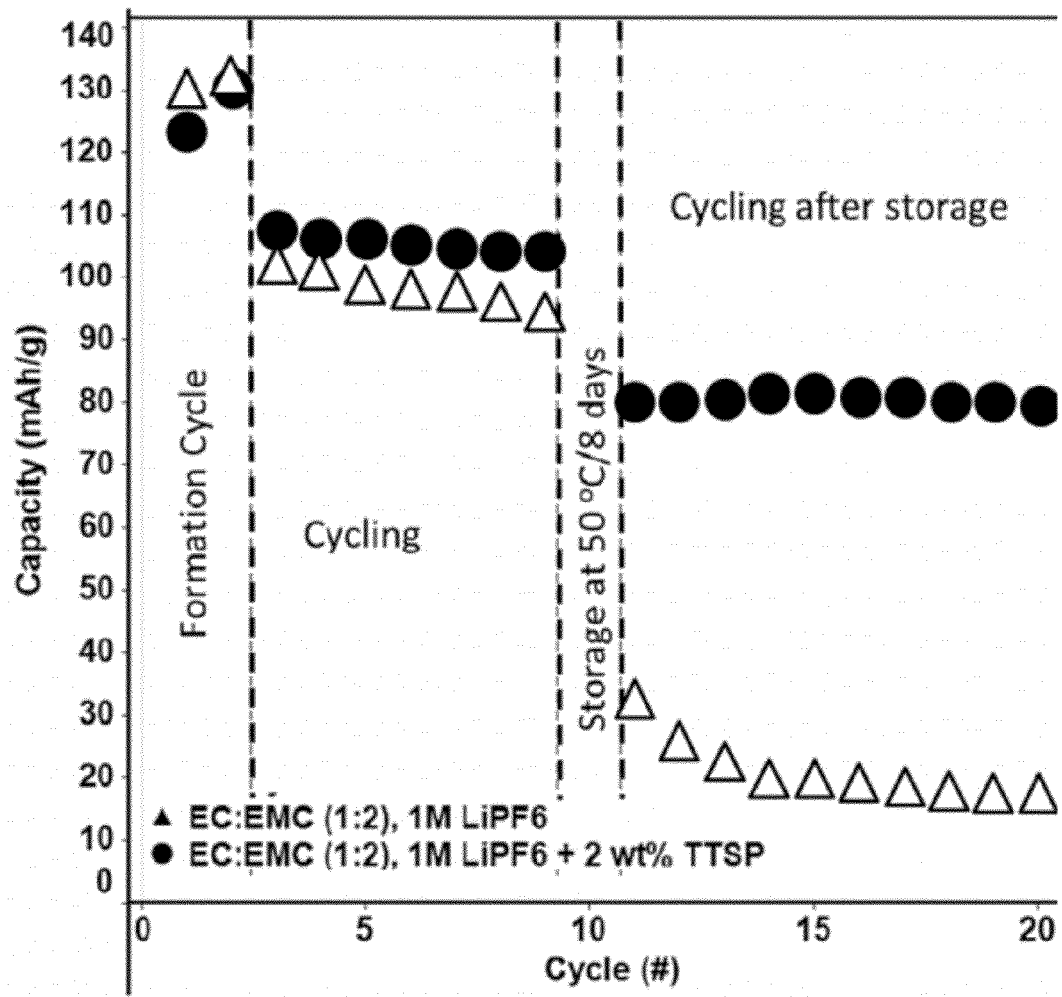
FIG. 24 compares specific capacity upon discharge with and without a stabilizing additive over several cycles after storage at 50 degrees C. for 8 days for a doped $LiCoPO_4$ cathode material, according to an embodiment of the invention.

Battery cells each including a doped LiCoPO$_4$ cathode material and a graphite anode (MCMB) were assembled using the methodology of Example 1. One cell included a conventional electrolyte (ethylene carbonate, ethyl methyl carbonate, and 1M LiPF$_6$) with tris(trimethylsilyl)phosphate (labeled as "TTSP") as a stabilizing additive, and another cell included the conventional electrolyte without the stabilizing additive (labeled as "EC:EMC (1:2), 1M LiPF$_6$"). The cells were initially cycled at room temperature (25° C.) and were then stored at about 50° C. for 8 days in a charged state. Subsequently, the cells were cooled to room temperature and cycled again. FIG. 24 compares specific capacity upon discharge with and without the stabilizing additive over several cycles. As can be appreciated, the inclusion of tris(trimethylsilyl)phosphate improved discharge capacity subsequent to storage at high temperatures, thereby demonstrating enhanced thermal stability of the electrolyte and/or battery cells.

Example 18

Characterization of Battery Cells Including Stabilizing Additives

Figure 25:
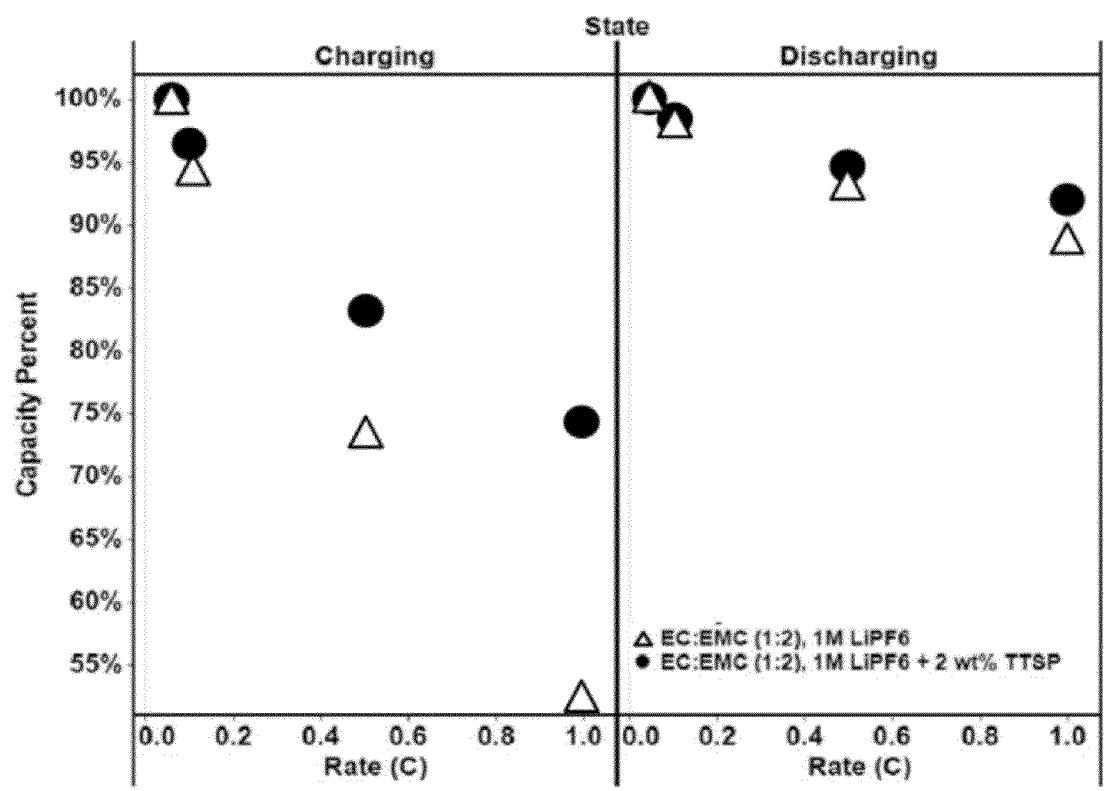
FIG. 25 compares capacity retention with and without a stabilizing additive at different charging and discharging rates, according to an embodiment of the invention.

Battery cells each including a doped $LiCoPO_4$ cathode material ($Li_{(1-x)}$:$Co_{(1-y-z)}$:$Fe_y$:$Ti_z$:$(PO_4)_{(1-a)}$) and a graphite anode (MCMB) were assembled using the methodology of Example 1. One cell included a conventional electrolyte (ethylene carbonate, ethyl methyl carbonate, and 1M $LiPF_6$) with tris(trimethylsilyl)phosphate (labeled as "TTSP") as a stabilizing additive, and another cell included the conventional electrolyte without the stabilizing additive (labeled as "EC:EMC (1:2), 1M $LiPF_6$"). Signature rate test was carried out at the $101^{st}$ cycle, and rate capability of the battery cells was measured. FIG. 25 compares capacity retention of the battery cells at different charging and discharging rates, expressed in terms of a percentage of a low rate (0.05 C) specific capacity retained at a particular rate. As can be appreciated, the inclusion of tris(trimethylsilyl)phosphate improved rate capability both during charging and discharging.

Example 19

Characterization of Battery Cells Including Stabilizing Additives

Figure 26:
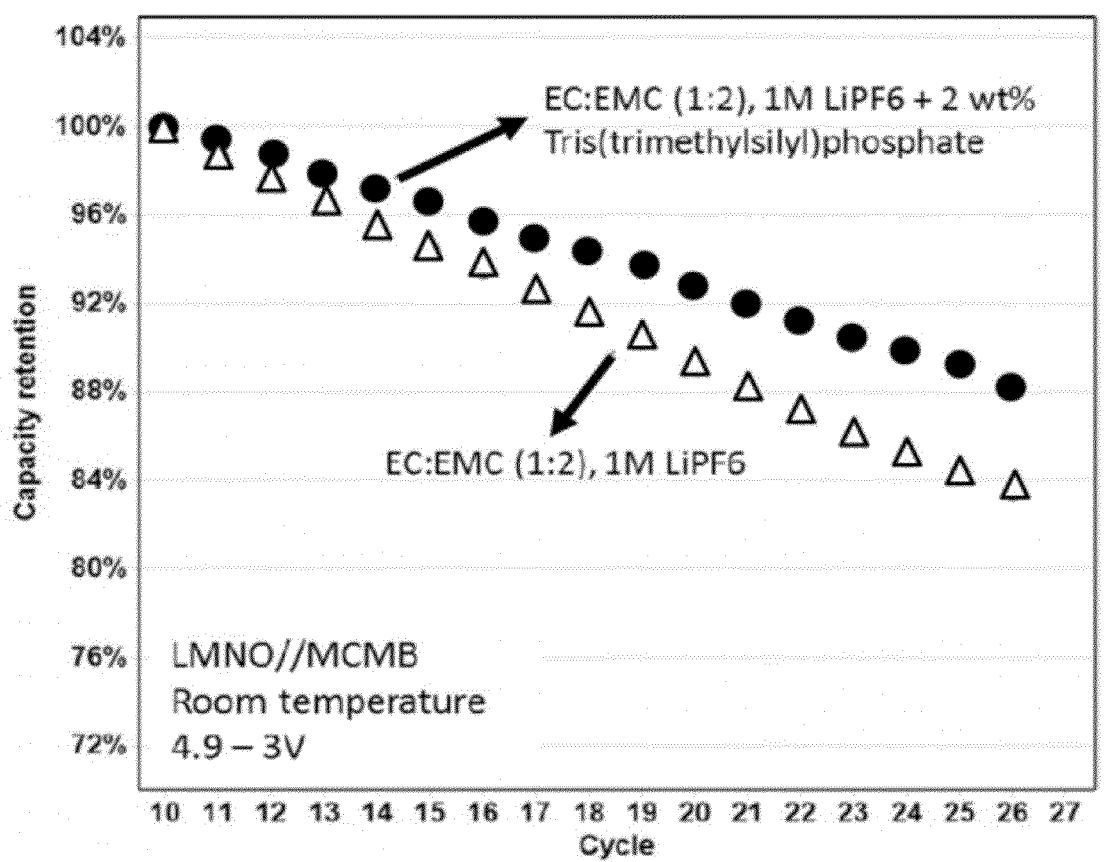
FIG. 26 compares capacity retention with and without a stabilizing additive at room temperature for a $LiMn_{1.5}Ni_{0.5}O_4$ cathode material, according to an embodiment of the invention.

Battery cells each including a $LiMn_{1.5}Ni_{0.5}O_4$ cathode material and a graphite anode (MCMB) were assembled using the methodology of Example 1. One cell included a conventional electrolyte (ethylene carbonate, ethyl methyl carbonate, and 1M $LiPF_6$) with tris(trimethylsilyl)phosphate as a stabilizing additive, and another cell included the conventional electrolyte without the stabilizing additive (labeled as "EC:EMC (1:2), 1M $LiPF_6$"). The cells were cycled at a rate of about 0.1 C for several cycles. FIG. 26 compares capacity retention with and without the stabilizing additive. As can be appreciated, the inclusion of tris(trimethylsilyl)phosphate improved capacity retention.

Example 20

Characterization of Battery Cells Including Stabilizing Additives

Figure 27:
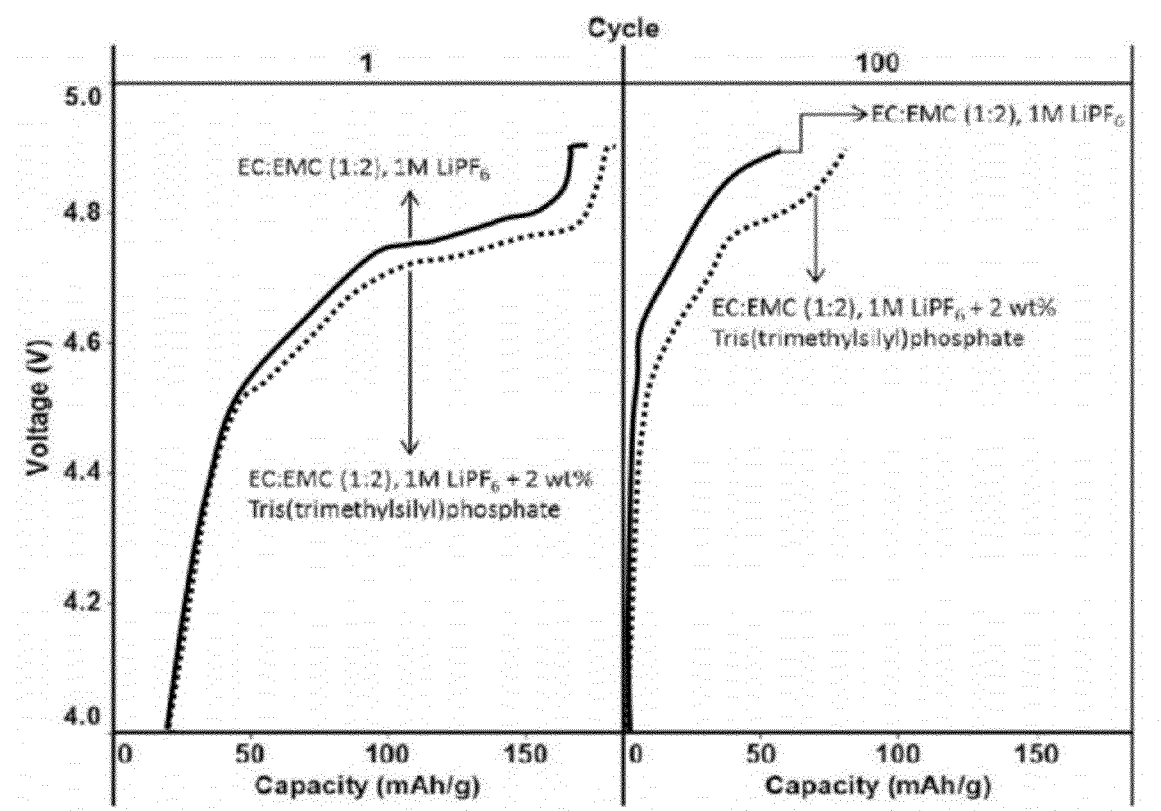
FIG. 27 sets forth voltage profiles at the $1^{st}$ and $100^{th}$ cycles during charging with and without a stabilizing additive, according to an embodiment of the invention.

Battery cells each including a doped $LiCoPO_4$ cathode material ($Li_{(1-x)}$: $Co_{(1-y-z)}$:$Fe_y$:$Ti_z$:$(PO_4)_{(1-a)}$) and a graphite anode (MCMB) were assembled using the methodology of Example 1. One cell included a conventional electrolyte (ethylene carbonate, ethyl methyl carbonate, and 1M $LiPF_6$) with about 2 wt. % of tris(trimethylsilyl)phosphate as a stabilizing additive, and another cell included the conventional electrolyte without the stabilizing additive (labeled as "EC:EMC (1:2), 1M $LiPF_6$"). The cells were cycled at room temperature (25° C.), and their voltage profiles at the $1^{st}$ and $100^{th}$ cycles during charging are set forth in FIG. 27. Higher voltage during charging is indicative of a resistance build-up. As can be appreciated, the inclusion of tris(trimethylsilyl)phosphate yielded a reduced cell resistance.

Example 21

Characterization of Battery Cells Including Stabilizing Additives

Figure 28:
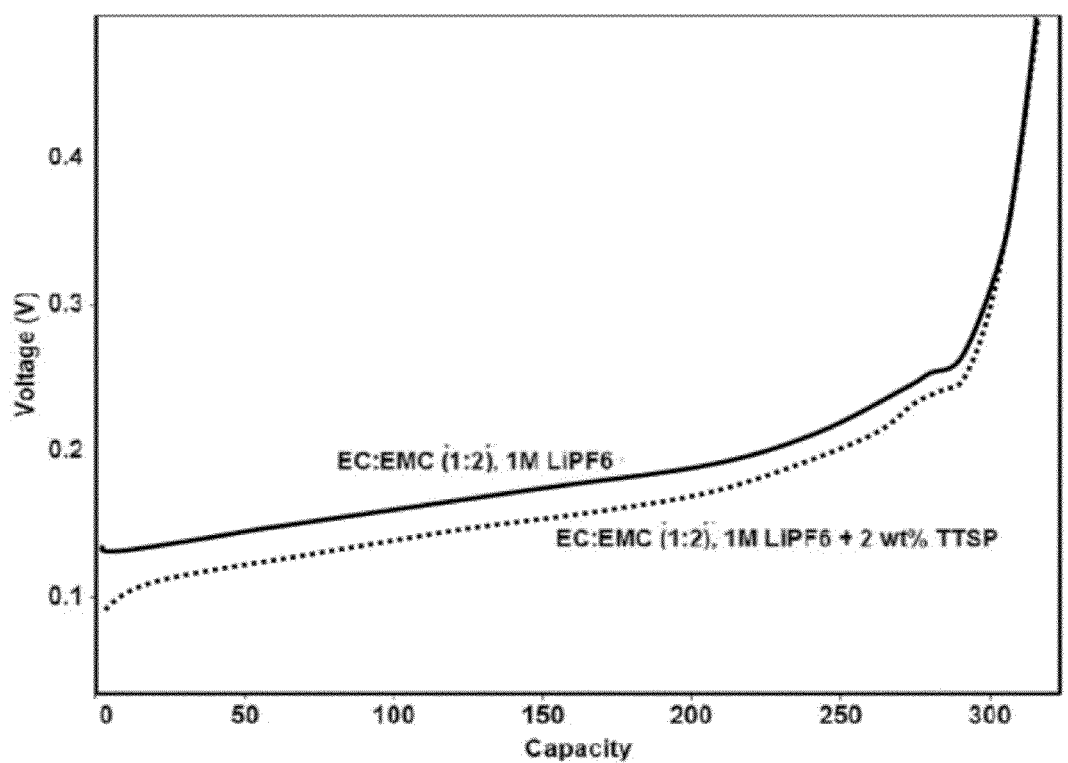
FIG. 28 sets forth voltage profiles at the $3^{rd}$ cycle during discharging with and without a stabilizing additive, according to an embodiment of the invention.

Half cells (including Li metal as an anode) were assembled using the methodology of Example 1. One cell included a conventional electrolyte (ethylene carbonate, ethyl methyl carbonate, and 1M $LiPF_6$) with about 2 wt. % of tris(trimethylsilyl)phosphate (labeled as "TTSP") as a stabilizing additive, and another cell included the conventional electrolyte without the stabilizing additive (labeled as "EC:EMC (1:2), 1M $LiPF_6$"). The cells were cycled at room temperature (25° C.), and their voltage profiles at the $3^{rd}$ cycle during discharging are set forth in FIG. 28. As can be appreciated, the inclusion of tris(trimethylsilyl)phosphate yielded a reduced cell resistance.

Example 22

Methodology for Formation and Characterization of Battery Cells Including Stabilizing Additives Battery cells were formed in a high purity argon filled glove box (M-Braun, O2 and humidity content <0.1 ppm). Initially, poly(vinylidene fluoride) (Sigma Aldrich), carbon black (Super P Li, TIMCAL), and a cathode material were mixed in 1-methyl-2-pyrrolidinone (Sigma Aldrich), and the resulting slurry was deposited on an aluminum current collector and dried to form a composite cathode film. A lithium or graphite anode was used. In case of a graphite anode, a graphitic carbon was mixed with poly(vinylidene fluoride) (Sigma Aldrich), carbon black (Super P Li, TIMCAL), using 1-methyl-2-pyrrolidinone (Sigma Aldrich) as a solvent, and the resulting slurry was deposited on a copper current collector and dried to form a composite anode film. Each battery cell including the composite cathode film, a Millipore glass fiber or a polypropylene separator, and the lithium or graphite anode was assembled in a coin cell-type assembly (CR2025, Hohsen). Cells with Li anodes are tested in Hohsen CR2032 cells. A conventional electrolyte was mixed with a stabilizing additive and added to the battery cell. The battery cell was sealed and cycled between a particular voltage range for each cathode at a particular temperature (e.g., room temperature or 25° C.). Table 1 shows cycling voltage range for each cathode in full cell. The upper cutoff voltage is 0.05V higher in a half cell than in a full cell.

TABLE 1

Cycling voltage range in full cell for different cathode

| Cathode | Cycling voltage, V |
| --- | --- |
| LMNO-type | 3-4.85 |
| CM1-type | 3-4.9 |
| LMO-type | 3-4.45 |
| NMC-type | 3-4.1 |
| NMC-type | 3-4.45 |
| OLO-type | 2-4.6 |

Example 23

Characterization of Battery Cells Including Stabilizing Additives

Figure 29:
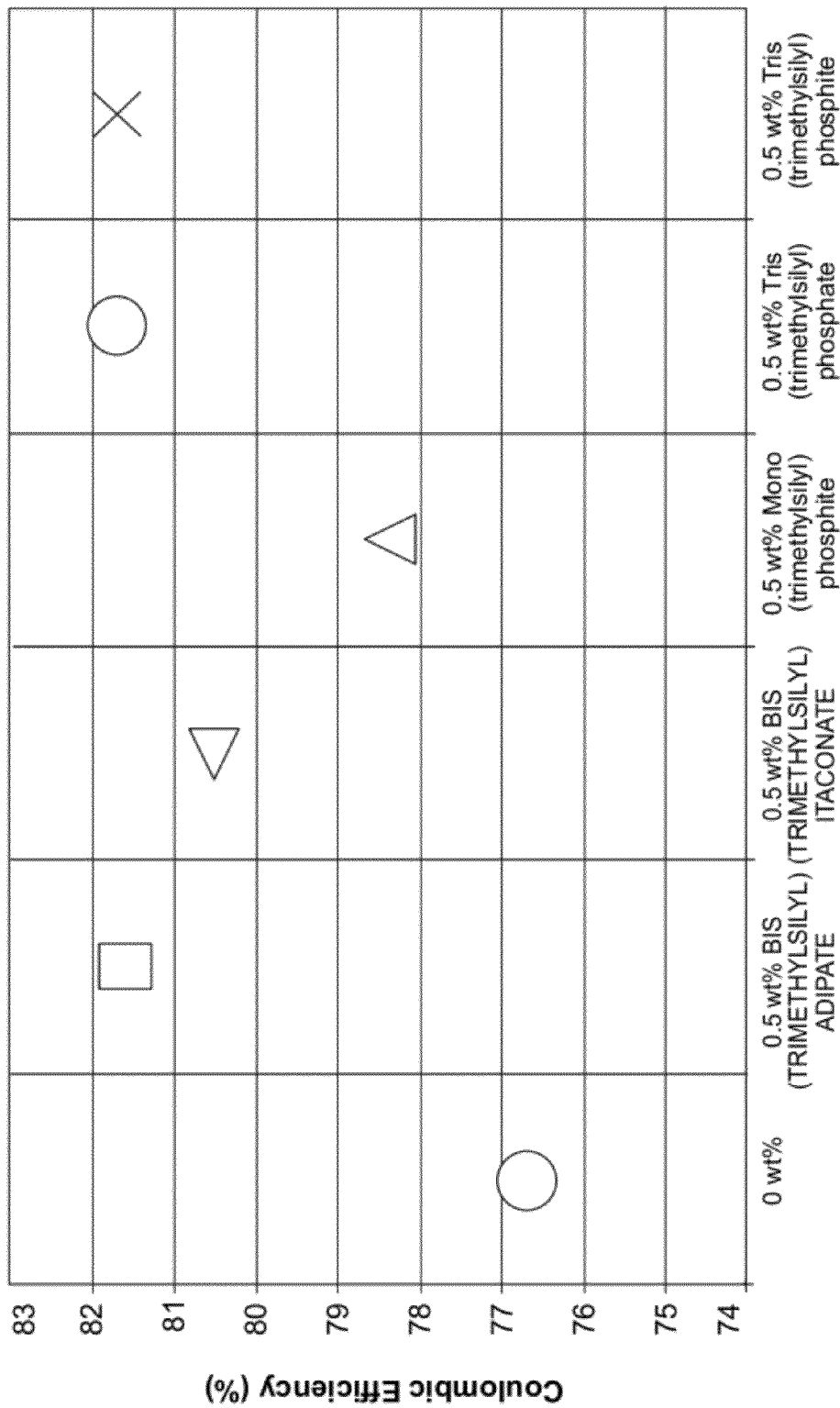
FIG. 29 compares coulombic efficiency of battery cells with and without stabilizing additives at the first cycle.

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was LMNO-type. FIG. 29 compares coulombic efficiency of the battery cells at the first cycle. It can be appreciated that several OTMS additives performed better than control.

Example 24

Characterization of Battery Cells Including Stabilizing Additives

Figure 30:
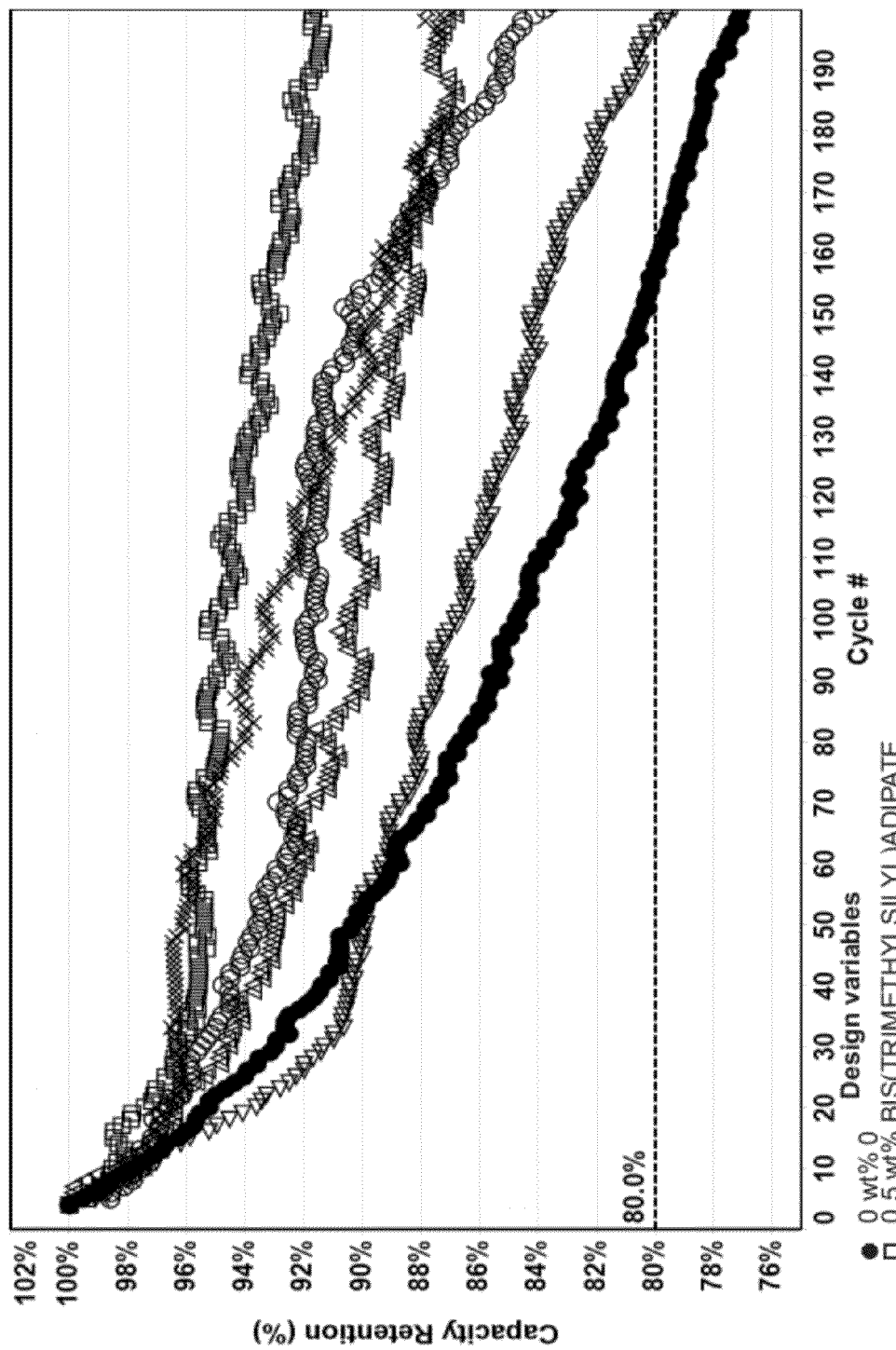
FIG. 30 compares capacity retention of the battery cells with and without stabilizing additives over several cycles, expressed in terms of a percentage of an initial specific capacity upon discharge retained at a particular cycle, according to an embodiment of the invention.

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was LMNO-type and the test was performed at room temperature. FIG. 30 compares capacity retention of the battery cells over several cycles, expressed in terms of a percentage of an initial specific capacity upon discharge retained at a particular cycle. It can be appreciated that several OTMS additives performed better than control.

Example 25

Characterization of Battery Cells Including Stabilizing Additives

Figure 31:
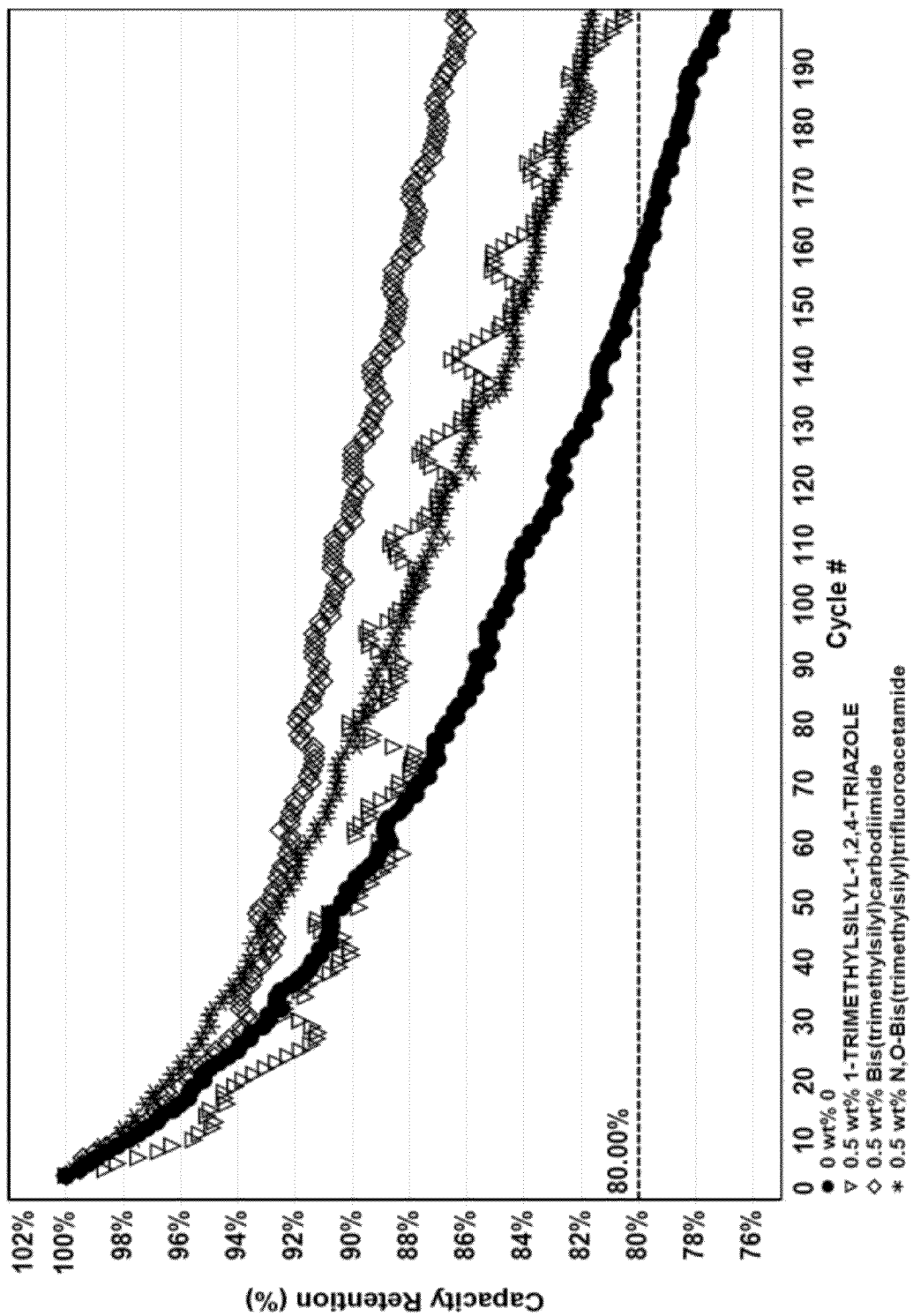
FIG. 31 compares capacity retention of the battery cells with and without stabilizing additives over several cycles, expressed in terms of a percentage of an initial specific capacity upon discharge retained at a particular cycle, according to an embodiment of the invention.

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was LMNO-type and the test was performed at room temperature. FIG. 31 compares capacity retention of the battery cells over several cycles, expressed in terms of a percentage of an initial specific capacity upon discharge retained at a particular cycle. It can be appreciated that several NTMS additives performed better than control.

Example 26

Characterization of Battery Cells Including Stabilizing Additives

Figure 32:
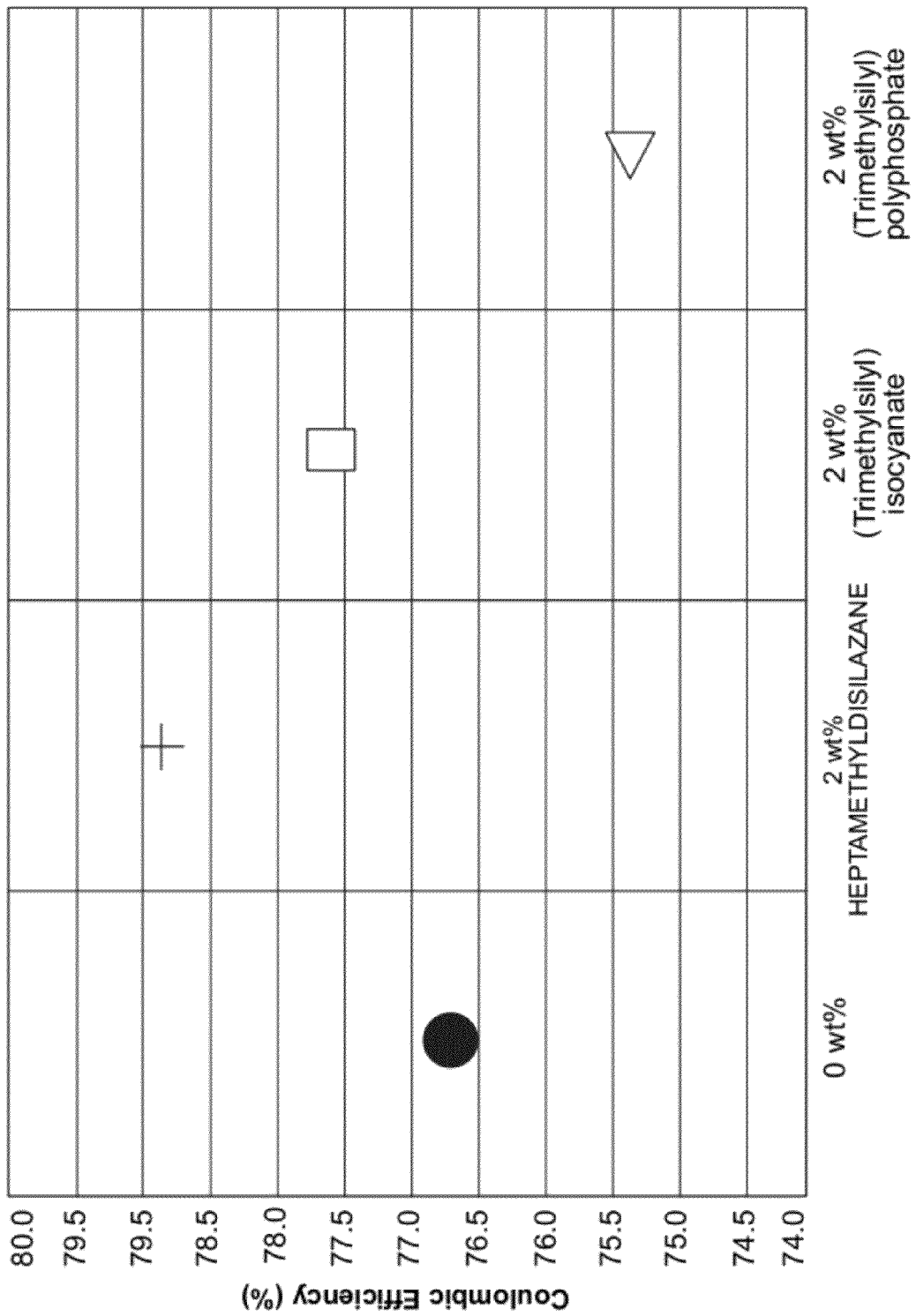
FIG. 32 compares coulombic efficiency of the battery cells with and without stabilizing additives at the first cycle, according to an embodiment of the invention.

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was LMNO-type and the test was performed at room temperature. FIG. 32 compares coulombic efficiency of the battery cells at the first cycle. It can be appreciated that several TMS additives performed better than control.

Example 27

Characterization of Battery Cells Including Stabilizing Additives

Figure 33:
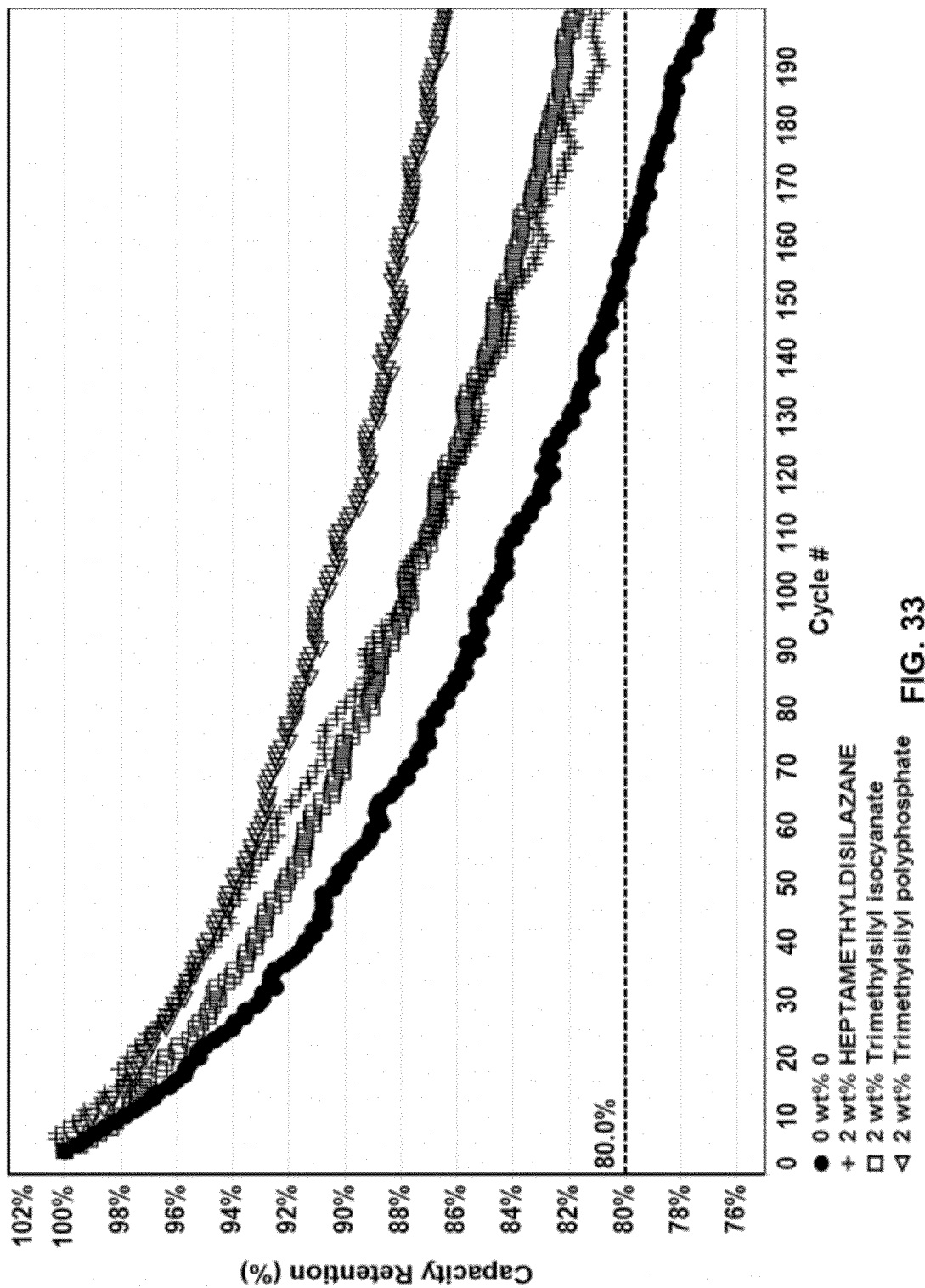
FIG. 33 compares capacity retention of the battery cells with and without stabilizing additives over several cycles, expressed in terms of a percentage of an initial specific capacity upon discharge retained at a particular cycle, according to an embodiment of the invention.

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was LMNO-type and the test was performed at room temperature. FIG. 33 compares capacity retention of the battery cells over several cycles, expressed in terms of a percentage of an initial specific capacity upon discharge retained at a particular cycle. It can be appreciated that several TMS additives performed better than control.

Example 28

Characterization of Battery Cells Including Stabilizing Additives

Figure 34:
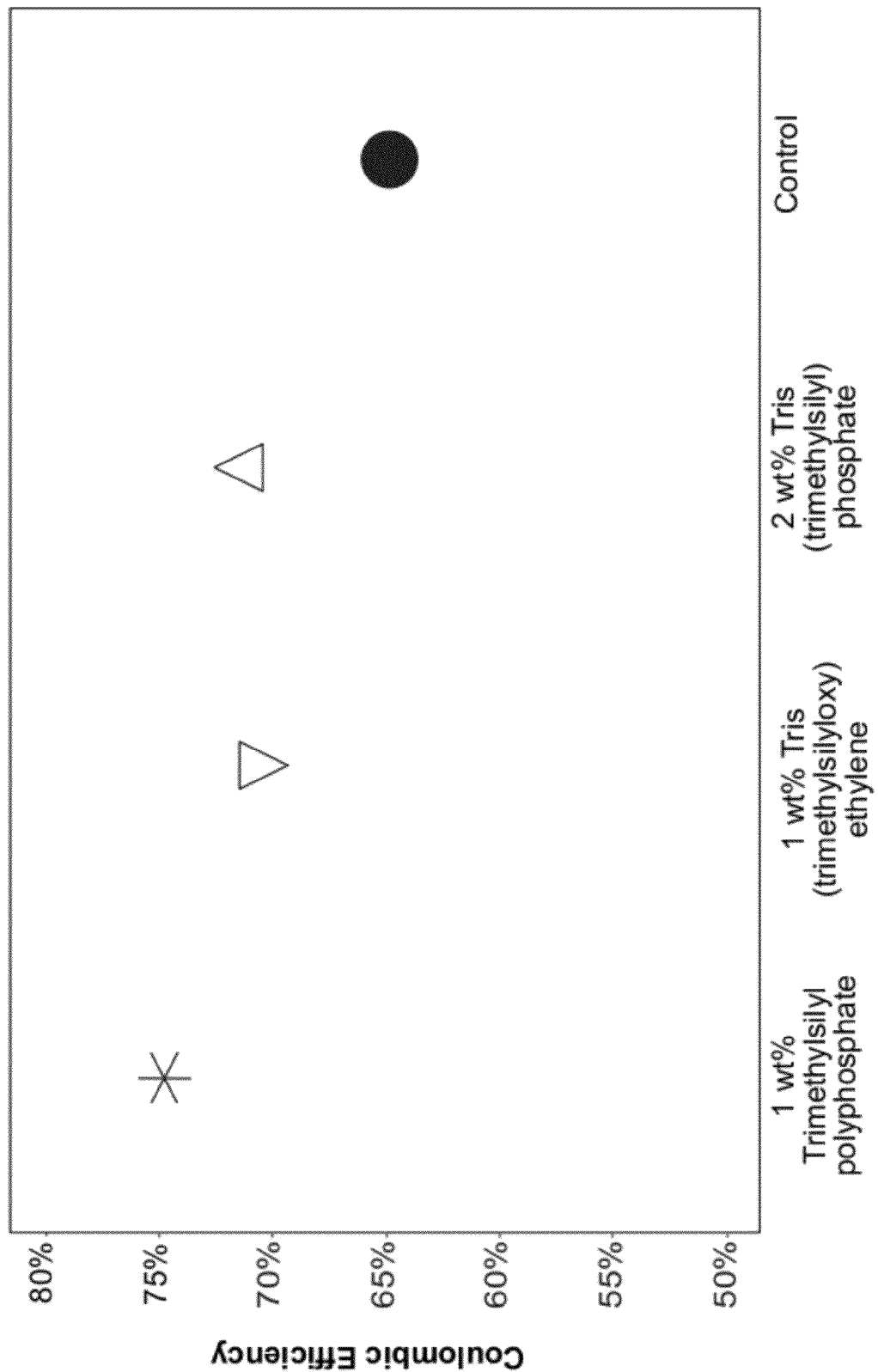
FIG. 34 compares coulombic efficiency of the battery cells with and without stabilizing additives at the first cycle, according to an embodiment of the invention.

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was CM1-type. FIG. 34 compares coulombic efficiency of the battery cells at the first cycle. It can be appreciated that several OTMS additives performed better than control.

Example 29

Characterization of Battery Cells Including Stabilizing Additives

Figure 35:
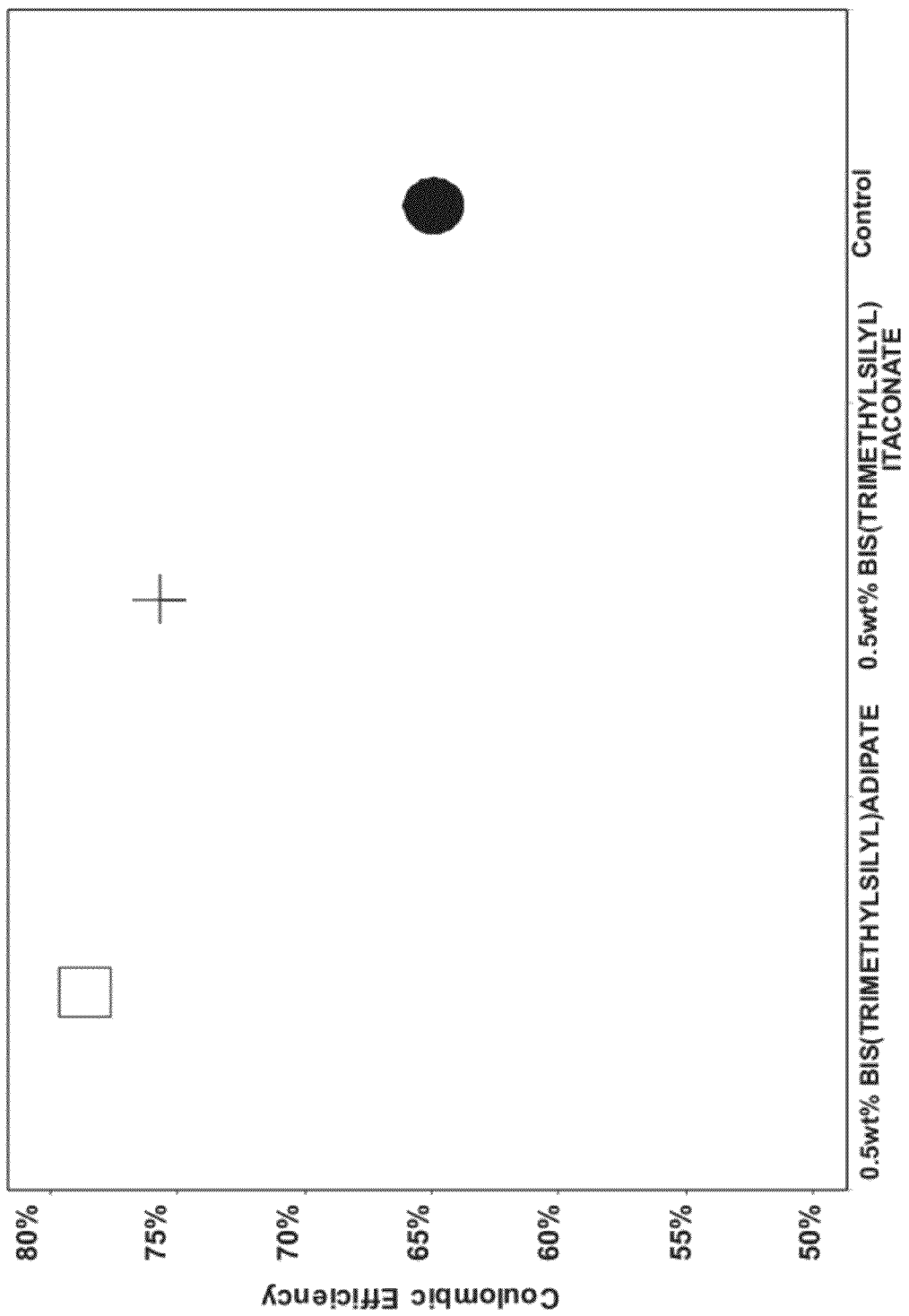
FIG. 35 compares coulombic efficiency of the battery cells with and without stabilizing additives at the first cycle, according to an embodiment of the invention.

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was CM1-type. FIG. 35 compares coulombic efficiency of the battery cells at the first cycle. It can be appreciated that several OTMS additives performed better than control.

Example 30

Characterization of Battery Cells Including Stabilizing Additives

Figure 36:
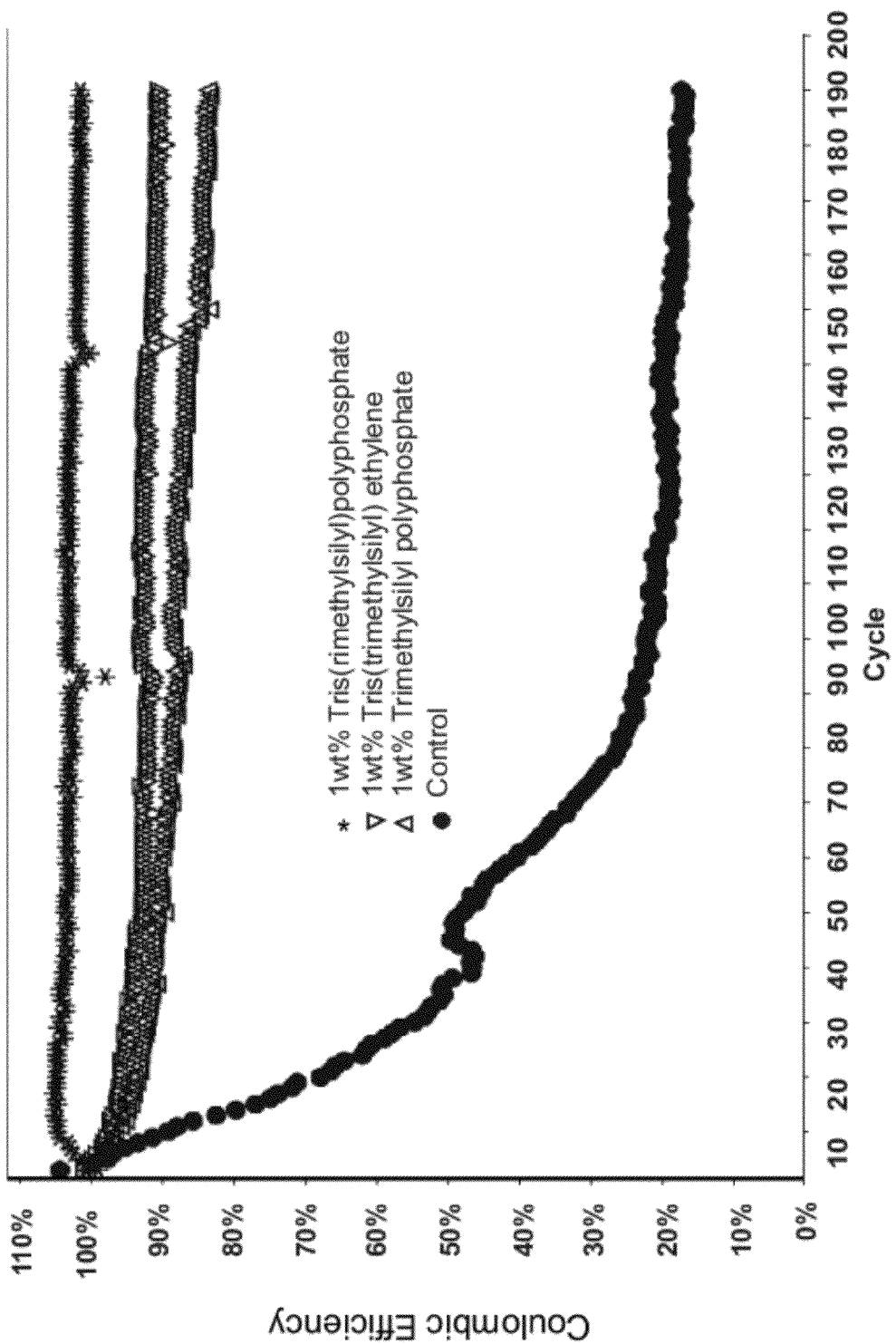
FIGS. 36 through 43 compare capacity retention of the battery cells with and without stabilizing additives over several cycles, expressed in terms of a percentage of an initial specific capacity upon discharge retained at a particular cycle, according to an embodiment of the invention.

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was CM1-type the test was performed at room temperature. FIG. 36 compares capacity retention of the battery cells over several cycles, expressed in terms of a percentage of an initial specific capacity upon discharge retained at a particular cycle. It can be appreciated that several OTMS additives performed better than control.

Example 31

Characterization of Battery Cells Including Stabilizing Additives

Figure 37:
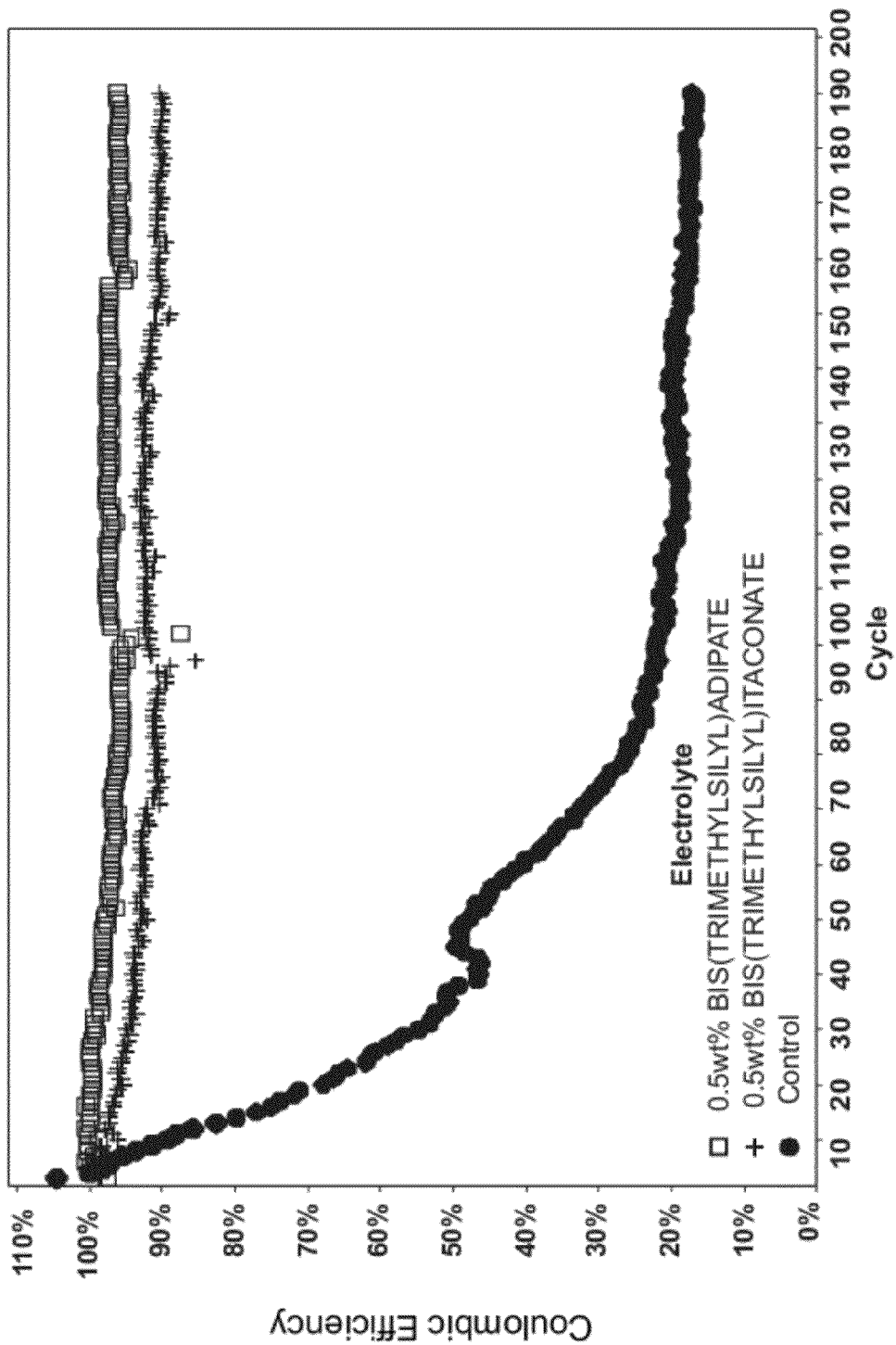

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was CM1-type and the test was performed at room temperature. FIG. 37 compares capacity retention of the battery cells over several cycles, expressed in terms of a percentage of an initial specific capacity upon discharge retained at a particular cycle. It can be appreciated that several OTMS additives performed better than control.

Example 32

Characterization of Battery Cells Including Stabilizing Additives

Figure 38:
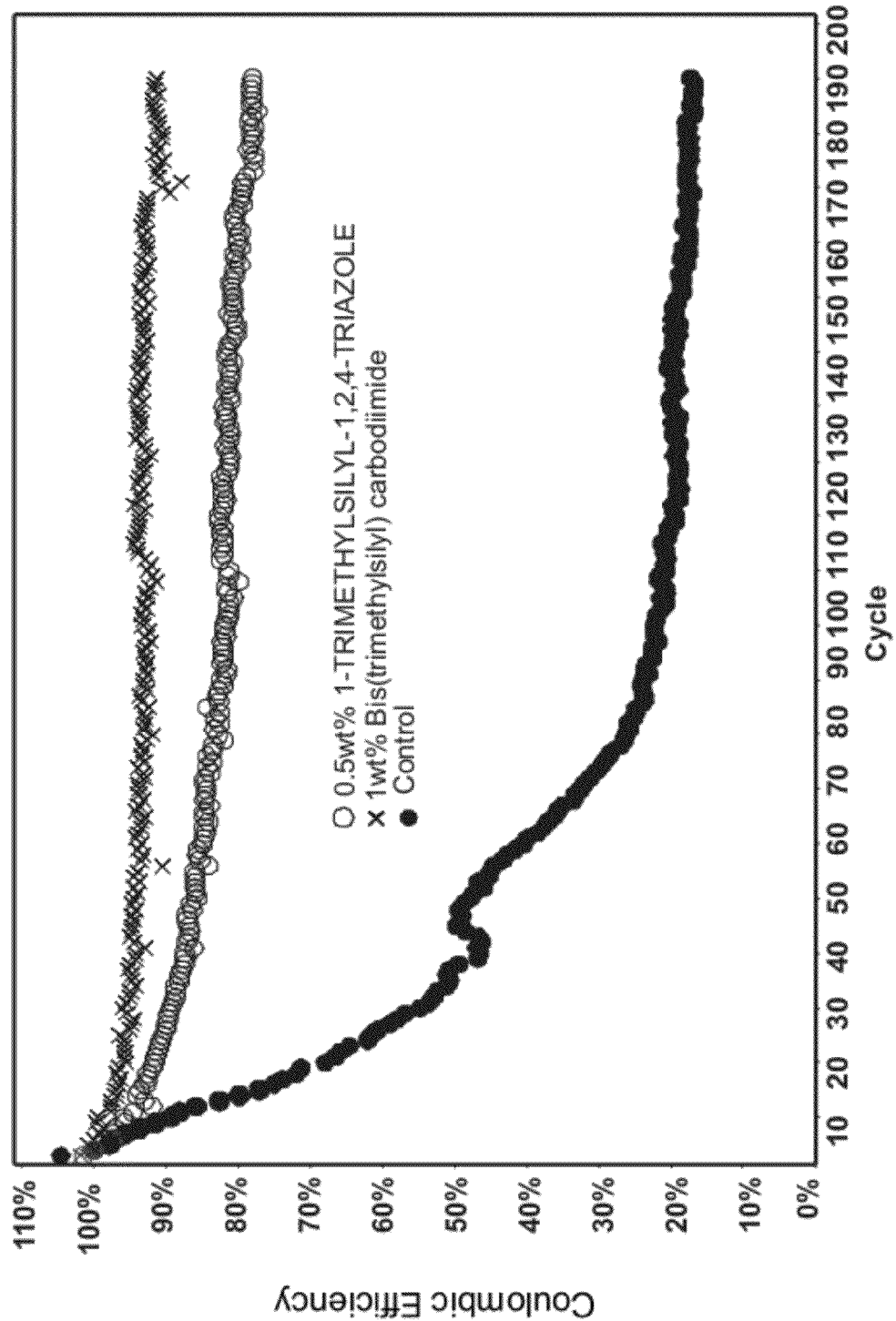

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was CM1-type and the test was performed at room temperature. FIG. 38 compares capacity retention of the battery cells over several cycles, expressed in terms of a percentage of an initial specific capacity upon discharge retained at a particular cycle. It can be appreciated that several NTMS additives performed better than control.

Example 33

Characterization of Battery Cells Including Stabilizing Additives

Figure 39:
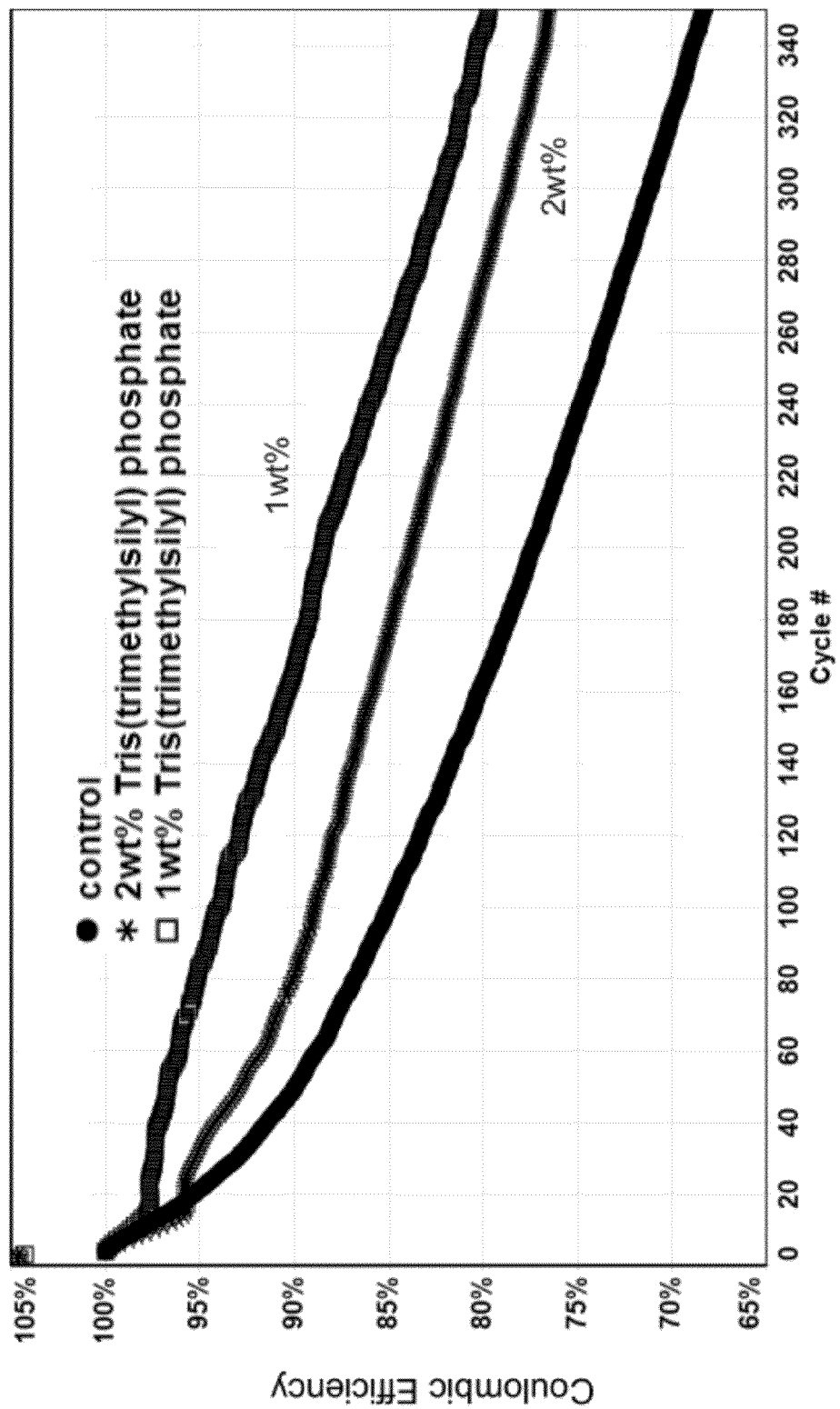

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was NMC-type and the test was performed at high temperature. FIG. 39 compares capacity retention of the battery cells over several cycles, expressed in terms of a percentage of an initial specific capacity upon discharge retained at a particular cycle. It can be appreciated that OTMS additives performed better than control.

Example 34

Characterization of Battery Cells Including Stabilizing Additives

Figure 40:
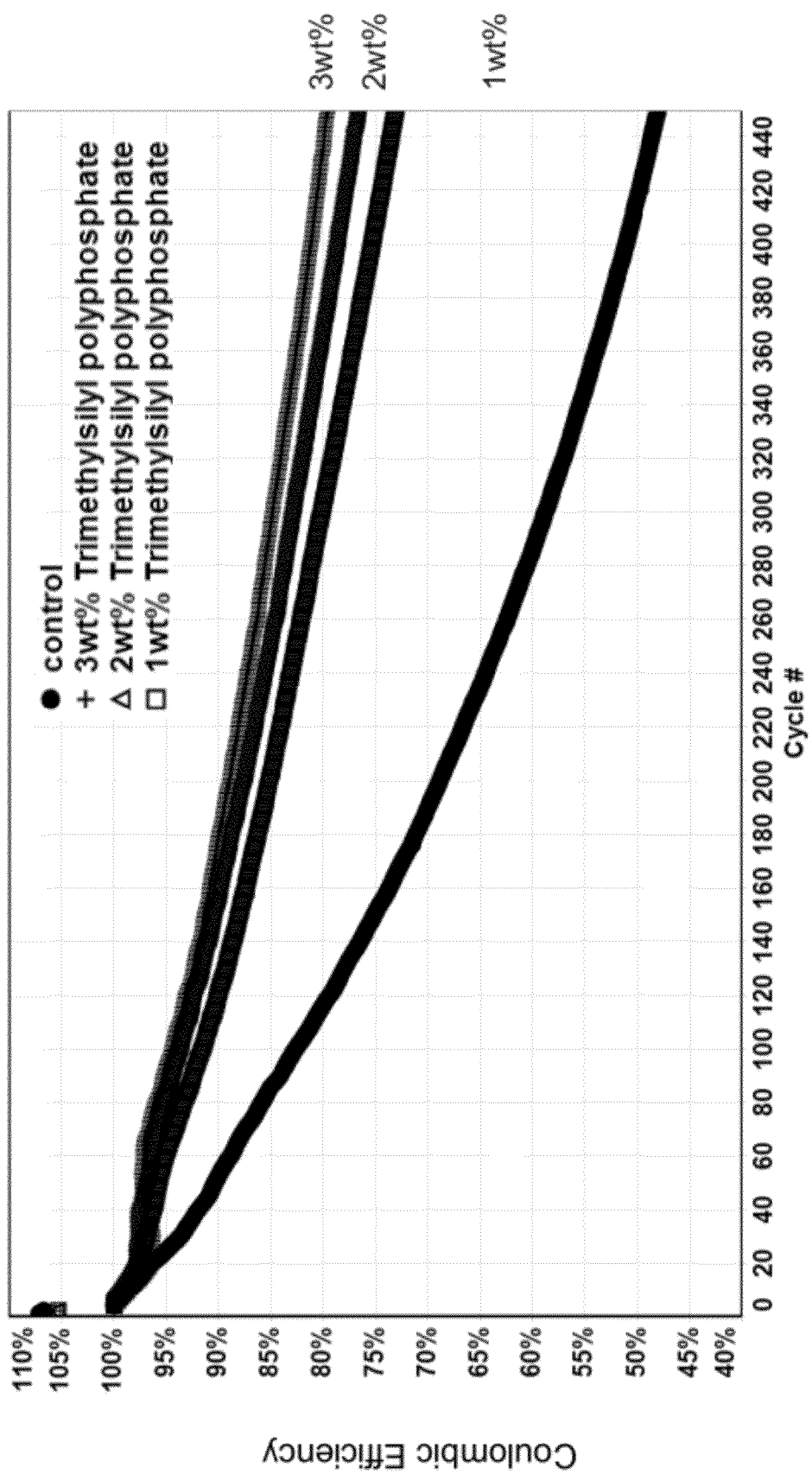

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was NMC-type and the test was performed at high temperature. FIG. 40 compares capacity retention of the battery cells over several cycles, expressed in terms of a percentage of an initial specific capacity upon discharge retained at a particular cycle. It can be appreciated that OTMS additives performed better than control.

Example 35

Characterization of Battery Cells Including Stabilizing Additives

Figure 41:
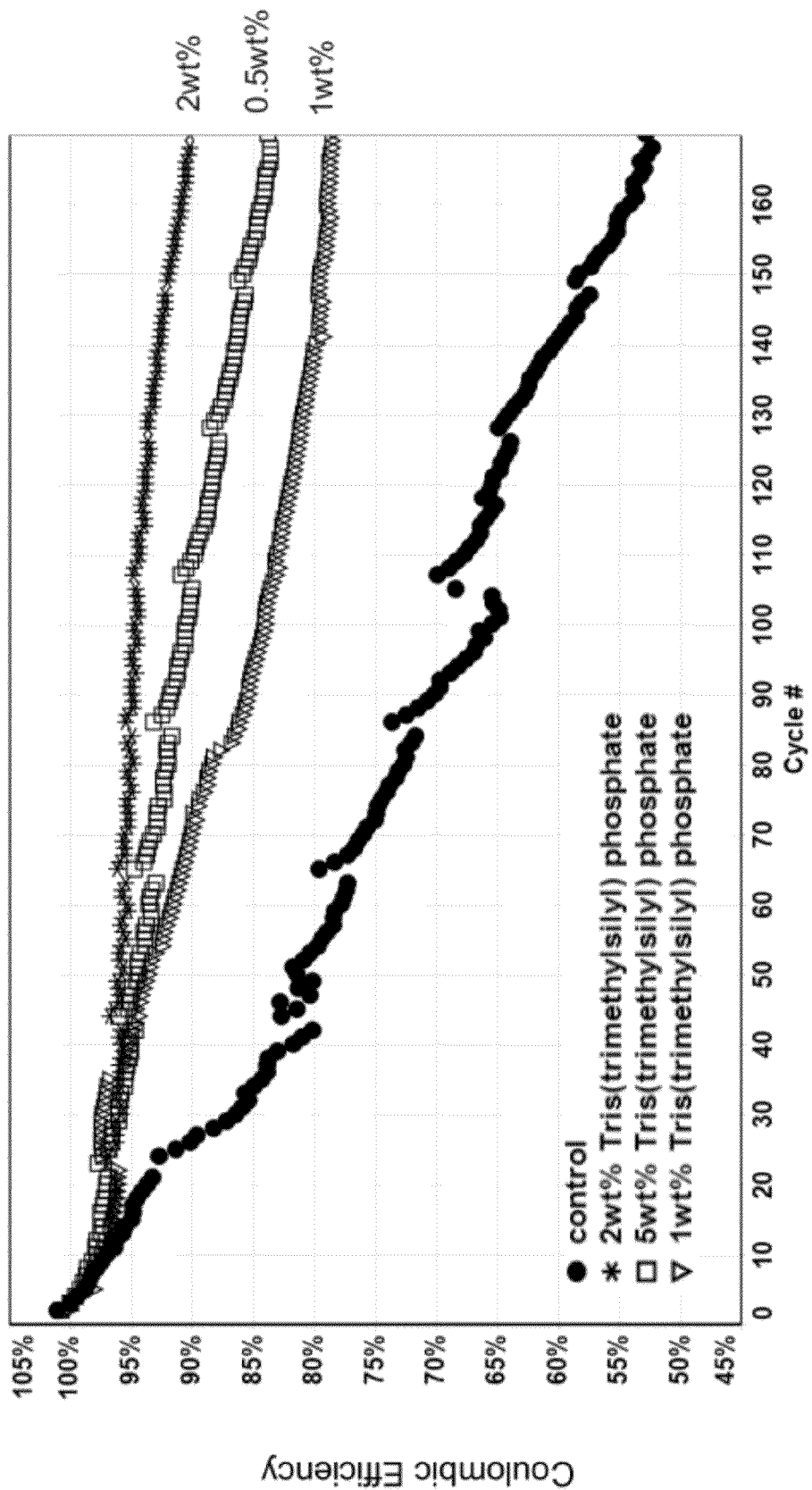

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was OLO-type and the test was performed at room temperature. FIG. 41 compares capacity retention of the battery cells over several cycles, expressed in terms of a percentage of an initial specific capacity upon discharge retained at a particular cycle. It can be appreciated that OTMS additives performed better than control.

Example 36

Characterization of Battery Cells Including Stabilizing Additives

Figure 42:
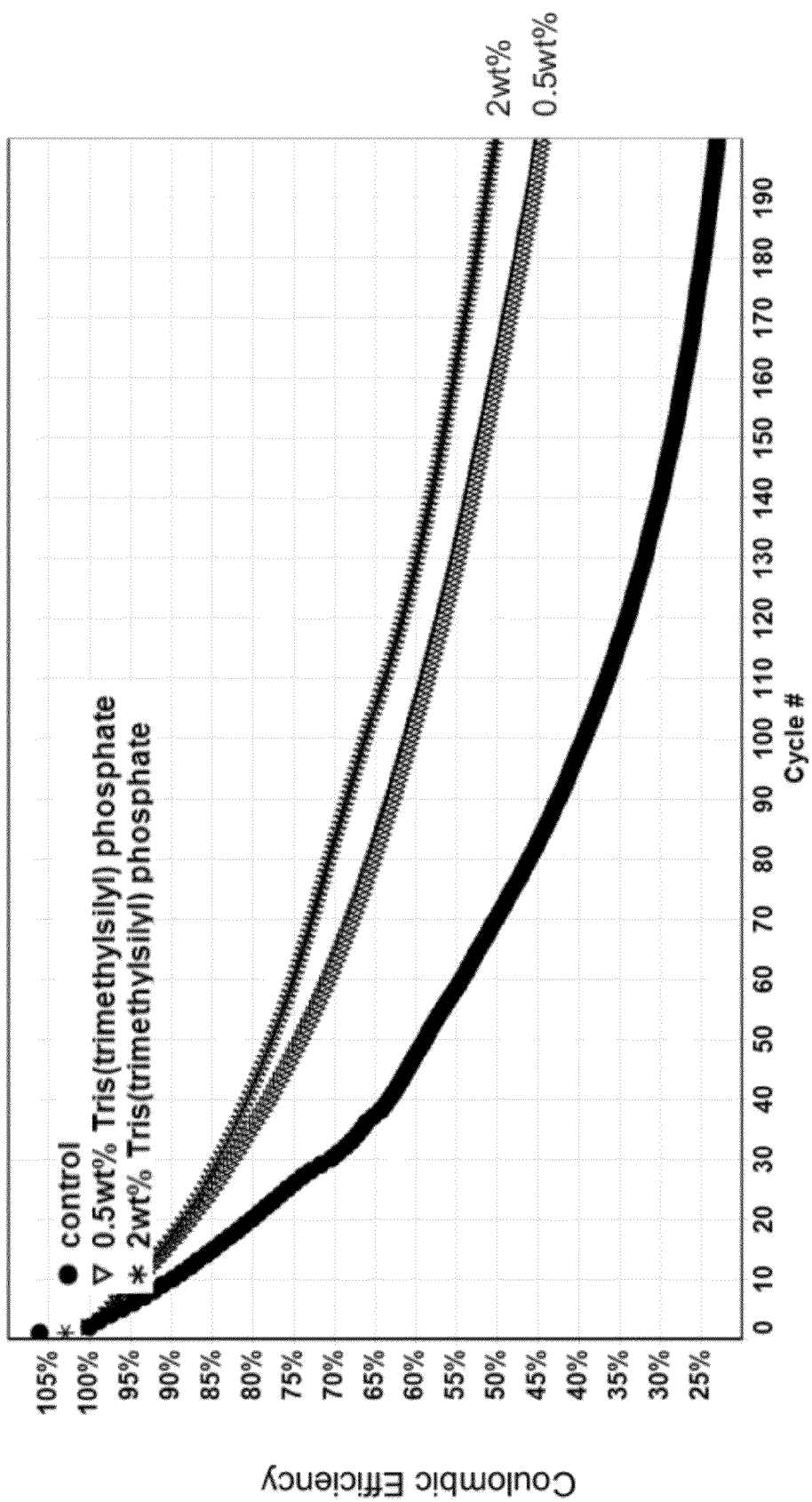

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was OLO-type and the test was performed at high temperature. FIG. 42 compares capacity retention of the battery cells over several cycles, expressed in terms of a percentage of an initial specific capacity upon discharge retained at a particular cycle. It can be appreciated that OTMS additives performed better than control.

Example 36

Characterization of Battery Cells Including Stabilizing Additives

Figure 43:
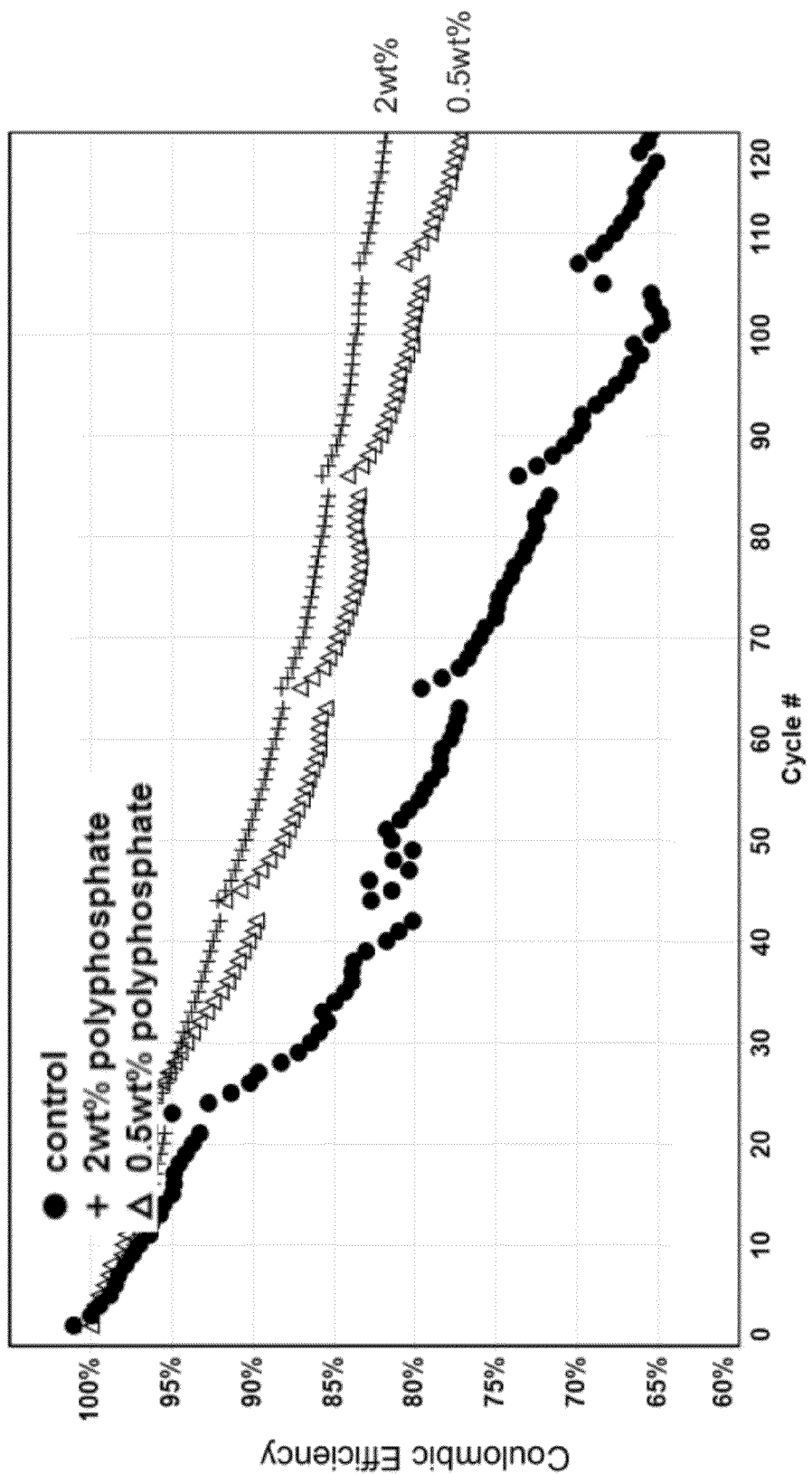

Using the methodology of Example 22, performance characteristics were measured for test battery cells including different silicon-containing stabilizing additives dispersed in a conventional electrolyte (ethylene carbonate, ethyl methyl carbonate, and 1M $LiPF_6$) and for a control battery cell including the conventional electrolyte but without a stabilizing additive. In this example, the cathode material was OLO-type and the test was performed at room temperature. FIG. 43 compares capacity retention of the battery cells over several cycles, expressed in terms of a percentage of an initial specific capacity upon discharge retained at a particular cycle. It can be appreciated that OTMS additives performed better than control.

Example 37

Characterization of Battery Cells Including Stabilizing Additives

Figure 44:
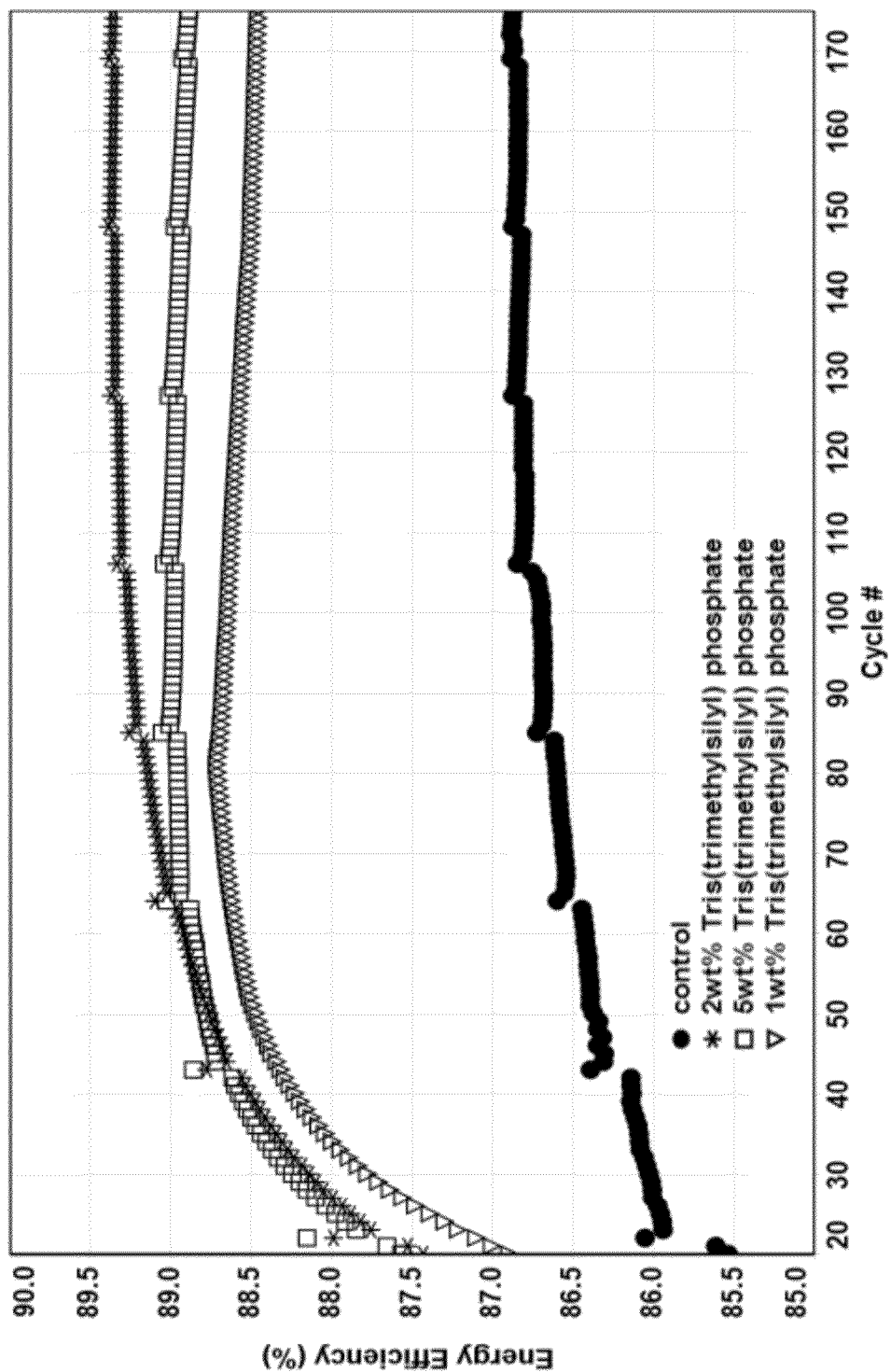
FIG. 44 compares energy efficiency of the battery cells with and without stabilizing additives over several cycles, according to an embodiment of the invention.

Using the methodology of Example 22, performance characteristics were measured for test battery cells including different silicon-containing stabilizing additives dispersed in a conventional electrolyte (ethylene carbonate, ethyl methyl carbonate, and 1M LiPF$_6$) and for a control battery cell including the conventional electrolyte but without a stabilizing additive. In this example, the cathode material was OLO-type and the test was performed at room temperature. FIG. 44 compares energy efficiency of the battery cells over several cycles. It can be appreciated that OTMS additives performed better than control.

Example 38

Characterization of Battery Cells Including Stabilizing Additives

Figure 45:
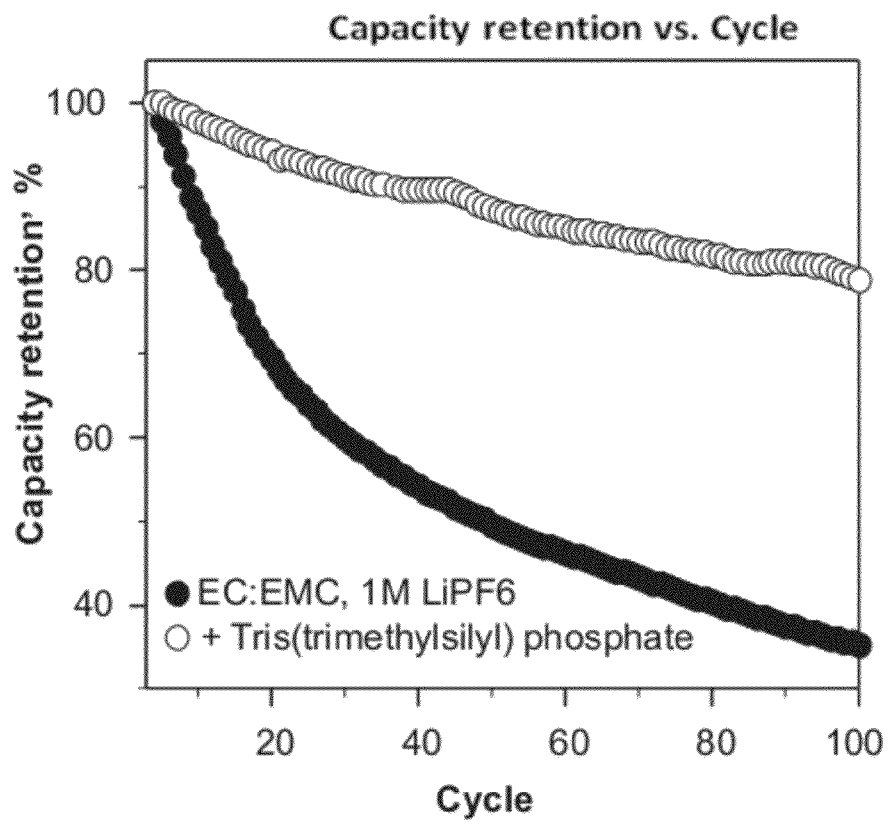
FIG. 45 and FIG. 46 compare capacity retention of the battery cells with and without stabilizing additives over several cycles, expressed in terms of a percentage of an initial specific capacity upon discharge retained at a particular cycle, according to an embodiment of the invention.

Using the methodology of Example 22, performance characteristics were measured for test battery cells including different silicon-containing stabilizing additives dispersed in a conventional electrolyte (ethylene carbonate, ethyl methyl carbonate, and 1M LiPF$_6$) and for a control battery cell including the conventional electrolyte but without a stabilizing additive. In this example, the cathode material was LMNO-type and the test was performed at high temperature. FIG. 45 compares capacity retention of the battery cells over several cycles, expressed in terms of a percentage of an initial specific capacity upon discharge retained at a particular cycle. It can be appreciated that OTMS additives performed better than control.

Example 39

Characterization of Battery Cells Including Stabilizing Additives

Figure 46:
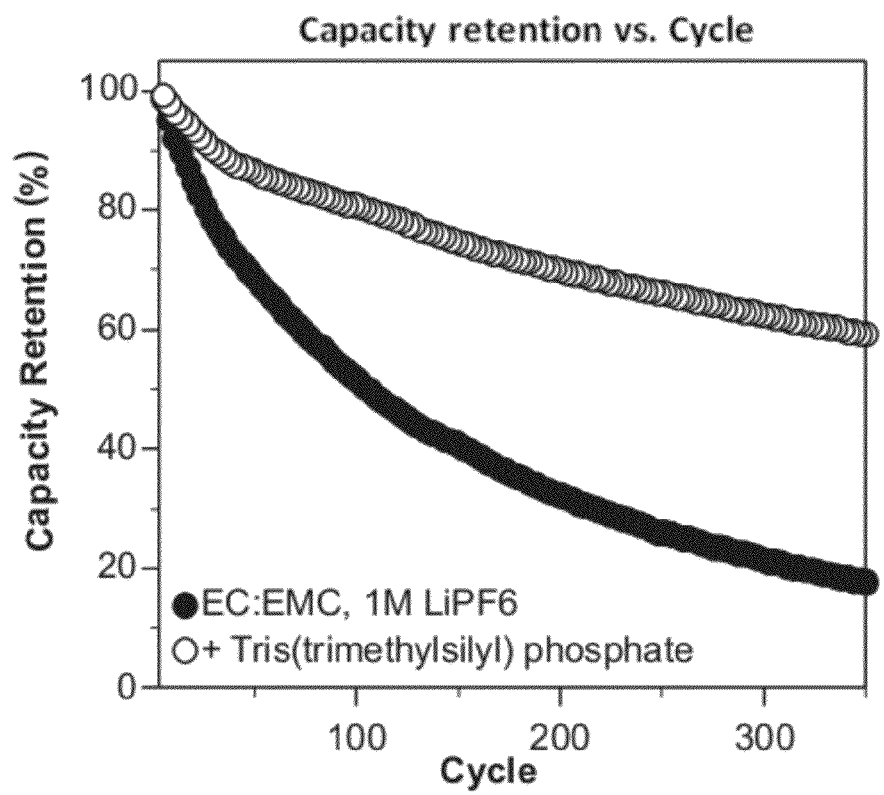

Using the methodology of Example 22, performance characteristics were measured for test battery cells including different silicon-containing stabilizing additives dispersed in a conventional electrolyte (ethylene carbonate, ethyl methyl carbonate, and 1M LiPF$_6$) and for a control battery cell including the conventional electrolyte but without a stabilizing additive. In this example, the cathode material was LMO-type and the test was performed at high temperature. FIG. 46 compares capacity retention of the battery cells over several cycles, expressed in terms of a percentage of an initial specific capacity upon discharge retained at a particular cycle. It can be appreciated that OTMS additives performed better than control.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, or process to the objective, spirit and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. A composition for use in an electrolyte solution, comprising:
a compound represented by the formula (I):

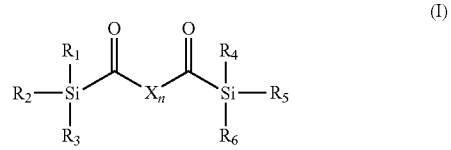

wherein n is an integer from 1 to 20;
X is represented by the formula (II):

wherein for each X of the n number of X's, $R_a$ is selected from the group consisting of hydrogen, substituted and unsubstituted $C_1$-$C_{20}$ alkenyl groups, $R_b$, is either not present or hydrogen, and $R_c$ and $R_d$ are each independently selected from the group consisting of substituted and unsubstituted $C_1$-$C_{20}$ alkyl groups, substituted and unsubstituted $C_1$-$C_{20}$ alkenyl groups, substituted and unsubstituted $C_1$-$C_{20}$ alkynyl groups, and substituted and unsubstituted $C_5$-$C_{20}$ aryl groups; and $R_1$, $R_2$, $R_3$, $R_4$, $R_5$, and $R_6$ are independently selected from the group consisting of substituted and unsubstituted $C_1$-$C_{20}$ alkyl groups, substituted and unsubstituted $C_1$-$C_{20}$ alkenyl groups, substituted and unsubstituted $C_1$-$C_{20}$ alkynyl groups, and substituted and unsubstituted $C_5$-$C_{20}$ aryl groups.

2. The composition of claim 1 wherein $R_a$ is selected from the group consisting of substituted and unsubstituted $C_1$-$C_6$ alkenyl groups.

3. The composition of claim 1 wherein $R_a$ is a $C_1$ alkenyl group and $R_b$ is not present.

4. The composition of claim 1 wherein $R_1$, $R_2$, $R_3$, $R_4$, $R_5$, and $R_6$ are independently selected from the group consisting of substituted and unsubstituted $C_1$-$C_6$ alkyl groups.

5. The composition of claim 1 wherein $R_1$, $R_2$, $R_3$, $R_4$, $R_5$, and $R_6$ are independently selected from the group consisting of substituted and unsubstituted $C_1$ alkyl groups.

6. The composition of claim 1 wherein $R_1$, $R_2$, $R_3$, $R_4$, $R_5$, and $R_6$ are each $C_1$ alkyl groups.

7. The composition of claim 1 wherein $R_c$ and $R_d$ are each independently selected from the group consisting of substituted and unsubstituted $C_3$-$C_6$ alkyl groups, substituted and unsubstituted $C_4$-$C_{12}$ alkynyl groups, and substituted and unsubstituted $C_5$-$C_{12}$ aryl groups.

8. The composition of claim 1 wherein the compound is represented by the formula (III):

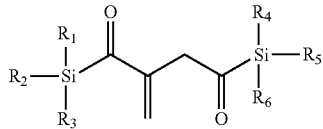

wherein $R_1$, $R_2$, $R_3$, $R_4$, $R_5$, and $R_6$ are independently selected from the group consisting of substituted and unsubstituted $C_1$-$C_6$ alkyl groups.

9. The composition of claim 1 wherein the compound is represented by the formula (IV):

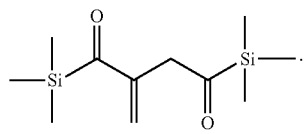

10. An electrolyte solution comprising:
a salt;
a solvent; and
a compound represented by the formula (I):

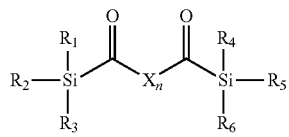

wherein n is an integer from 1 to 20;
X is represented by the formula (II):

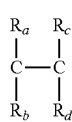

wherein for each X of the n number of X's, $R_a$ is selected from the group consisting of substituted and unsubstituted $C_1$-$C_{20}$ alkenyl groups, $R_b$, is either not present or hydrogen, and $R_c$ and $R_d$ are each independently selected from the group consisting of hydrogen, substituted and unsubstituted $C_1$-$C_{20}$ alkyl groups, substituted and unsubstituted $C_1$-$C_{20}$ alkenyl groups, substituted and unsubstituted $C_1$-$C_{20}$ alkynyl groups, and substituted and unsubstituted $C_5$-$C_{20}$ aryl groups; and
$R_1$, $R_2$, $R_3$, $R_4$, $R_5$, and $R_6$ are independently selected from the group consisting of substituted and unsubstituted $C_1$-$C_{20}$ alkyl groups, substituted and unsubstituted $C_1$-$C_{20}$ alkenyl groups, substituted and unsubstituted $C_1$-$C_{20}$ alkynyl groups, and substituted and unsubstituted $C_5$-$C_{20}$ aryl groups.

11. The electrolyte solution of claim 10 wherein $R_a$ is selected from the group consisting of substituted and unsubstituted $C_1$-$C_6$ alkenyl groups.

12. The electrolyte solution of claim 10 wherein $R_a$ is a $C_1$ alkenyl group and $R_b$ is not present.

13. The electrolyte solution of claim 10 wherein $R_1$, $R_2$, $R_3$, $R_4$, $R_5$, and $R_6$ are independently selected from the group consisting of substituted and unsubstituted $C_1$-$C_6$ alkyl groups.

14. The electrolyte solution of claim 10 wherein $R_1$, $R_2$, $R_3$, $R_4$, $R_5$, and $R_6$ are independently selected from the group consisting of substituted and unsubstituted $C_1$ alkyl groups.

15. The electrolyte solution of claim 10 wherein $R_1$, $R_2$, $R_3$, $R_4$, $R_5$, and $R_6$ are each $C_1$ alkyl groups.

16. The electrolyte solution of claim 10 wherein $R_c$ and $R_d$ are each independently selected from the group consisting of substituted and unsubstituted $C_3$-$C_6$ alkyl groups, substituted and unsubstituted $C_4$-$C_{12}$ alkynyl groups, and substituted and unsubstituted $C_5$-$C_{12}$ aryl groups.

17. The electrolyte solution of claim 10 wherein the compound is represented by the formula (III):

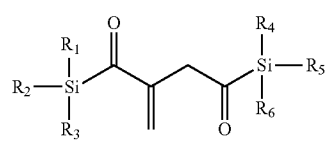

wherein $R_1$, $R_2$, $R_3$, $R_4$, $R_5$, and $R_6$ are independently selected from the group consisting of substituted and unsubstituted $C_1$-$C_6$ alkyl groups.

18. The electrolyte solution of claim 10 wherein the compound is represented by the formula (IV):

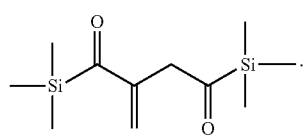

19. A method of making an electrolyte solution, comprising:
providing a non-aqueous solvent;
providing a lithium salt; and
providing a compound represented by the formula (I):

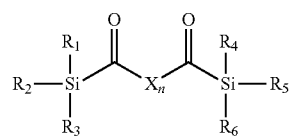

wherein n is an integer from 1 to 20;
X is represented by the formula (II):

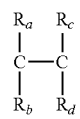

wherein for each X of the n number of X's, $R_a$ is selected from the group consisting of substituted and unsubstituted $C_1$-$C_{20}$ alkenyl groups, $R_b$, is either not present or hydrogen, and $R_c$ and $R_d$ are each independently selected from the group consisting of hydrogen, substituted and unsubstituted $C_1$-$C_{20}$ alkyl groups, substituted and unsubstituted $C_1$-$C_{20}$ alkenyl groups, substituted and unsubstituted $C_1$-$C_{20}$ alkynyl groups, and substituted and unsubstituted $C_5$-$C_{20}$ aryl groups; and $R_1$, $R_2$, $R_3$, $R_4$, $R_5$, and $R_6$ are independently selected from the group consisting of substituted and unsubstituted $C_1$-$C_{20}$ alkyl groups, substituted and unsubstituted $C_1$-$C_{20}$ alkenyl groups, substituted and unsubstituted $C_1$-$C_{20}$ alkynyl groups, and substituted and unsubstituted $C_5$-$C_{20}$ aryl groups; and combining the solvent, salt, and compound.

20. The method of claim 19 wherein the compound is represented by the formula (III):

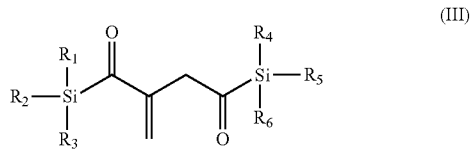

wherein $R_1$, $R_2$, $R_3$, $R_4$, $R_5$, and $R_6$ are independently selected from the group consisting of substituted and unsubstituted $C_1$-$C_6$ alkyl groups.

* * * * *